United States Patent
Jeschke et al.

(10) Patent No.: US 10,239,859 B2
(45) Date of Patent: Mar. 26, 2019

(54) NITROGEN-CONTAINING HETEROCYCLES AS PESTICIDES

(71) Applicant: Bayer CropScience Aktiengesellschaft, Monheim am Rhein (DE)

(72) Inventors: Peter Jeschke, Bergisch Gladbach (DE); Oliver Gutbrod, Langenfeld (DE); Reiner Fischer, Monheim (DE); Elke Hellwege, Langenfeld (DE); Peter Loesel, Leverkusen (DE); Olga Malsam, Roesrath (DE); Sascha Eilmus, Leichlingen (DE); Kerstin Ilg, Cologne (DE); Daniela Portz, Vettweiss (DE); Ulrich Goergens, Ratingen (DE); Anton Lishchynskyi, Duesseldorf (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/742,369

(22) PCT Filed: Jul. 4, 2016

(86) PCT No.: PCT/EP2016/065655
§ 371 (c)(1),
(2) Date: Jan. 5, 2018

(87) PCT Pub. No.: WO2017/005673
PCT Pub. Date: Jan. 12, 2017

(65) Prior Publication Data
US 2018/0201600 A1    Jul. 19, 2018

(30) Foreign Application Priority Data
Jul. 6, 2015 (EP) .................................. 15175448

(51) Int. Cl.
*C07D 401/04* (2006.01)
*C07D 213/74* (2006.01)
*C07D 417/04* (2006.01)
*A01N 43/40* (2006.01)
*C07D 401/14* (2006.01)

(52) U.S. Cl.
CPC .......... *C07D 401/04* (2013.01); *A01N 43/40* (2013.01); *C07D 213/74* (2013.01); *C07D 401/14* (2013.01); *C07D 417/04* (2013.01)

(58) Field of Classification Search
CPC ............................. C07D 401/04; A01N 43/40
See application file for complete search history.

(56) References Cited

U.S. PATENT DOCUMENTS

| | | |
|---|---|---|
| 7,186,834 B2 | 3/2007 | Muller et al. |
| 7,329,757 B2 | 2/2008 | Muller et al. |
| 2004/0029881 A1 | 2/2004 | Muller et al. |
| 2007/0259924 A1 | 11/2007 | Song et al. |

FOREIGN PATENT DOCUMENTS

| | | |
|---|---|---|
| DE | 19856966 A1 | 6/2000 |
| DE | 10024938 A1 | 11/2001 |
| EP | 0259738 A2 | 3/1988 |
| EP | 1286968 A2 | 3/2003 |
| WO | 00/34257 A1 | 6/2000 |
| WO | 01/90071 A2 | 11/2001 |

OTHER PUBLICATIONS

PCT International Search Report for PCT/EP2016/065655, dated Aug. 21, 2016.
Umesh D. Patil et al: "A convenient regioselective synthesis . . . ", Tetrahedron Letters, vol. 54, No. 4, Jan. 2013, pp. 343-346, XP055212059.

*Primary Examiner* — Golam M Shameem
(74) *Attorney, Agent, or Firm* — McBee Moore Woodward & Vanik IP, LLC

(57) ABSTRACT

The present application relates to novel heterocyclic compounds, to processes and intermediates for the preparation thereof, and their use for controlling animal pests.

14 Claims, No Drawings

NITROGEN-CONTAINING HETEROCYCLES AS PESTICIDES

CROSS REFERENCE TO RELATED APPLICATIONS

This application is a § 371 National State Application of PCT/EP2016/065655, filed Jul. 4, 2016, which claims priority to European Application No. 15175448.8 filed Jul. 6, 2015.

BACKGROUND OF THE INVENTION

Field of the Invention

The present application relates to novel heterocyclic compounds, to processes and intermediates for the preparation thereof, and their use for controlling animal pests.

Description of Related Art

DE 10024938 A1 describes the preparation of phenyliminoazines having herbicidal activity.

US 2007/0259924 A1 describes imidazoles containing an N-[1-aryl-2(1H)-pyridinylidene]cyanamide fragment as factor Xa inhibitors.

Crop protection agents, which also include pesticides, have to meet many demands, for example in relation to extent, persistence, and spectrum of their action and possible use. Questions of toxicity and of combinability with other active compounds or formulation auxiliaries play a role, as does the question of the expense that the synthesis of an active compound requires. In addition, resistances can occur. For all these reasons, the search for novel crop protection agents cannot be considered to be complete, and there is a constant need for novel compounds having properties which, compared to the known compounds, are improved at least in relation to individual aspects.

SUMMARY

It was an object of the present invention to provide compounds which widen the spectrum of the pesticides in various aspects.

The object, and further objects which are not stated explicitly but can be discerned or derived from the connections discussed herein, are achieved by compounds of the formula (I)

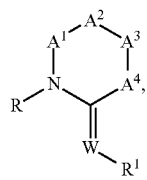
(I)

in which the structural unit of the formula

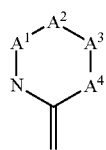

represents a radical A from the group consisting of

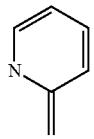
A-1

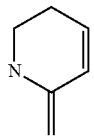
A-2

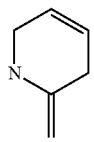
A-3

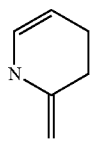
A-4

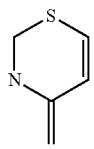
A-5

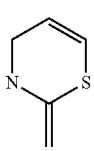
A-6

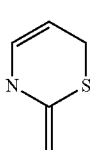
A-7

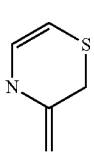
A-8

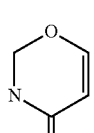
A-9

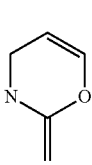
A-10

A-11 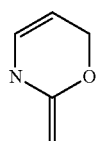

A-12 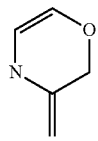

A-13 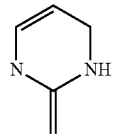

A-14 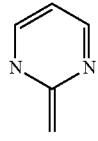

A-15 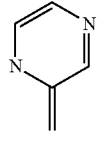

A-16 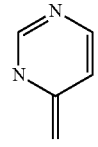

A-17 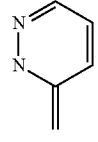

A-18 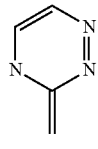

A-19 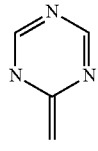

A-20 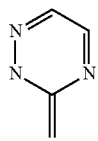

A-21 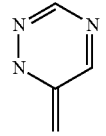

A-22 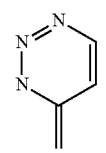

A-23 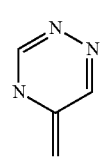

where these radicals carry m substituents X,

X represents a radical from the group consisting of halogen, cyano (CN), nitro, alkyl, alkoxy, alkylthio, alkylsulphinyl, alkylsulphonyl, haloalkyl, haloalkoxy, haloalkylthio, haloalkylsulphonyl, alkoxycarbonyl, alkylcarbonyl and cycloalkylcarbonyl, m represents a number from the group consisting of 0, 1 and 2, R represents a radical B from the group consisting of B-1 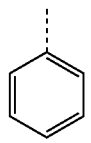

B-2 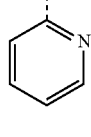

B-3 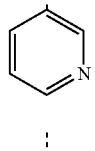

B-4 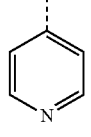

B-5 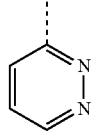

-continued

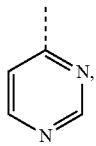 B-6

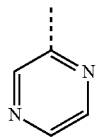 B-7

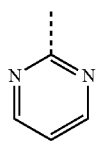 B-8

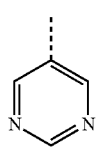 B-9

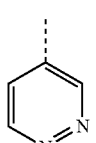 B-10

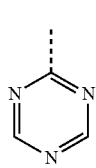 B-11

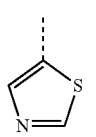 B-12

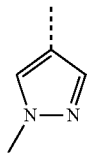 B-13

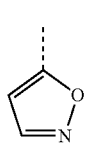 B-14

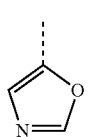 B-15

-continued

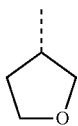 B-16 where these radicals carry n substituents Y and the dashed line represents the bond to the nitrogen atom in radical A, Y represents a radical from the group consisting of halogen, cyano, nitro, amino, alkyl, alkenyl, alkynyl, haloalkyl, alkoxy, haloalkoxy, alkylthio, haloalkylthio, alkylsulphinyl, haloalkylsulphinyl, alkylsulphonyl, haloalkylsulphonyl, alkoxy carbonyl, alkylcarbonyl, cycloalkylcarbonyl, alkylamino, dialkylamino, alkylaminosulphonyl, dialkylaminosulphonyl, alkylaminocarbonyl, dialkylaminocarbonyl, alkylcarbonylamino, alkoxyalkylcarbonylamino, haloalkylcarbonylamino and in each case optionally substituted aryl and hetaryl, n represents a number from the group consisting of 0, 1 and 2, W represents CH or N (nitrogen) and $R^1$ represents a radical from the group consisting of nitro, cyano, CS—$NH_2$ and CO—$CF_3$.

DETAILED DESCRIPTION OF A PREFERRED EMBODIMENT

Preference is given to compounds of the formula (I)

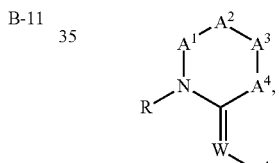

(I)

in which the structural unit of the formula

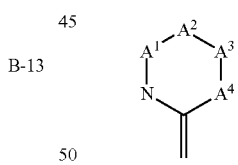

represents a radical A from the group consisting of

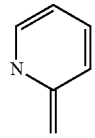 A-1

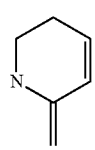 A-2

-continued

A-3

A-4

A-5

A-6

A-7

A-8

A-9

A-10

A-11

A-12

-continued

A-13

A-14

A-15

A-16

A-17

A-18

A-19

A-20

A-21

A-22

-continued

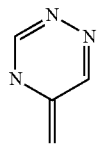
A-23 where these radicals carry m substituents X,

X represents a radical from the group consisting of halogen, cyano, nitro, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, halo-$C_1$-$C_4$-alkyl, halo-$C_1$-$C_4$-alkoxy, halo-$C_1$-$C_4$-alkylthio, halo-$C_1$-$C_4$-alkylsulphonyl, $C_1$-$C_4$-alkoxycarbonyl, $C_1$-$C_4$-alkylcarbonyl and $C_3$-$C_6$-cycloalkylcarbonyl, m represents a number from the group consisting of 0, 1 and 2, R represents a radical B from the group consisting of

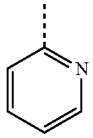
B-2

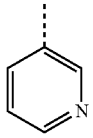
B-3

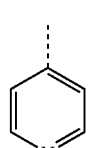
B-4

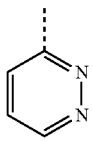
B-5

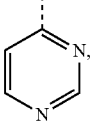
B-6

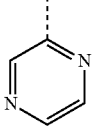
B-7

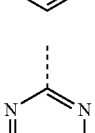
B-8

-continued

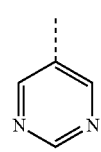
B-9

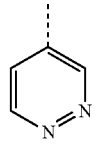
B-10

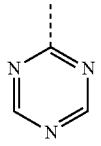
B-11

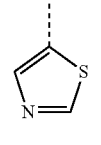
B-12

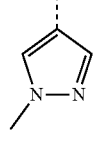
B-13

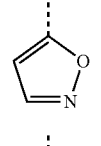
B-14

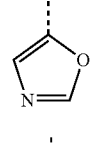
B-15

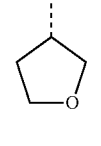
B-16 where these radicals carry n substituents Y and the dashed line represents the bond to the nitrogen atom in radical A, Y represents a radical from the group consisting of halogen, cyano, nitro, amino, $C_1$-$C_4$-alkyl, $C_2$-$C_4$-alkenyl, $C_2$-$C_4$-alkynyl, halo-$C_1$-$C_4$-alkyl, $C_1$-$C_4$-alkoxy, halo-$C_1$-$C_4$-alkoxy, $C_1$-$C_4$-alkylthio, halo-$C_1$-$C_4$-alkylthio, $C_1$-$C_4$-alkylsulphinyl, halo-$C_1$-$C_4$-alkylsulphinyl, $C_1$-$C_4$-alkylsulphonyl, halo-$C_1$-$C_4$-alkylsulphonyl, $C_1$-$C_4$-alkoxycarbonyl, $C_1$-$C_4$-alkylcarbonyl, $C_3$-$C_6$-cycloalkylcarbonyl, $C_1$-$C_4$-alkylamino, di-($C_1$-$C_4$-alkyl)amino, $C_1$-$C_4$-alkylaminosulphonyl, di-($C_1$-$C_4$-alkyl)aminosulphonyl, $C_1$-$C_4$-alkylaminocarbonyl, di-($C_1$-$C_4$-alkyl)aminocarbonyl, $C_1$-$C_4$-alkylcarbonylamino, $C_1$-$C_4$-alkoxy-$C_1$-$C_4$-alkylcarbonylamino, halo-$C_1$-$C_4$-alkylcarbonylamino, in each case optionally substituted aryl and 5- or 6-membered hetaryl and in the case of aryl and hetaryl in particular in each case optionally halogen-, cyano-, $C_1$-$C_4$-alkyl-, halo-$C_1$-$C_4$-alkyl-, $C_1$-$C_4$-alkoxy-, halo-$C_1$-$C_4$-alkoxy-, $C_1$-$C_4$-alkylthio-, halo-$C_1$-$C_4$-alkylthio-, $C_1$-$C_4$-alkylsulphinyl-, halo-$C_1$-$C_4$-alkylsulphinyl-, $C_1$-$C_4$-alkylsulphonyl- or halo-$C_1$-$C_4$-alkylsulphonyl-substituted phenyl and 5- or 6-membered hetaryl, where hetaryl is preferably selected from the group consisting of N-pyrazolyl, N-imidazolyl and N-1,2,4-triazolyl, n represents a number from the group consisting of 0, 1 and 2, W represents CH or N (nitrogen) and $R^1$ represents a radical from the group consisting of nitro, cyano, CS—$NH_2$ and CO—$CF_3$.

Particular preference is given to compounds of the formula (I)

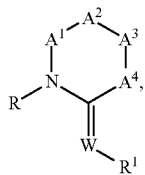
(I)

in which the structural unit of the formula

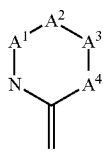

represents a radical A from the group consisting of

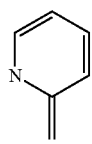
A-1

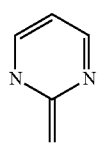
A-14

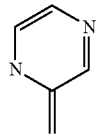
A-15

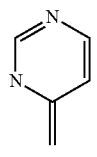
A-16

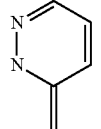
A-17

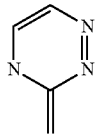
A-18

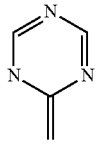
A-19

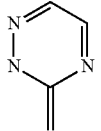
A-20

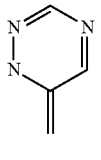
A-21

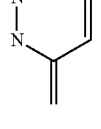
A-22

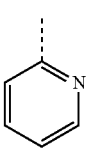
A-23 where these radicals carry m substituents X,

X represents a radical from the group consisting of hydrogen, halogen, cyano, $C_1$-$C_4$-alkyl, halo-$C_1$-$C_4$-alkyl, m represents a number from the group consisting of 0, 1 and 2, R represents a radical B from the group consisting of

B-2

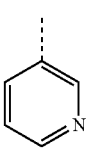
B-3

-continued

B-4
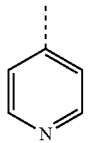

B-5
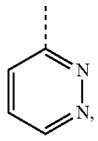

B-7
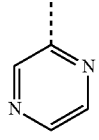

B-9
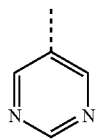

B-10
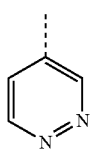

B-12
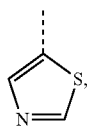

where these radicals carry n substituents Y and the dashed line represents the bond to the nitrogen atom in radical A, Y represents a radical from the group consisting of halogen, cyano, $C_1$-$C_4$-alkyl, $C_2$-$C_4$-alkenyl, $C_2$-$C_4$-alkynyl, halo-$C_1$-$C_4$-alkyl, halo-$C_1$-$C_4$-alkoxy, halo-$C_1$-$C_4$-alkylthio, $C_1$-$C_4$-alkylsulphinyl, halo-$C_1$-$C_4$-alkylsulphinyl, $C_1$-$C_4$-alkylsulphonyl, halo-$C_1$-$C_4$-alkylsulphonyl and 5-membered hetaryl which is optionally substituted by a substituent from the group consisting of halogen, cyano, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkylthio, halo-$C_1$-$C_4$-alkylthio, $C_1$-$C_4$-alkylsulphinyl, halo-$C_1$-$C_4$-alkylsulphinyl, $C_1$-$C_4$-alkylsulphonyl, halo-$C_1$-$C_4$-alkylsulphonyl, where hetaryl is, for example, N-pyrazolyl, N-imidazolyl or N-1,2,4-triazolyl, n represents a number from the group consisting of 0, 1 and 2, W represents N (nitrogen) and $R^1$ represents cyano or CO—$CF_3$.

Very particular preference is given to compounds of the formula (I)

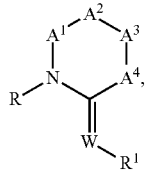

(I)

in which the structural unit of the formula

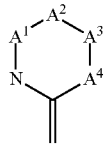

represents a radical A from the group consisting of

A-1
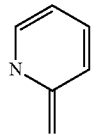

A-17
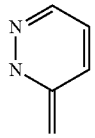

where these radicals carry m substituents X,

X represents a radical from the group consisting of fluorine, chlorine, bromine or iodine, cyano, methyl, ethyl, trifluoromethyl and difluoromethyl, m represents a number from the group consisting of 0, 1 and 2, R represents a radical from the group consisting of B-3
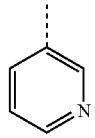

B-5
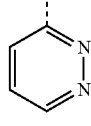

B-7
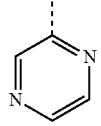

-continued

B-9

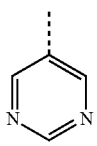

where these radicals carry n substituents Y and the dashed line represents the bond to the nitrogen atom in radical A, Y represents a radical from the group consisting of fluorine, chlorine, bromine or iodine, cyano, methyl, fluoromethyl, difluoromethyl, trifluoromethyl, difluorochloromethyl, difluorobromomethyl, 2,2-difluoroethyl, 2,2,2-trifluoroethyl, pentafluoroethyl, difluoromethyl, trifluoromethoxy, difluoromethylthio, trifluoromethylthio, difluoromethylsulphinyl, trifluoromethylsulphinyl, difluoromethylsulphonyl, trifluoromethylsulphonyl, N-triazolyl and N-pyrazolyl which is optionally substituted by a substituent from the group consisting of fluorine, chlorine, iodine, cyano, difluoromethyl, trifluoromethyl, difluoromethoxy, trifluoromethoxy and methylthio, n represents a number from the group consisting of 0, 1 and 2, W represents N (nitrogen) and $R^1$ represents cyano.

The radical definitions or elucidations given above in general terms or within preferred ranges apply correspondingly to the end products (including the compounds of the formulae (I-Aa) to (I-Oa) and (I-P-1) to (I-P-12) shown later), and to the starting materials and intermediates. These radical definitions can be combined with one another as desired, i.e. including combinations between the respective ranges of preference.

In a preferred embodiment, the invention relates to compounds of the formula (I-Aa)

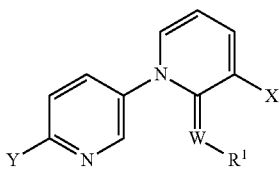

In a further preferred embodiment, the invention relates to compounds of the formula (I-Ba)

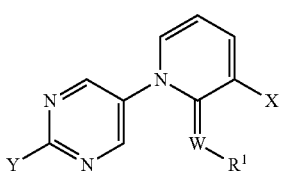

In a further preferred embodiment, the invention relates to compounds of the formula (I-Ca)

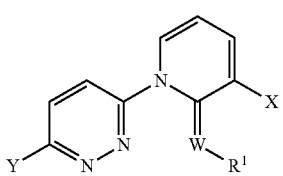

In a further preferred embodiment, the invention relates to compounds of the formula (I-Da)

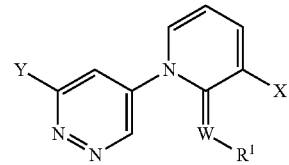

In a further preferred embodiment, the invention relates to compounds of the formula (I-Ea)

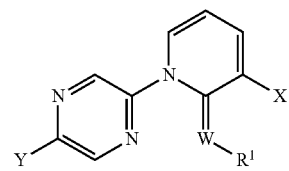

In a further preferred embodiment, the invention relates to compounds of the formula (I-Ab)

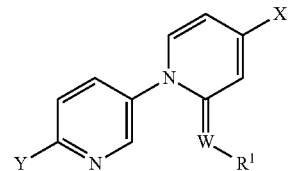

In a further preferred embodiment, the invention relates to compounds of the formula (I-Bb)

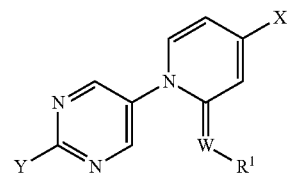

In a further preferred embodiment, the invention relates to compounds of the formula (I-Cb)

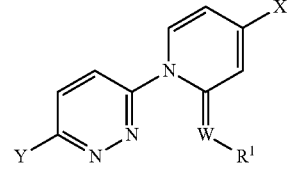

In a further preferred embodiment, the invention relates to compounds of the formula (I-Db)

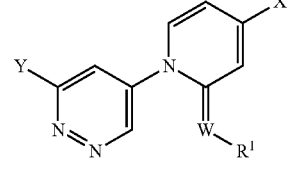

In a further preferred embodiment, the invention relates to compounds of the formula (I-Eb)

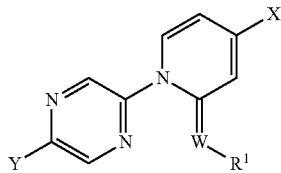

In a further preferred embodiment, the invention relates to compounds of the formula (I-Ac)

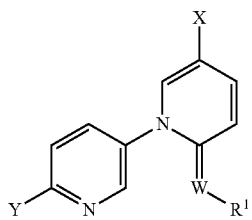

In a further preferred embodiment, the invention relates to compounds of the formula (I-Bc)

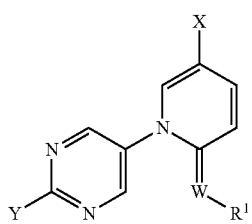

In a further preferred embodiment, the invention relates to compounds of the formula (I-Cc)

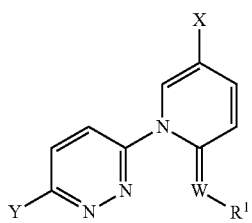

In a further preferred embodiment, the invention relates to compounds of the formula (I-Dc)

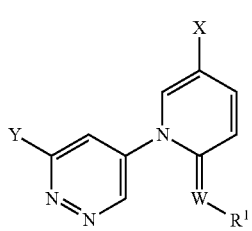

In a further preferred embodiment, the invention relates to compounds of the formula (I-Ec)

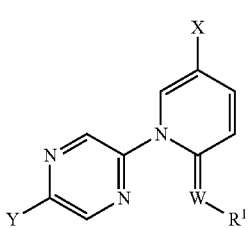

In a further preferred embodiment, the invention relates to compounds of the formula (I-Ad)

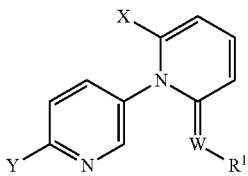

In a further preferred embodiment, the invention relates to compounds of the formula (I-Bd)

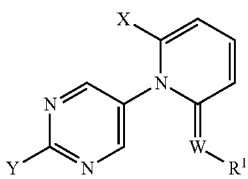

In a further preferred embodiment, the invention relates to compounds of the formula (I-Cd)

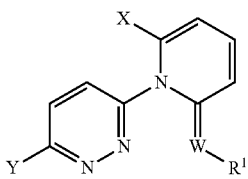

In a further preferred embodiment, the invention relates to compounds of the formula (I-Dd)

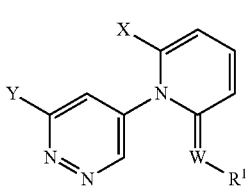

In a further preferred embodiment, the invention relates to compounds of the formula (I-Ed)

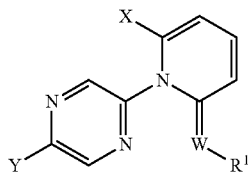

In a further preferred embodiment, the invention relates to compounds of the formula (I-Fa)

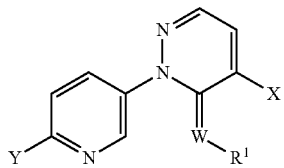

In a further preferred embodiment, the invention relates to compounds of the formula (I-Ga)

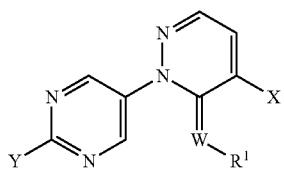

In a further preferred embodiment, the invention relates to compounds of the formula (I-Ha)

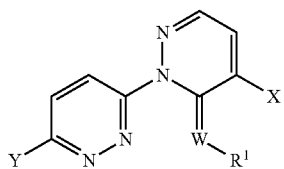

In a further preferred embodiment, the invention relates to compounds of the formula (I-Ia)

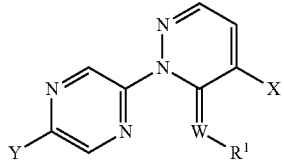

In a further preferred embodiment, the invention relates to compounds of the formula (I-Ja)

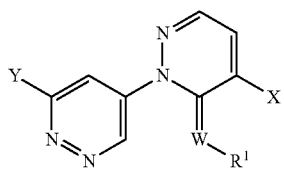

In a further preferred embodiment, the invention relates to compounds of the formula (I-Ka)

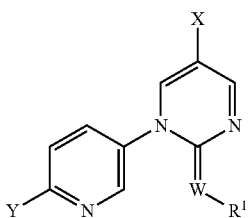

In a further preferred embodiment, the invention relates to compounds of the formula (I-La)

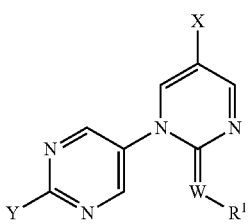

In a further preferred embodiment, the invention relates to compounds of the formula (I-Ma)

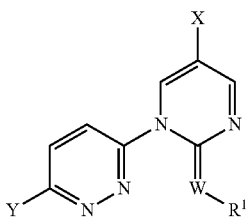

In a further preferred embodiment, the invention relates to compounds of the formula (I-Na)

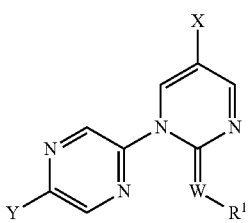

In a further preferred embodiment, the invention relates to compounds of the formula (I-Oa)

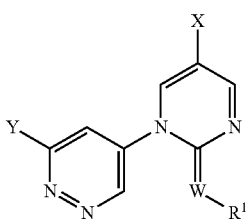

In the formulae (I-Aa) to (I-Oa), the variables W, X, Y and R¹ have the meanings mentioned further above.

In a further preferred embodiment, the invention relates to compounds of the formula (I-P-1)

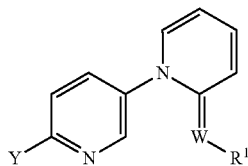

In a further preferred embodiment, the invention relates to compounds of the formula (I-P-2)

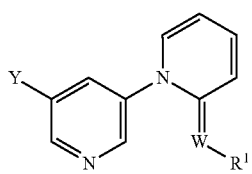

In a further preferred embodiment, the invention relates to compounds of the formula (I-P-3)

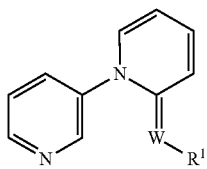

In a further preferred embodiment, the invention relates to compounds of the formula (I-P-4)

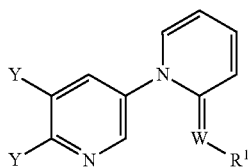

In a further preferred embodiment, the invention relates to compounds of the formula (I-P-5)

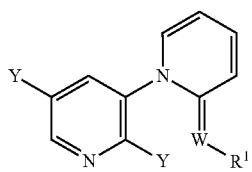

In a further preferred embodiment, the invention relates to compounds of the formula (I-P-6)

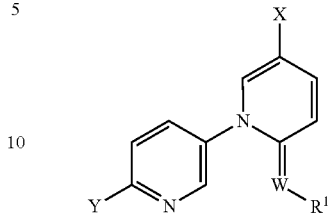

In a further preferred embodiment, the invention relates to compounds of the formula (I-P-7)

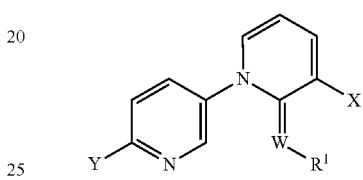

In a further preferred embodiment, the invention relates to compounds of the formula (I-P-8)

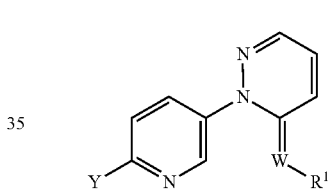

In a further preferred embodiment, the invention relates to compounds of the formula (I-P-9)

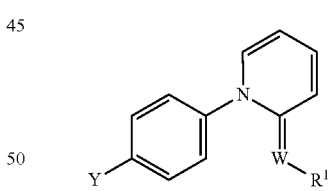

In a further preferred embodiment, the invention relates to compounds of the formula (I-P-10)

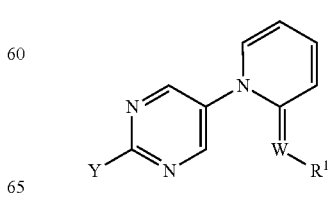

In a further preferred embodiment, the invention relates to compounds of the formula (I-P-11)

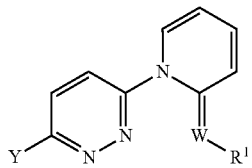

In a further preferred embodiment, the invention relates to compounds of the formula (I-P-12)

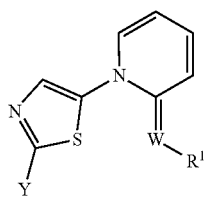

In the formulae (I-P-1) to (I-P-12), the variables W, X, Y and $R^1$ have the meanings mentioned further above.

The compounds of the formula (I) according to the invention and their acid addition salts and metal salt complexes are highly active, in particular in the control of animal pests including arthropods and in particular insects.

Suitable salts of the compounds of the formula (I) which may be mentioned are customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulphates, trihydrosulphates, or phosphates, salts with organic carboxylic acids or organic sulfonic acids, for example formates, acetates, trifluoroacetates, maleates, tartrates, methane sulphonates, benzene sulphonates or para-toluenesulphonates, salts with basic amino acids, for example arginates, aspartates or glutamates, and the like.

It has additionally been found that the compounds of the formula (I) can be prepared by the processes described below.

Compounds of the formula (I) in which the structural unit of the formula mentioned above represents a radical A-1, for example optionally substituted 2(1H)-pyridinylidene (e.g. $A^1$, $A^2$, $A^3$, $A^4$=CH) which is substituted in the N-position by a radical R can be prepared, for example, according to Reaction Scheme I using Processes A-C.

Reaction Scheme I

Process A

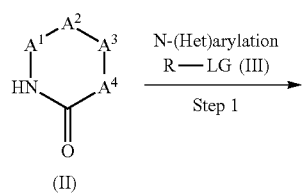

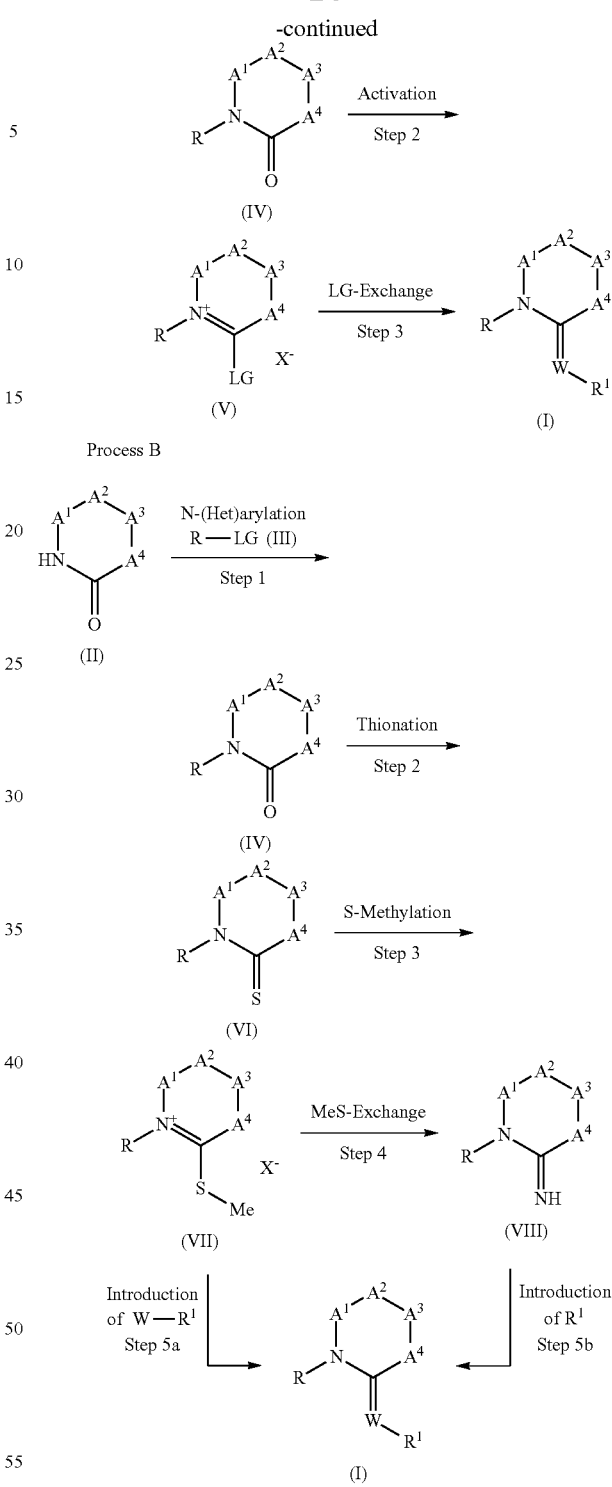

Process C

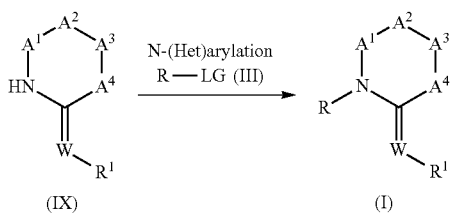

In Reaction Scheme I, $A^1$, $A^2$, $A^3$, $A^4$, R, $R^1$ and W have the meanings mentioned above.

For example, the compounds of the formula (I) in which the structural unit of the formula mentioned above represents a radical A-1, for example optionally substituted 2(1H)-pyridinylidene (e.g. $A^1$, $A^2$, $A^3$, $A^4$=CH), can be obtained from the compounds of the formula (II).

Process A

According to Process A, the compounds of the formula (II) can be reacted in an N-alkylation reaction with appropriate halogenated heterocycles or aromatic compounds of the formula (III) in the presence of catalysts and basic reaction auxiliaries in a first reaction step to give compounds of the formula (IV) which are then reacted in a second reaction step in the presence of a suitable halogenating agent, for example phosphoryl chloride, with formation of the activated compounds (V) which are then converted in a third reaction step into the compounds of the formula (I) in which $A^1$, $A^2$, $A^3$, $A^4$, R and W have the meanings mentioned above and $R^1$ represents cyano and W represents nitrogen (i.e. =W—$R^1$ represents the group =N—CN).

If, in Process A for the preparation of the compounds of the formula (I) according to Method A, the compound of the formula (II) employed is the 2(1H)-pyridinone ($A^1$, $A^2$, $A^3$, $A^4$=CH) and the compound of the formula (III) is the 5-bromo-2-trifluoromethylpyridine (R=6-trifluoromethylpyridin-3-yl; LG=Br), initially the 6'-trifluoromethyl-[1 (2H),3'-bipyridin]-2-one (R=6-trifluoromethylpyridin-3-yl; $A^1$, $A^2$, $A^3$, $A^4$=CH) of the formula (IV) is formed. Subsequent activation (Step 2) with phosphoryl chloride then leads to the 2-chloro-1-(6-trifluoromethylpyridin-3-yl)pyridinium chloride (V) which, in the third reaction step, reacts, for example, with cyanamide to give the [1-[6-trifluoromethylpyridin-3-yl]-2(1H)-pyridinylidene]cyanamide (R=6-trifluoromethylpyridin-3-yl; $A^1$, $A^2$, $A^3$, $A^4$=CH; W=N, $R^1$=CN) of the formula (I) (cf., for example, Preparation Examples 1, 13-15 and 18-23 in Table 3).

According to the invention, the activation (Step 2) can also be carried out with other acid halides, for example with phosphoryl bromide. In this case, the corresponding substituted pyridinium bromides (V) are formed which, in the third reaction step, can be converted for example with cyanamide into the compounds of the formula (I) (cf., for example, Preparation Example 2, Step 2).

In Process A for the preparation of the compounds of the formula (I), it is also possible to employ, as compound of the formula (II), the 2(1H)-pyridinone ($A^1$, $A^2$, $A^3$, $A^4$=CH) and as compound of the formula (III), for example, the 6-methyl-3-pyridinylboronic acid (R=6-methylpyridin-3-yl; LG=B($OH)_2$). In this case, the compound of the formula (IV) formed is the 1-(6-methyl-3-pyridinyl-2(1H)-pyridone (R=6-methylpyridin-3-yl; $A^1$, $A^2$, $A^3$, $A^4$=CH) (cf., for example, preparation examples for boronic acid couplings: (IV-3) via Variant B and also (IV-12), (IV-14)-(IV-16) and (IV-22).

Some of the compounds of the formula (II) are known and commercially available, for example 2(1H)-pyridinone ($A^1$, $A^2$, $A^3$, $A^4$=CH), 5-fluoro-2(1H)-pyridinone ($A^1$, $A^3$, $A^4$=CH; $A^2$=C—F), 5-trifluoromethyl-2(1H)-pyridinone ($A^1$, $A^3$, $A^4$=CH; $A^2$=C—$CF_3$), 4-fluoro-2(1H)-pyridinone ($A^1$, $A^2$, $A^4$=CH; $A^3$=C—F), 4-trifluoromethyl-2(1H)-pyridinone ($A^1$, $A^2$, $A^4$=CH; $A^3$=C—$CF_3$) [cf. A-1]; 5,6-dihydro-2(1H)-pyridone ($A^1$, $A^2$=$CH_2$, $A^3$, $A^4$=CH) [cf. A-2]; 3,6-dihydro-2(1H)-pyridone ($A^1$, $A^4$=$CH_2$, $A^2$, $A^4$=CH) [cf. A-3]; 3,4-dihydro-2(1H)-pyridone ($A^1$, $A^2$=C—H, $A^3$, $A^4$=$CH_2$) [cf. A-4]; 2H—1,4-thiazin-3(4H)-one ($A^1$, $A^2$=CH, $A^3$=S, $A^4$=$CH_2$) [cf. A-8]; 2,3-dihydro-4H-1,3-oxazin-4-one ($A^1$=$CH_2$, $A^2$=O, $A^3$, $A^4$=C—H) [cf. A-9]; 3,4-dihydro-2(1H)-pyrimidinone ($A^1$, $A^2$=CH, $A^3$=$CH_2$, $A^4$=NH) [cf. A-13]; 2(1H)-pyrazinone ($A^1$, $A^2$, $A^4$=CH, $A^3$=N) [cf. A-14]; 4(3H)-pyrimidinone ($A^1$, $A^3$, $A^4$=CH, $A^2$=N) [cf. A-15]; 3(2H)-pyridazinone ($A^1$=N, $A^2$, $A^3$, $A^4$=CH) [cf. A-16], or they can be obtained by preparation processes known in principle (for 3,4-dihydro-2H-1,3-thiazin-2-one ($A^1$=$CH_2$, $A^2$, $A^3$=CH; $A^4$=S) (SU1253977 A1) [cf. A-6]; 1,2,4-triazin-3(2H)-one ($A^1$, $A^2$=CH, $A^3$, $A^4$=N) (EP35333 A2) [cf. A-17]; 1,3,5-triazin-2(1H)-one ($A^1$, $A^3$=CH, $A^2$, $A^4$=N) (WO 2015/042266 A1) [cf. A-18]; 1,2,4-triazin-3(2H)-one ($A^1$, $A^4$=N, $A^2$, $A^3$=CH) (EP35333 A2 [cf. A-19]; 1,2,4-triazin-6(1H)-one ($A^1$, $A^3$=N, $A^2$, $A^4$=CH) (C. W. Lindsley, M. E. Layton, Science of Synthesis 17, 357-447, 2004) [cf. A-20] and 1,2,4-triazin-5(4H)-one ($A^1$, $A^4$=CH, $A^2$, $A^3$=N) (A. K. Mazitova et al., *Bashkirskii Khim. Zhurnal* 6(4), 4-9, 1999) [cf. A-22].

Some of the compounds of the formula (III) in which R has the meaning mentioned above and LG represents a nucleofugic leaving group LG optionally generated in-situ are known and commercially available or can be obtained by preparation processes known in principle.

For example, the compounds (B-1) to (B-16) having a suitable leaving group (LG=B$(OH)_2$) or (hetero)arylboronic ester (LG=B$(OR)_2$) can be reacted with the appropriate compounds of the formula (II) according to known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004) in the presence of suitable catalysts from the group of the transition metal salts to give compounds of the formula (I).

Some of the compounds (B-1) to (B-16) having a suitable leaving group (LG=B$(OH)_2$) or (hetero)arylboronic ester (LG=B$(OR)_2$) are commercially available, known or can be prepared by known methods: for example 2-phenyl-4-(4,4,5,5-tetramethyl-1,3,2-dioxaborolan-2-yl)-oxazole [(B-1), LG=B$(OCMe_2)_2$, WO 2010/094755]; pyridin-3-ylboronic acid [(B-2), LG=B$(OH)_2$, WO 2013/186089]; pyrazin-3-ylboronic acid [(B-5), LG=B$(OH)_2$, commercially available from: UORSY Building blocks Library]; pyridazin-4-ylboronic acid [(B-10), LG=B$(OH)_2$, commercially available from: FCH Group Reagents for Synthesis]; 1,3,5-triazin-2-ylboronic acid [(B-11), LG=B$(OH)_2$, *Korean Kongkae Taeho Kongbo* (2011), KR 2011/079401]; 2-chloro-5-(4,4,5,5-tetramethyl-1,3,2-dioxaborolan-2-yl)thiazole [(B-12), LG=B$(OCMe_2)_2$, commercially available from: FCH Group Reagents for Synthesis]; 1-(methyl-1H-pyrazol-4)boronic acid [(B-13), LG=B$(OH)_2$, WO 2009/155527]; (1,2-oxazol-5-yl)boronic acid [(B-14), LG=B$(OH)_2$, commercially available from: FCH Group Reagents for Synthesis]; (1,3-oxazol-5-yl)boronic acid [(B-15), LG=B$(OH)_2$, commercially available from: FCH Group Reagents for Synthesis]; rac-tetrahydro-3-furanylboronic acid [(B-16), LG=B$(OH)_2$, commercially available from: ABCR].

Some of the compounds of the formula (IV) in which $A^1$, $A^2$, $A^3$, $A^4$ and R have the meanings mentioned above are known and commercially available (cf., for example, for R=6-bromopyridin-3-yl (A-1; $A^1$-$A^4$=H, UORSY Building Blocks Library), or they can be obtained according to Step 1 of the Preparation Process A mentioned from the compounds of the formula (II) by N-(het)arylation, cf., for example, for R=pyridin-3-yl (A-1; $A^1$-$A^4$=CH) the copper-catalysed coupling reaction of pyridin-2-(1H)-one with aryl (hetaryl) halides (K. J. Filipinski et al., *Tetrahedron Lett.* 2006, 47, 7677-7680), according to Buchwald's protocol (Ch. S. Li, D. D. Dixon, *Tetrahedron Lett.* 2004, 45, 4257-

4260) or according to the improved Ullmann-Ukita-Buchwald-Li conditions for a copper-catalysed reaction (cf., for example, Po-Shih Wang et al., *Tetrahedron* 2005, 61, 2931-2939 and the methods employed in Preparation Examples 1, 13-15 and 18-23 in Table 3).

The compounds of the formula (IV) can then be converted according to Step 2 of Preparation Process A using suitable activating agents, for example with acid halides of inorganic acids such as sulphuryl chloride, phosphoryl chloride, phosphorus pentachloride, phosphoryl bromide, phosphorus pentabromide or with acid halides of organic acids such as oxalyl chloride into the compounds of the formula (V) in which $A^1$, $A^2$, $A^3$, $A^4$ and R have the meanings mentioned above and $X^-$ represents an appropriate halide anion, for example chloride or bromide, and LG represents a nucleofugic leaving group LG optionally generated in-situ (cf. also Preparation Examples 1 (LG=Cl) and 2 (LG=Br), in each case Step 2).

By exchange of the leaving group LG in Reaction Step 3, for example using cyanamide, the compounds of the formula (I) in which $A^1$, $A^2$, $A^3$, $A^4$ and R have the meanings mentioned above and $R^1$ represents cyano and W represents nitrogen (i.e. =W—$R^1$ for the group =N—CN) are formed (cf. J. A. Vega et al., *Tetrahedron* 1999, 55, 2317-2326 and Preparation Examples 1, 13-15 and 18-23 in Table 3).
Process B Using Process B, the compounds of the formula (IV) in which $A^1$, $A^2$, $A^3$, $A^4$ and R have the meanings mentioned above and which can be obtained by the abovementioned Process A (Step 1) can be converted by a thionation reaction (Step 2) into compounds of the formula (VI). Subsequent S-methylation then affords compounds of the formula (VII). In this case, the S-methyl group can, as nucleofugic leaving group LG, be exchanged in Step 4, for example for ammonia with formation of the compounds of the formula (VIII) in which $R^1$ represents hydrogen and W represents nitrogen (i.e. =W—$R^1$ represents the group =N—H). In this manner, the compounds of the formula (I) in which =W—$R^1$ represents the group =N—CN can be obtained in a simple manner by introduction of the substituent $R^1$=CN with cyanogen bromide or exchange of the nucleofugic leaving group LG=S-methyl (SMe) using cyanamide or, for example, using the sodium salt of the cyanamide (cf., for example, Preparation Examples 1, 24 and 25).

If, in Process B for the preparation of the compounds of the formula (I), the compound of the formula (II) employed is the 2(1H)-pyridinone ($A^1$, $A^2$, $A^3$, $A^4$=CH) and the compound of the formula (III) is the 5-bromo-2-methylpyridine (R=6-methylpyridin-3-yl; LG=Br), initially the 6'-methyl-[1(2H),3'-bipyridin]-2-one (R=6-methylpyridin-3-yl; $A^1$, $A^2$, $A^3$, $A^4$=CH) of the formula (IV) is formed. Subsequent thionation (Step 2) using diphosphorus pentasulphide then leads to 6'-methyl-[1(2H),3'-bipyridine]-2-thione of the formula (VI) which is then S-methylated with methyl iodide in a third reaction step with formation of [1-[6-methylpyridin-3-yl]-2-(methylthio)pyridinium iodide of the formula (VII). Exchange of the nucleofugic leaving group LG=methylthio (SMe) with cyanamide then affords the [1-[6-methylpyridin-3-yl]-2(1H)-pyridinylidene]cyanamide of the formula (I) (R=6-methylpyridin-3-yl; $A^1$, $A^2$, $A^3$, $A^4$=CH; W=N, $R^1$=CN) (cf., for example, M. C. Christensen et al. *Synthesis* 1980, 5, 405-407 and Preparation Example 2).

Some of the compounds of the formula (VI) are known (cf., for example, for R=phenyl (A-1; $A^1$-$A^4$=CH, WO 2014/184808); R=1-(4-iodophenyl) (A-1; $A^1$-$A^4$=CH, US 2007/0259924 A1)), and commercially available (cf., for example, for R=4-nitrophenyl (A-1; $A^1$-$A^4$=CH, FCH Group Reagents for Synthesis)) or can be obtained according to Step 2 of Preparation Process B from the compounds of the formula (IV) by thionation of the carbonyl group (cf., for example, for R=phenyl (A-1; $A^1$-$A^4$=CH, J. G. Sosnicki, *Tetrahedron* 2007, 63, 11862-11877)).

A large number of different thionating agents (sulphurizing agents) has been described in the literature, for example hydrogen sulphide ($H_2S$), hydrogen sulphide/hydrogen chloride ($H_2S$/HCl), hydrogen persulphide/hydrogen chloride ($H_2S_2$/HCl), di(diethylaluminium) sulphide [($Et_2Al)_2S$], polymeric ethylaluminium sulphide [$(EtAlS)_n$], silicon disulphide ($SiS_2$), diboron trisulphide ($B_2S_3$), phosphorus pentachloride/dialuminium trisulphide/sodium sulphate ($PCl_5/Al_2S_3/Na_2SO_4$), sodium sulphide/sulphuric acid ($Na_2S/H_2SO_4$), diphosphorus pentasulphide ($P_2S_5$), diphosphorus pentasulphide/pyridine ($P_2S_5$/Py), diethylthiocarbamoyl chloride, diphosphorus pentasulphide/triethylamine ($P_2S_5/NEt_3$), diphosphorus pentasulphide/n-butyllithium ($P_2S_5$/n-BuLi), diphosphorus pentasulphide/sodium bicarbonate ($P_2S_5/NaHCO_3$; "Scheeren's reagent", formation of $Na^{2+}[P_4S_{10}O]^{2-}$), diphosphorus pentasulphide/methanol ($P_2S_5$/MeOH), SCN—CO—OEt, $PSCl_x(NMe_2)_{3-x}$ (X=0-3), bis(tricyclohexyltin) sulphide/boron trihalide [$(C_6H_{11})_3Sn$] $S_2+BX_3$ (X=Cl, F) (cf. EP 0280867 A1), bis(1,5-cyclooctanediylboryl) sulphide [$(9-BBN)_2S$] as sulphurizing agent or as phosphorus pentasulphide substitute, 2,4-bis(methylthio)-1,3,2,4-dithiadiphosphetane 2,4-disulphide "Davy reagent methyl" (DR-Me), 2,4-bis(ethylthio)-1,3,2,4-dithiadiphosphetan 2,4-disulphide "Davy reagent p-tolyl or Heimgartner reagent" (DR-T), 2,4-bis-(4-phenoxyphenyl)-2,4-dithioxo-1,3,2,4-dithiaphosphetane "Belleau's reagent" (BR), 2,4-bis-(4-phenylthiophenyl)-2,4-dithioxo-1,3,2,4-dithiaphosphetane, 2,4-bis-(4-methoxyphenyl)-2,4-dithioxo-1,3,2,4-dithiaphosphetane "Lawesson's reagent" (LR) (cf. WO 98/43965 A1 and the literature cited therein).

Preferred thionating agents (sulphurizing agents) are diphosphorus pentasulphide ($P_2S_5$), diphosphorus pentasulphide/pyridine ($P_2S_5$/Py), 2,4-bis-(4-phenoxyphenyl)-2,4-dithioxo-1,3,2,4-dithiaphosphetane "Belleau's reagent" (BR) or 2,4-bis-(4-methoxyphenyl)-2,4-dithioxo-1,3,2,4-dithiaphosphetane "Lawesson's reagent" (LR).
Process C Alternatively, according to Process C, the compounds of the formula (IX) in which $A^1$, $A^2$, $A^3$, $A^4$, W and $R^1$ have the meanings mentioned above can be reacted with compounds of the formula (III) in which R has the meaning mentioned above and LG represents a nucleofugic leaving group LG which is optionally generated in situ, to give compounds of formula (I) (cf. Preparation Examples 5 to 7).

Some of the compounds of the formula (IX) in which $A^1$, $A^2$, $A^3$, $A^4$, R and =W—$R^1$ have the meanings mentioned above are known (cf., for example, 1,1,1-trifluoro-3-(2-pyridinyl)-2-propanone: $A^1$-$A^4$=CH and =W—$R^1$ represents the group =CH—CO—$CF_3$; WO 2005/030736 A1; UORSY Building Blocks Library; N-2-pyridinylcyanamide: $A^1$-$A^4$=CH and =W—$R^1$ represents the group =N—CN; EP 38161 A1; 3-pyridazinylcyanamide: =N, $A^2$-$A^4$=CH and =W—$R^1$ represents the group =N—CN; UORSY Building Blocks Library; 2-pyrimidinylcyanamide: $A^1$-$A^3$=CH, $A^4$=N and =W—$R^1$ represents the group =N—CN; DE 3517844 A1; 2,2,2-trifluoro-N-2-pyridinylacetamide: $A^1$-$A^4$=CH and =W—$R^1$ represents the group =N—CO—$CF_3$; EP 2634174 A2; 2,2,2-trifluoro-N-2-pyrimidinylacetamide: $A^1$-$A^3$=CH, $A^4$=N and =W—$R^1$ represents the group =N—CO—$CF_3$; WO 2002/004447 A1; N-nitro-2-pyridinamine $A^1$-$A^4$=CH and =W—$R^1$ represents the group =N—NO$_2$; Apichemical (Shanghai) Product List; N-nitro-2-pyrimidinamine A$^1$-A$^3$=CH, A$^4$=N and =W—R$^1$ represents the group =N—NO$_2$; Shanghai Race Chemical Product List.

The compounds of the formula (VIII) in which A$^1$, A$^2$, A$^3$, A$^4$ and R have the meanings mentioned above are likewise suitable for the synthesis of compounds of the formulae (Ia) (R$^1$=COCF$_3$), (Ib) (R$^1$=CN) and (Ic) (R1=NO$_2$) in which A$^1$, A$^2$, A$^3$, A$^4$ and R have the meanings mentioned above (cf. Reaction Scheme II).

Reaction Scheme II

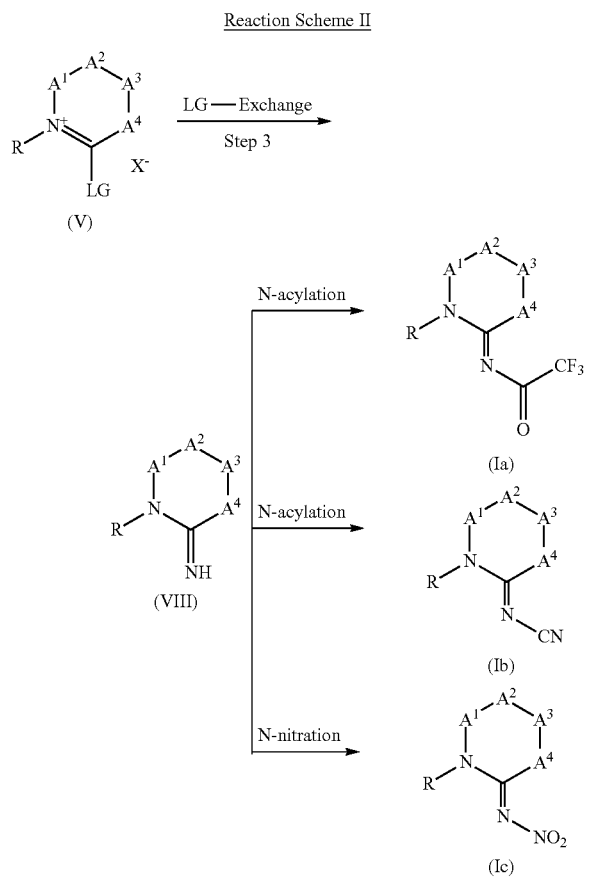

For example, compounds of the formula (Ia) (R$^1$=COCF$_3$) can be obtained by an N-acylation reaction with trifluoroacetic anhydride or trifluoroacetyl chloride in a suitable diluent and in the presence of a basic auxiliary (cf., for example, Preparation Examples 7 and 9 to 11, Table 3).

Compounds of the formula (Ib) (R$^1$=CN) can be obtained by an N-acylation reaction with cyanogen bromide in a suitable diluent and in the presence of a basic auxiliary (cf. Preparation Example 8).

In addition, compounds of the formula (Ic) (R$^1$=NO$_2$) can be obtained by an N-nitration reaction with nitrating agent (e.g. conc. sulphuric acid/90-95% strength nitric acid) (cf. A. Taurins, S. J. Viron, Can. J. Chem. 1953, 31, 1048-1053).

Compounds of the formula (IV) in which A$^1$, A$^2$, A$^3$ and R have the meanings mentioned above and A$^4$ represents CH can be converted in a halogenation reaction with suitable halogenating agents into compounds of the formula (IV) in which A$^1$, A$^2$, A$^3$ and R have the meanings mentioned above and A$^4$ represents C-Hal (cf. Reaction Scheme III and Preparation Example IV-5).

Reaction Scheme III

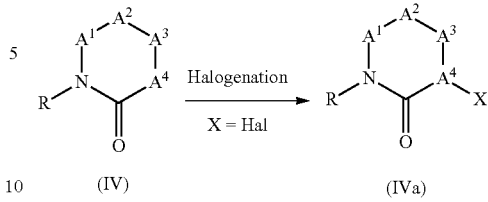

Suitable halogenating agents are, for example, fluorinating agents such as (diethylamino)sulphur trifluoride (DAST), fluorooxytrifluoromethane (CF$_3$OF) or 1-chloromethyl-4-fluoro-1,4-diazoniabicyclo[2.2.2]octane bis(tetrafluoroborate) (Selectfluor) (cf. also P. T. Nyffeler et al., Angew. Chem. 2005, 117, 196-217), chlorinating agents such as N-chlorosuccinimide (NCS), brominating agents such as N-bromosuccinimide (NBS) and iodinating agents such as N-iodosuccinimide (NIS).

Preference is given to using 1-chloromethyl-4-fluoro-1,4-diazoniabicyclo[2.2.2]octane bis(tetrafluoroborate) (Selectfluor) and halogenated succinimides such as N-chlorosuccinimide (NCS), N-bromosuccinimide (NBS) and N-iodosuccinimide (NIS).

Compounds of the formula (IVc) in which A$^1$, A$^2$, A$^3$ have the meanings mentioned above, R represents a radical from the group consisting of B-3, B-5 to B-7, B-9, B-12 or B-15 and Y represents a substituted heterocycle, for example N-pyrazolyl or N-1,2,4-triazolyl, can be obtained in a nucleophilic substitution from compounds of the formula (IVb) in which A$^1$, A$^2$, A$^3$ and R have the meanings mentioned above and Y represents halogen.

Reaction scheme IV describes the preparation of compounds of the formula (IVc) in which A$^1$, A$^2$, A$^3$ have the meanings mentioned above, R represents pyridin-3-yl (radical B-3) and Y represents an optionally substituted heterocycle, for example N-pyrazolyl or N-1,2,4-triazolyl.

Reaction Scheme IV

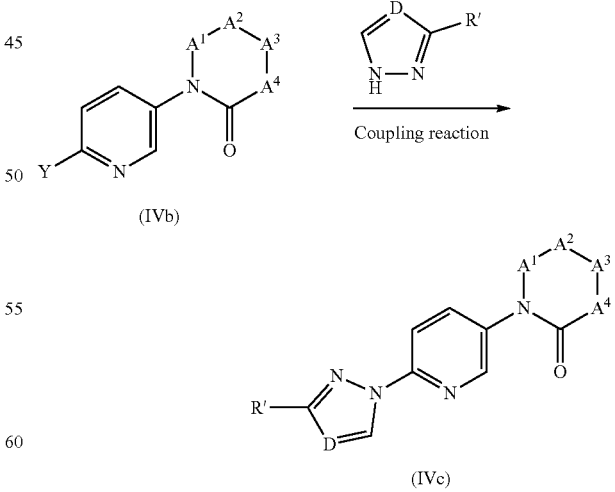

The coupling reaction of compounds of the formula (IVb) with optionally R'-substituted nitrogen heterocycles with formation of the compounds of the formula (IVc) is preferably carried out in the presence of copper(I) iodide and N,N-dimethylcyclohexane-1,2-diamine in suitable solvents or diluents (cf. also the Preparation Examples IV-29 where D=N, R'=Cl and IV-30 where D=CH, R'=CF$_3$).

Compounds of the formula (IVd) in which A$^1$, A$^2$, A$^3$ have the meanings mentioned above, R represents a radical from the group consisting of B-3, B-5 to B-7, B-9, B-12 or B-15 and Y represents a perfluorinated alkyl radical, for example pentafluoroethyl, heptafluoropropyl or heptafluoro-iso-propyl, can be obtained in a coupling reaction from compounds of the formula (IVb) in which A$^1$, A$^2$, A$^3$ and R have the meanings mentioned above and Y represents halogen.

Reaction scheme V describes the preparation of compounds of the formula (IVd) in which A$^1$, A$^2$, A$^3$ have the meanings mentioned above, R represents pyridin-3-yl (radical B-3) and Y represents a perfluorinated alkyl radical (Rf), for example pentafluoroethyl, heptafluoropropyl or heptafluoro-iso-propyl.

Reaction Scheme V

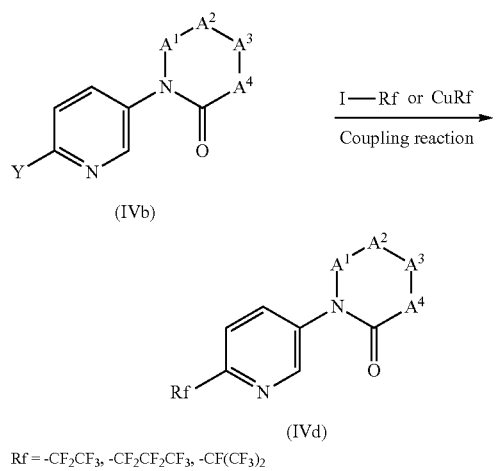

Rf = -CF$_2$CF$_3$, -CF$_2$CF$_2$CF$_3$, -CF(CF$_3$)$_2$

The coupling reaction of compounds of the formula (IVb) with perfluorinated alkyl iodides (e.g. Rf=CF$_2$CF$_2$CF$_3$, CF(CF$_3$)$_2$) with formation of the compounds of the formula (IVd) is preferably carried out in the presence of copper powder in suitable solvents or diluents (cf. also the Preparation Examples IV-31 and IV-32).

Alternatively, the coupling reaction of compounds of the formula (IVb) can be carried out with perfluorinated alkylcopper (e.g. pentafluoroethylcopper, Rf=CF$_2$CF$_3$) with formation of the compounds of the formula (IVd) in suitable solvents or diluents (cf. Preparation Example IV-33 and A. Lishchynskyi, V. V. Grushin, *J. Am. Chem. Soc.* 135, 12584, 2013).

According to processes A and B, the preparation of compounds of the formula (IV) in which A$^1$ to A$^4$ and R have the meanings mentioned above is preferably carried out in the presence of copper(I) iodide or copper(I) acetate, reaction auxiliaries and in suitable solvents or diluents.

Suitable reaction auxiliaries used for preparing the compounds of the formula (IV) are basic reaction auxiliaries.

Examples which may be mentioned are the hydroxides, hydrides, oxides and carbonates of lithium, sodium, potassium, magnesium, calcium and barium, furthermore further basic compounds such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N',N'-tetraethylenediamine, quinoxaline, N-propyldiisopropylamine, N-ethyldiisopropylamine ("Hünig's Base"), N,N'-dimethylcyclohexylamine, 2,6-lutidine, 2,4-lutidine or triethylenediamine.

Suitable for use as basic reaction auxiliaries for carrying out the Processes A and B according to Reaction Scheme I are all suitable acid binders, for example alkali metal carbonates or amines.

Preference is given to using potassium carbonate, trans-N,N'-dimethylcyclohexane-1,2-diamine or pyridine.

Suitable solvents or diluents include all inert organic solvents, for example aliphatic or aromatic hydrocarbons (such as petroleum ether, toluene), halogenated hydrocarbons (such as chlorotoluene, dichloromethane, chloroform, 1,2-dichloroethane), ethers (such as diethyl ether, dioxane, tetrahydrofuran, 1,2-dimethoxyethane), esters (such as ethyl acetate or methyl acetate), nitrohydrocarbons (such as nitromethane, nitroethane, nitrobenzene), nitriles (such as acetonitrile, benzonitrile), amides (such as N,N-dimethylformamide, N,N-dimethylacetamide, N-methylformanilide, N-methylpyrrolidone, hexamethylphosphoric triamide), and also dimethyl sulphoxide or water or mixtures of the solvents mentioned.

Preference is given to using, as solvents, halogenated hydrocarbons such as dichloromethane or 1,2-dichloroethane and amides such as N,N-dimethylformamide.

According to Process A, the preparation of compounds of the formula (V) in which A$^1$ to A$^4$ and R have the meanings mentioned above is preferably carried out in the presence of inorganic acid halides, a catalytic amount of a basic reaction auxiliary and in the presence of suitable solvents or diluents.

Preference is given to using, as solvents, phosphoryl halides, halogenated hydrocarbons such as dichloromethane or 1,2-dichloroethane and amides such as N,N-dimethylformamide.

According to Process A, the compounds of the formula (I) in which A$^1$ to A$^4$ and R have the meanings mentioned above and =W—R$^1$ represents the group =N—CN are preferably prepared in the presence of a basic reaction auxiliary and in the presence of suitable solvents or diluents.

The basic reaction auxiliaries and solvents or diluents employed are preferably potassium carbonate and nitriles such as acetonitrile, respectively.

According to Process B, the preparation of compounds of the formula (VI) in which A$^1$ to A$^4$ and R have the meanings mentioned above is preferably carried out in the presence of a thionating agent (sulphurizing agents) and in the presence of a basic reaction auxiliary and of suitable solvents or diluents.

The thionating agents (sulphurizing agents), basic reaction auxiliaries and solvents or diluents used are preferably diphosphorus pentasulphide (P$_2$S$_5$), sodium bicarbonate and 1,4-dioxane, respectively.

According to Process B, the preparation of compounds of the formula (VII) in which A$^1$ to A$^4$ and R have the meanings mentioned above is preferably carried out in the presence of a suitable S-alkylating agent and in the presence of a suitable solvent or diluent.

The S-alkylating agent and solvents or diluents used are preferably methyl iodide and a nitrile, for example acetonitrile, respectively.

According to Process B, the compounds of the formula (I) in which $A^1$ to $A^4$ and R have the meanings mentioned above and =W—$R^1$ represents the group =N—CN are preferably prepared in the presence of a basic reaction auxiliary and in the presence of suitable solvents or diluents.

The basic reaction auxiliaries and solvents or diluents employed are preferably hydrazine hydrate and nitriles such as acetonitrile, respectively.

According to Process C, the preparation of the compounds of the formula (I) in which $A^1$ to $A^4$ and R have the meanings mentioned above is preferably carried out in the presence of copper(I) iodide, reaction auxiliaries and in suitable solvents or diluents.

The reaction auxiliaries and solvents or diluents employed are preferably potassium acetate and amides such as N,N-dimethylformamide, respectively.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" is understood as meaning the entirety of all measures, processes and procedures whose aim it is to prevent disorders—in particular infective diseases—and to serve to keep humans, animals and/or the environment healthy and/or to maintain cleanliness. According to the invention, this includes in particular measures for cleaning, disinfecting and sterilizing, for example, textiles or solid surfaces, mainly of glass, wood, concrete, porcelain, ceramic, plastic or else of metal(s), and keeping them clean of hygiene pests and/or their faeces. Excluded according to the invention are in this respect again processes for the surgical or therapeutic treatment of the human or animal body and diagnostic processes undertaken on the human or animal body.

The term "hygiene sector" thus includes all areas, technical fields and commercial utilizations in which such hygiene measures, processes and procedures are of importance, for example hygiene in kitchens, bakeries, airports, baths, swimming pools, shopping centres, hotels, hospitals, stables, etc.

Accordingly, the term "hygiene pest" is understood as meaning one or more animal pests whose presence in the hygiene sector is problematic, in particular for health reasons. Accordingly, the main aim is to minimize or prevent hygiene pests or contact therewith in the hygiene sector. This can be effected, in particular, by using a pesticide, where the agent can be employed both prophylactically and only in the case of infestation to control the pest. It is also possible to use agents which act by avoiding or reducing contact with the pest. Hygiene pests are, for example, the organisms mentioned below.

Thus, the term "hygiene protection" includes all actions which serve to maintain and/or improve such hygiene measures, processes and procedures.

The compounds of the formula (I) can preferably be used as pesticides. They are active against normally sensitive and resistant species and also against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa*;

from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloborerus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus* (=Hyperodes) spp., *Lixus* spp., *Luperodes* spp., *Luperomorpha xanthodera, Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Dermaptera, for example *Anisolabis maritime, Forficula auricularia, Labidura riparia*;

from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda*;

from the order of the Hemiptera, for example *Acizzia acaciaebaileyanae, Acizzia dodonaeae, Acizzia uncatoides, Acrida turrita, Acyrthosiphon* spp., for example *Acyrthosiphon pisum, Acrogonia* spp., *Aeneolamia* spp., *Agonoscena* spp., *Aleurocanthus* spp., *Aleurodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis*

*melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lopholeucaspis japonica, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Megacopta cribraria, Miridae, Monalonion atratum, Nezara* spp., for example *Nezara viridula, Nysius* spp., *Oebalus* spp., *Pentomidae, Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Camponotus* spp., *Dolichovespula* spp., *Diprion* spp., for example *Diprion similis, Hoplocampa* spp., for example *Hoplocampa cookei, Hoplocampa testudinea, Lasius* spp., *Linepithema* (*Iridiomyrmex*) *humile, Monomorium pharaonis, Paratrechina* spp., *Paravespula* spp., *Plagiolepis* spp., *Sirex* spp., *Solenopsis invicta, Tapinoma* spp., *Technomyrmex albipes, Urocerus* spp., *Vespa* spp., for example *Vespa crabro, Wasmannia auropunctata, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., for example *Reticulitermes flavipes, Reticulitermeshe sperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diparopsis* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapho-*

*litha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., for example *Ostrinia nubilalis, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella (=Plutella maculipennis), Prays* spp., *Prodenia* spp., *Protoparce* spp., *Pseudaletia* spp., for example *Pseudaletia unipuncta, Pseudoplusia includens, Pyrausta nubilalis, Rachiplusianu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusiani, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., for example *Thrips palmi, Thrips tabaci;* from the order of the Zygentoma (=*Thysanura*), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, in particular from the class of the Bivalvia, for example *Dreissena* spp.;

and also from the class of the Gastropoda, for example *Anion* spp., for example *Anion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp, for example *Ancylostoma duodenale, Ancylostoma ceylanicum, Acylostoma braziliensis, Angiostrongylus* spp., *Anisakis* spp., *Anoplocephala* spp., *Ascaris* spp., *Ascaridia* spp., *Baylisascaris* spp., *Brugia* spp., for example *Brugia malayi, Brugia timori, Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., for example *Dictyocaulus filaria, Diphyllobothrium* spp., for example *Diphyllobothrium latum, Dipylidium* spp., *Dirofilaria* spp., *Dracunculus* spp., for example *Dracunculus medinensis, Echinococcus* spp., for example *Echinococcus granulosus, Echinococcus multilocularis, Echinostoma* spp., *Enterobius* spp., for example *Enterobius vermicularis, Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., for example *Hymenolepis nana, Hyostrongylus* spp., *Litomosoides* spp., *Loa* spp., for example *Loa Loa, Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, for example *Onchocerca volvulus, Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., for example *Strongyloides fuelleborni, Strongyloides stercoralis, Strongylus* spp., *Syngamus* spp., *Taenia* spp., for example *Taenia saginata, Taenia solium, Teladorsagia* spp., *Thelazia* spp., *Toxascaris* spp., *Toxocara* spp., *Trichinella* spp., for example *Trichinella spiralis, Trichinella nativa, Trichinella britovi, Trichinella nelsoni, Trichinella pseudopsiralis, Trichobilharzia* spp., *Trichostrongylus* spp., *Trichuris* spp., for example *Trichuris trichuria, Uncinaria* spp., *Wuchereria* spp., for example *Wuchereria bancrofti;* plant pests from the phylum of the Nematoda, i.e. *phytoparasitic nematodes*, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xy lophilus, Cacopaurus* spp., for example *Cacopaurus pestis, Criconemella* spp., for example *Criconemella curvata, Criconemella onoensis, Criconemella ornata, Criconemella rusium, Criconemella xenoplax (=Mesocriconema xenoplax), Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera*

*rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hirschmaniella* spp., *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paralongidorus* spp., *Paraphelenchus* spp., *Paratrichodorus* spp., for example *Paratrichodorus minor*, *Paratylenchus* spp., *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema* index.

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Suitable penetrants in the present context are all those substances which are usually used for improving the penetration of agrochemically active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds having unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab 1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide.

Further active compounds having an unknown or unclear mechanism of action, for example afidopyropen, afoxolaner, azadirachtin, benclothiaz, benzoximate, bifenazate, broflanilide, bromopropylate, chinomethionat, cryolite, cyclaniliprole, cycloxaprid, cyhalodiamide, dicloromezotiaz, dicofol, diflovidazin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, thiofluoximate, triflumezopyrim and iodomethane; and additionally preparations based on *Bacillus firmus* (1-1582, BioNeem, Votivo), and the following known active compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiroi[indol-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl) oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969), butyl [2-(2,4-dichlorophenyl)-3-oxo-4-oxaspiro[4.5]dec-1-en-1-yl]carbonate (known from CN 102060818), (3E)-3-[1-[(6-chloro-3-pyridyl)methyl]-2-pyridylidene]-1,1,1-trifluoropropan-2-one (known from WO2013/144213, N-(methylsulphonyl)-6-[2-(pyridin-3-yl)-1,3-thiazol-5-yl] pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926), 5-bromo-4-chloro-N-[4-chloro-2-methyl-6-(methylcarbamoyl)phenyl]-2-(3-chloro-2-pyridyl)pyrazole-3-carboxamide (known from CN103232431).

Fungicides

The active compounds specified herein by their common name are known and described, for example, in the "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

1) Ergosterol biosynthesis inhibitors, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsily)propoxy]phenyl}-N-ethyl-N-methylimidoformamide, (1.63) N-ethyl-N-methyl-N'-{2-methyl-5-(trifluoromethyl)-4-[3-(trimethylsily)propoxy] phenyl}imidoformamide, (1.64) O-[1-(4-methoxyphenoxy)-3,3-dimethylbutan-2-yl]-1H-imidazole 1-carbothioate, (1.65) pyrisoxazole, (1.66) 2-{[3-(2-chlorophenyl)-2-(2,4-difluoropheny)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-yl thiocyanate, (1.68) 5-(allylsulphanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-yl thiocyanate, (1.73) 1-{[rel(2R,3R)-3-(2-chlorophenyl)-2-(2,4-difluorophenyl)oxiran-2-yl] methyl}-1H-1,2,4-triazol-5-yl thiocyanate, (1.74) 5-(allylsulphanyl)-1-{[rel(2R,3S)-3-(2-chlorophenyl)-2-(2,4-difluorophenyl)oxiran-2-yl]methyl}-1H-1,2,4-triazole, (1.75) 5-(allylsulphanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1- chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain at complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxan, (2.23) thifluzamid, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain at complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulphanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Inhibitors of mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulphur and sulphur preparations including calcium poly sulphide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of ATP production, for example (8.01) fentin acetate, (8.02) fentin chloride, (8.03) fentin hydroxide, (8.04) silthiofam.

9) Inhibitors of cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Inhibitors of signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) chinomethionat, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezine, (15.015) difenzoquat, (15.016) difenzoquat metilsulphate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and its salts, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanide, (15.048) triazoxide, (15.049) trichlamide, (15.050) zarilamid, (15.051) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1-(4-methoxyphenoxy)-3,3-dimethylbutan-2-yl 1H-imidazole-1-carboxylate, (15.056) 2,3,5,6-tetrachloro-4-(methylsulphonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarbonitrile, (15.067) 3-chloro-5-(4-chlorophenyl)-4-(2,6-difluorophenyl)-6-methylpyridazine, (15.068) 4-(4- chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl) thiophene-2-sulphonohydrazide, (15.071) 5-fluoro-2-[(4-fluorobenzyl)oxy]pyrimidine-4-amine, (15.072) 5-fluoro-2-[(4-methy lbenzy pox)]pyrimidine-4-amine, (15.073) 5-methyl-6-octyl[1,2,4]triazolo[1,5-a]pyrimidine-7-amine, (15.074) ethyl (2Z)-3-amino-2-cyano-3-phenylacrylate, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-yn-1-yloxy)phenyl]propanamide, (15.077) N-[(4-chlorophenyl)(cyano)methyl]-3-[3-methoxy-4-(prop-2-yn-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N-{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-ypoxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.087) pentyl {6-[({[(1-methyl-1H-tetrazol-5-yl)(phenyl)methylene]amino}oxy)methyl]pyridin-2-yl}carbamate, (15.088) phenazine-1-carboxylic acid, (15.089) quinolin-8-ol, (15.090) quinolin-8-ol sulphate (2:1), (15.091) tert-butyl {6-[({[(1-methyl-1H-tetrazol-5-yl)(pheny)methylene]amino}oxy)methyl]pyridin-2-yl}carbamate, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulphonyl)valinamide, (15.094) 4-oxo-4-[(2-phenylethyl)amino]butanoic acid, (15.095) but-3-yn-1-yl {6-[({[(Z)-(1-methyl-1H-tetrazol-5-yl)(pheny)methylene]amino}oxy)methyl]pyridin-2-yl}carbamate, (15.096) 4-amino-5-fluoropyrimidin-2-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methy limidoformamide, (15.111) N'-{5-bromo-6-[(trans-4-isopropylcyclohexyl)oxy)]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazole-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazole-5-amine, (15.139) 4-(2-chloro-4-fluorophenyl)-N-(2,6-difluorophenyl)-1,3-dimethyl-1H-pyrazole-5-amine, (15.140) 4-(2-chloro-4-fluorophenyl)-N-(2-chloro-6-fluorophenyl)-1,3-dimethyl-1H-pyrazole-5-amine, (15.141) 4-(2- bromo-4-fluorophenyl)-N-(2-chloro-6-fluorophenyl)-1,3-dimethyl-1H-pyrazole-5-amine, (15.142) N-(2-bromo-6-fluorophenyl)-4-(2-chloro-4-fluorophenyl)-1,3-dimethyl-1H-pyrazole-5-amine, (15.143) 4-(2-bromo-4-fluorophenyl)-N-(2-bromophenyl)-1,3-dimethyl-1H-pyrazole-5-amine, (15.144) 4-(2-bromo-4-fluorophenyl)-N-(2-bromo-6-fluorophenyl)-1,3-dimethyl-1H-pyrazole-5-amine, (15.145) 4-(2-bromo-4-fluorophenyl)-N-(2-chlorophenyl)-1,3-dimethyl-1H-pyrazole-5-amine, (15.146) N-(2-bromophenyl)-4-(2-chloro-4-fluorophenyl)-1,3-dimethyl-1H-pyrazole-5-amine, (15.147) 4-(2-chloro-4-fluorophenyl)-N-(2-chlorophenyl)-1,3-dimethyl-1H-pyrazole-5-amine, (15.148) 4-(2-bromo-4-fluorophenyl)-N-(2,6-difluorophenyl)-1,3-dimethyl-1H-pyrazole-5-amine, (15.149) 4-(2-bromo-4-fluorophenyl)-N-(2-fluorophenyl)-1,3-dimethyl-1H-pyrazole-5-amine, (15.150) N'-(4-{3-[(difluoromethyl)sulphanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulphanyl]phenoxy}phenyl)-N-ethyl-N-methylimidoformamide, (15.152) N'-(2,5-dimethyl-4-{3-[(2,2,2-trifluoroethyl)sulphanyl]phenoxy}phenyl)-N-ethyl-N-methylimidoformamide, (15.153) N'-(2,5-dimethyl-4-{3-[(2,2,3,3-tetrafluoropropyl)sulphanyl]phenoxy}phenyl)-N-ethyl-N-methylimidoformamide, (15.154) N'-(2,5-dimethyl-4-{3-[(pentafluoroethyl)sulphanyl]phenoxy}phenyl)-N-ethyl-N-methylimidoformamide, (15.155) N'-(4-{[3-(difluoromethoxy)phenyl]sulphanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulphanyl}phenyl)-N-ethyl-N-methylimidoformamide, (15.157) N'-(2,5-dimethyl-4-{[3-(2,2,2-trifluoroethoxy)phenyl]sulphanyl}phenyl)-N-ethyl-N-methylimidoformamide, (15.158) N'-(2,5-dimethyl-4-{[3-(2,2,3,3-tetrafluoropropoxy)phenyl]sulphanyl}phenyl)-N-ethyl-N-methylimidoformamide, (15.159) N'-(2,5-dimethyl-4-{[3-(pentafluoroethoxy)phenyl]sulphanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydrp-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM 1-1562 or *Bacillus firmus*, strain 1-1582 (Accession number CNCM 1-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (Rotylenchulus reniformis nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM I-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa saponin* extract), Pyrethrum/Pyrethrins, *Quassia amara*, *Quercus*, *Quillaja*, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, *Brassicaceae* extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, bell peppers and chili peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all developmental stages of the plants, for example seeds, cuttings and young (immature) plants up to mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material (harvested plants or plant parts) and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. However, the treatment of seed entails a series of problems which cannot always be solved in a satisfactory manner Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been pre-swollen in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C. I. Pigment Red 112 and C. I. Solvent Red 1.

Useful wetting agents which may be present in the seed-dressing formulations usable in accordance with the invention are all substances which promote wetting and which are customary for the formulation of agrochemically active compounds. Alkyl naphthalenesulphonates, such as diisopropyl or diisobutyl naphthalenesulphonates, can be used with preference.

Suitable dispersants and/or emulsifiers which may be present in the seed-dressing formulations usable in accordance with the invention are all nonionic, anionic and cationic dispersants customary for the formulation of agrochemically active compounds. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:
from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;
from the order of the Heteropterida, for example *Cimex* spp., *Triatoma* spp., *Rhodnius* spp., *Panstrongylus* spp.; and also nuisance and hygiene pests from the order of the Blattarida.

Arthropods further include:
from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order of *Mesostigmata* like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic protozoa include:
Mastigophora (Flagellata), for example Trypanosomatidae, for example *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example *Giardia lamblia*, *G. canis*;

Sarcomastigophora (Rhizopoda) such as Entamoebidae, for example *Entamoeba histolytica*, Hartmanellidae, for example *Acanthamoeba* sp., *Harmanella* sp.;

Apicomplexa (Sporozoa) such as Eimeridae, for example *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, Globidium spec., *Isospora belli*, *I. canis*, *I. felis*, *I. ohioensis*, *I. rivolta*, *I. spec.*, *I. suis*, *Cystisospora* spec., *Cryptosporidium* spec., in particular *C. parvum*; such as Toxoplasmadidae, for example *Toxoplasma gondii*, *Hammondia heydornii*, *Neospora caninum*, *Besnoitia besnoitii*; such as Sarcocystidae, for example *Sarcocystis bovicanis*, *S. bovihominis*, *S. ovicanis*, *S. ovifelis*, *S. neurona*, *S.* spec., *S. suihominis*, such as Leucozoidae, for example *Leucozytozoon simondi*, such as Plasmodiidae, for example *Plasmodium berghei*, *P. falciparum*, *P. malariae*, *P. ovale*, *P. vivax*, *P.* spec., such as Piroplasmea, for example *Babesia argentina*, *B. bovis*, *B. canis*, *B.* spec., *Theileria parva*, *Theileria* spec., such as Adeleina, for example *Hepatozoon canis*, *H.* spec.

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order of the Pseudophyllidea for example: *Diphyllobothrium* spp., *Spirometra* spp., *Schistocephalus* spp., *Ligula* spp., *Bothridium* spp., *Diphlogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of the Digenea, for example *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.; Nematodes: Trichinellida, for example *Trichuris* spp., *Capillaria* spp., *Paracapillaria* spp., *Eucoleus* spp., *Trichomosoides* spp., *Trichinella* spp.;

from the order of the Tylenchida, for example *Micronema* spp., *Strongyloides* spp.;

from the order of the Rhabditida, for example *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example *Filicollis* spp.; from the order of the Moniliformida, for example *Moniliformis* spp.;

from the order of the Echinorhynchida, for example *Acanthocephalus* spp., *Echinorhynchus* spp., *Leptorhynchoides* spp.;

Pentastoma: from the order of the Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, especially an arthropodicide such as an insecticide or an acaricide. A further aspect relates to the use of a compound of the formula (I) as an antiectoparasitic agent, especially an arthropodicide such as an insecticide or an acaricide, for example in animal husbandry, in animal breeding, in buildings for livestock or in the hygiene sector.

Anthelmintic Mixing Components

The following anthelmintic mixing components may be mentioned by way of example:

Anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example emodepside, PF1022;

from the class of the aminoacetonitrile derivatives, for example monepantel;

from the class of the tetrahydropyrimidines, for example morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example amidantel, deacylated amidantel (dAMD), tribendimidine;

from the class of the organophosphates, for example coumaphos, crufomate, dichlorvos, haloxone, naphthalofos, trichlorfon;

from the class of the substituted phenols, for example: bithionol, disophenol, hexachlorophene, niclofolan, meniclopholan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) mosquitoes

Anopheles: malaria, filariasis;

Culex: Japanese encephalitis, filariasis, other viral diseases, transmission of worms;

Aedes: yellow fever, dengue fever, filariasis, other viral diseases;

Simuliidae: transmission of worms, in particular *Onchocerca volvulus;*

2) Lice: skin infections, epidemic typhus;

3) Fleas: plague, endemic typhus;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borellioses such as Borrelia duttoni, tick-borne encephalitis, Q fever (*Coxiella burnetii*), babesioses (*Babesia canis canis*).

Examples of vectors in the context of the present invention are insects, such as aphids, flies, leafhoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dims* (malaria) and Culex, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

Description of the Processes and Intermediates

The preparation and use examples which follow illustrate the invention without limiting it. The products were characterized by $^1$H NMR spectroscopy and/or LC-MS (Liquid Chromatography Mass Spectrometry).

The log P values were determined in accordance with OECD Guideline 117 (EC Directive 92/69/EEC) by HPLC (high-performance liquid chromatography) using reversed-phase (RP) columns (C18), by the following methods:

[a] The LC-MS determination in the acidic range is effected at pH 2.7 with 0.1% aqueous formic acid and acetonitrile (contains 0.1% formic acid) as eluents; linear gradient from 10% acetonitrile to 95% acetonitrile.

[b] LC-MS determination in the neutral range is effected at pH 7.8 with 0.001 molar aqueous ammonium hydrogencarbonate solution and acetonitrile as eluents; linear gradient from 10% acetonitrile to 95% acetonitrile.

Calibration is carried out using unbranched alkan-2-ones (having 3 to 16 carbon atoms) with known log P values (log P values determined on the basis of the retention times by linear interpolation between two successive alkanones).

The NMR spectra were determined using a Bruker Avance 400 fitted with a flow probe head (60 µl volume). In individual cases, the NMR spectra were measured with a Bruker Avance II 600.

$^1$H NMR data of selected examples according to $^1$H NMR peak list method:

The $^1$H NMR data of selected examples are stated in the form of $^1$H NMR peak lists. For each signal peak, first the δ value in ppm and then the signal intensity in round brackets are listed. The δ value—signal intensity number pairs for different signal peaks are listed with separation from one another by semicolons.

The peak list for one example therefore has the form of:

$\delta_1$ (intensity 1); $\delta_2$ (intensity 2); . . . ; $\delta_i$ (intensity i); . . . ; $\delta_n$ (intensity n)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

To calibrate the chemical shift of $^1$H-NMR spectra, we use tetramethylsilane and/or the chemical shift of the solvent, particularly in the case of spectra measured in DMSO. Therefore, the tetramethylsilane peak may but need not occur in NMR peak lists.

The lists of the $^1$H NMR peaks are similar to the conventional $^1$H-NMR printouts and thus usually contain all peaks listed in a conventional NMR interpretation.

In addition, like conventional $^1$H NMR printouts, they may show solvent signals, signals of stereoisomers of the target compounds which likewise form part of the subject-matter of the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional $^1$H NMR interpretation.

Further details of $^1$H NMR peak lists can be found in the Research Disclosure Database Number 564025.

PREPARATION EXAMPLES

I. General Synthesis of Compounds of the Formula (I) by Process A:

Example 1: [1-[6-Trifluoromethylpyridin-3-yl]-2 (1H)-pyridinylidene]cyanamide

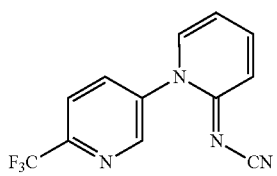

Step 1: Synthesis of Compounds of the Formula (IV)

6'-Trifluoromethyl-[1(2H),3'-bipyridin]-2-one (IV-1)

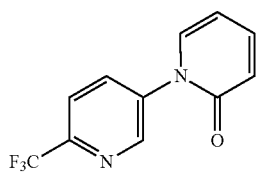 [SMILES: O=c1ccccn1-c1ccc(C(F)(F)F)nc1]

Under an atmosphere of protective gas (argon), 378.7 mg (3.98 mmol) of 2(1H)-pyridinone, 550.3 mg (3.98 mmol) of potassium carbonate and 42.1 mg (0.22 mmol) of copper(I) iodide were added to a solution of 1.0 g (4.42 mmol) of 5-bromo-2-trifluoromethylpyridine in 6 ml of N,N-dimethylformamide. The reaction mixture was then stirred at 120° C. for 20 hours. For work-up, the reaction was, after cooling, stirred in 60 ml of water and extracted three times with ethyl acetate. The organic phase was removed, dried and concentrated under reduced pressure. The residue that remained was purified by column chromatography on silica gel. This gave 420 mg (100% pure, 35.6% yield) of 6'-trifluoromethyl-[1(2H),3'-bipyridin]-2-one.

Log P value (HCOOH)=1.26

$^1$H-NMR (400.0 MHz, d$_6$-DMSO): δ=8.897 (11.9); 8.891 (12.3); 8.316 (0.4); 8.272 (6.0); 8.267 (6.0); 8.251 (7.8); 8.246 (7.9); 8.117 (16.0); 8.096 (12.3); 7.814 (7.8); 7.811 (8.5); 7.797 (8.3); 7.794 (8.5); 7.601 (5.1); 7.596 (5.1); 7.585 (5.6); 7.579 (8.0); 7.573 (5.6); 7.562 (5.7); 7.557 (5.3); 6.568 (10.6); 6.545 (10.1); 6.433 (6.0); 6.430 (5.9); 6.416 (11.2); 6.414 (10.8); 6.400 (5.8); 6.397 (5.5); 3.327 (32.7); 2.675 (0.6); 2.671 (0.8); 2.667 (0.6); 2.524 (1.8); 2.506 (96.2); 2.502 (125.8); 2.497 (94.3); 2.333 (0.6); 2.329 (0.8); 2.324 (0.6); 1.398 (1.1); 0.008 (0.9); 0.000 (26.8); −0.008 (1.3).

$^{13}$C-NMR (600 MHz, DMSO-d$_6$, ppm) δ=106.6; 120.8; 138.6; 141.7 (=CH—); 121.6 (CF$_3$, hetaryl); 121.4; 137.0; 139.9; 145.5; 148.6 (4×=CH—, hetaryl); 161.2 (C=O) ppm.

Step 2: Synthesis of Compounds of the Formula (V)

2-Chloro-1-(6-trifluoromethylpyridin-3-yl)pyridinium chloride (V-1)

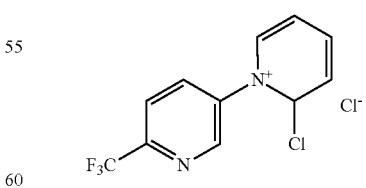

1.9 ml (20.8 mmol) of phosphoryl chloride and a drop of N,N-dimethylformamide were added in succession to 1.0 g (4.16 mmol) of 6'-trifluoromethyl-[1(2H),3'-bipyridin]-2-one dissolved in 40 ml of dichloromethane. The reaction mixture was then stirred at reflux temperature for 6 hours. The reaction was then concentrated to dryness under reduced pressure and the isolated 2-chloro-1-(6-trifluoromethylpyridin-3-yl)pyridinium chloride (V-1) was directly reacted further according to Step 3.

Step 3: [1-[6-Trifluoromethylpyridin-3-yl]-2(1H)-pyridinylidene]cyanamide 1.2 g (4.16 mmol) of 2-chloro-1-(6-trifluoromethylpyridin-3-yl)pyridinium chloride (V-1) were stirred in 80 ml of acetonitrile, 192.4 mg (4.57 mmol) of cyanamide and 661.1 mg (4.78 mmol) of potassium carbonate were added and the mixture was stirred at room temperature for about 18 hours. For work-up, the precipitated salts were filtered off. The entire reaction mixture was then concentrated under reduced pressure and the crude product that remained was purified by column chromatography on silica gel (mobile phase: cyclohexane-acetone gradient). This gave 310 mg (99.04% pure, 28.2% yield) of [1-[6-trifluoromethylpyridin-3-yl]-2(1H)-pyridinylidene]cyanamide.

Alternatively and analogously to Example 24 below, 32.7 g (82.1 mmol) of [1-[6-trifluoromethylpyridin-3-yl]-2-(methylthio)pyridinium iodide (prepared from the 6'-trifluoromethyl-[1(2H),3'-bipyridine]-2-thione (VI-2) according to Example 24, Synthesis Step 3), 10.5 g (164.2 mmol) of sodium hydrogen cyanamide and 919 ml of acetonitrile were used. This gave 13.6 g (100% pure, 62.9% yield) of [1-[6-trifluoromethylpyridin-3-yl]-2(1H)-pyridinylidene]cyanamide.

$^1$H-NMR (600.1 MHz, d$_6$-DMSO): δ=8.958 (12.7); 8.954 (12.8); 8.361 (6.5); 8.357 (6.5); 8.347 (7.7); 8.343 (7.8); 8.187 (16.0); 8.173 (13.7); 8.052 (8.6); 8.051 (9.2); 8.041 (9.2); 8.040 (9.1); 7.912 (5.8); 7.910 (5.8); 7.901 (6.3); 7.898 (9.6); 7.894 (6.3); 7.886 (6.4); 7.883 (6.1); 7.289 (11.5); 7.274 (10.9); 6.864 (6.3); 6.862 (6.4); 6.852 (12.2); 6.850 (12.0); 6.841 (6.3); 6.839 (6.1); 5.752 (0.5); 3.406 (0.4); 3.396 (0.4); 3.383 (1.1); 3.363 (866.4); 3.341 (0.5); 3.334 (0.4); 2.617 (0.4); 2.526 (0.7); 2.523 (0.8); 2.519 (0.8); 2.511 (19.8); 2.508 (42.7); 2.505 (58.9); 2.502 (42.5); 2.499 (19.7); 2.389 (0.4); 2.037 (0.5); 2.036 (0.5); 1.466 (0.4); 1.356 (0.4); 1.322 (1.0); 1.236 (0.5); 1.133 (0.9); 0.000 (5.1)

$^{13}$C-NMR (600 MHz, DMSO-d$_6$, ppm) δ=117.1 (CN); 121.5 (hetaryl-CF$_3$); 111.3; 118.1; 121.9; 137.7; 148.9; 140.0; 142.9 (7×=CH—, hetaryl); 140.0; 146.6 (2×hetaryl-C); 162.2 (C=N—) ppm.

Example 2: [1-[6-Bromopyridin-3-yl]-2(1H)-pyridinylidene]cyanamide

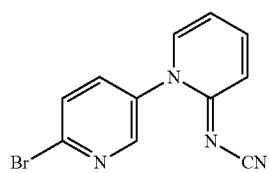 [SMILES: N#C/N=c1\ccccn1-c1ccc(Br)nc1]

Step 1: Synthesis of Compounds of the Formula (IV)

6'-Bromo-[1(2H), 3'-bipyridin]-2-one (IV-2)

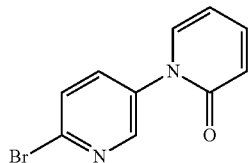 [SMILES: O=c1ccccn1-c1ccc(Br)nc1]

1.2 g (12.3 mmol) of 2(1H)-pyridinone were stirred in a mixture of 180 ml of dichloromethane and 30 ml of N,N-dimethylformamide, and 4.5 g (24.7 mmol) of copper(I) acetate, 2.0 ml of pyridine and 5.0 g (24.7 mmol) of 6-bromo-3-pyridinylboronic acid were added in succession. 4 Å molecular sieve was then added, and the mixture was stirred vigorously in an open vessel for three days Ammonium hydroxide solution was then added to the reaction mixture, resulting in the precipitation of a greasy residue. The supernatant was decanted off and the oil that remained was washed and concentrated under reduced pressure. The residue that remained was purified by column chromatography on silica gel (mobile phase: cyclohexane—acetone gradient). This gave 2.5 g (98.5% pure, 39.5% yield) of 6'-bromo-[1(2H),3'-bipyridin]-2-one.

Log P value (HCOOH)=0.95

$^1$H-NMR (400.0 MHz, d$_6$-DMSO): δ=8.507 (12.1); 8.502 (12.0); 8.501 (11.9); 7.926 (7.2); 7.919 (7.0); 7.905 (11.0); 7.898 (11.0); 7.831 (15.4); 7.829 (16.0); 7.809 (10.0); 7.808 (10.3); 7.737 (6.7); 7.733 (7.2); 7.732 (6.7); 7.719 (7.1); 7.716 (7.2); 7.715 (6.7); 7.569 (4.5); 7.564 (4.5); 7.553 (4.9); 7.547 (6.9); 7.541 (4.9); 7.530 (5.0); 7.525 (4.6); 6.529 (9.1); 6.506 (8.6); 6.389 (5.1); 6.386 (5.3); 6.372 (9.3); 6.369 (9.5); 6.355 (5.0); 6.352 (5.0); 3.308 (45.2); 2.674 (0.5); 2.670 (0.7); 2.665 (0.5); 2.505 (83.4); 2.501 (109.7); 2.496 (81.8); 2.332 (0.5); 2.327 (0.7); 2.323 (0.5); 1.398 (0.5); 0.008 (0.8); 0.000 (23.6); −0.008 (1.0).

Step 2: Synthesis of Compounds of the Formula (V)

2-Bromo-1-(6-bromopyridin-3-yl)pyridinium bromide (V-2)

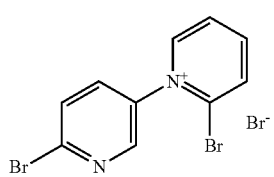 [SMILES: Brc1ccc(-[n+]2ccccc2Br)cn1 ; [Br-]]

5.9 g (19.9 mmol) of phosphoryl bromide were added to 1.0 g (3.98 mmol) of 6'-bromo-[1(2H),3'-bipyridin]-2-one dissolved in 30 ml of dichloroethane. Thereafter, the reaction mixture was stirred at reflux temperature for about 18 hours. The reaction was then concentrated to dryness under reduced pressure and 2-bromo-1-(6-bromopyridin-3-yl)pyridinium bromide (V-2) was directly reacted further according to Step 3.

Step 3: [1-[6-Bromopyridin-3-yl]-2(1H)-pyridi-nylidene]cyanamide 1.6 g (4.00 mmol) of 2-bromo-1-(6-bromopyridin-3-yl)pyridinium bromide (V-2) were stirred in 30 ml of acetonitrile, 184.9 mg (4.40 mmol) of cyanamide and 635.7 mg (4.60 mmol) of potassium carbonate were added and the mixture was stirred at room temperature for about 18 hours. For work-up, the precipitated salts were filtered off. The entire reaction mixture was then concentrated under reduced pressure and the crude product that remained was purified by column chromatography on silica gel (mobile phase: cyclohexane—acetone gradient). This gave 47 mg (95.4% pure, 4.0% yield) of [1-[6-bromopyridin-3-yl]-2(1H)-pyridinylidene]cyanamide.

Log P value (HCOOH)=1.07.

$^1$H-NMR (400.0 MHz, $d_6$-DMSO): δ=8.589 (0.6); 8.583 (0.7); 8.568 (11.2); 8.562 (11.7); 8.310 (0.5); 8.121 (0.4); 8.114 (0.4); 8.099 (0.4); 8.092 (0.4); 8.011 (6.7); 8.004 (7.6); 7.999 (7.6); 7.996 (8.1); 7.990 (10.6); 7.983 (16.0); 7.898 (14.4); 7.887 (4.7); 7.883 (4.6); 7.877 (10.3); 7.870 (5.3); 7.866 (7.5); 7.861 (4.9); 7.848 (4.7); 7.844 (4.4); 7.769 (0.6); 7.748 (0.5); 7.259 (9.2); 7.237 (8.5); 6.828 (4.8); 6.825 (4.9); 6.811 (9.2); 6.808 (9.2); 6.794 (4.7); 6.791 (4.5); 3.321 (52.9); 2.674 (0.9); 2.670 (1.3); 2.666 (1.0); 2.523 (3.1); 2.505 (148.4); 2.501 (196.8); 2.496 (148.0); 2.332 (0.9); 2.328 (1.3); 2.323 (1.0); 2.085 (6.2); 1.398 (1.2); 0.008 (0.9); 0.000 (26.7).

Examples 13 to 15 and 18 to 23 mentioned in Tables 3 and 4 were also synthesized according to Process A.

II. General Synthesis of Compounds of the Formula (I) by Process B

Example 3: [1-[6-Methylpyridin-3-yl]-2(1H)-pyridi-nylidene]cyanamide

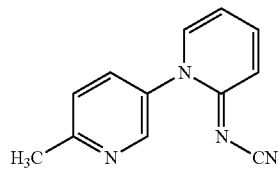 [SMILES: Cc1ccc(-n2cccc/c2=N\C#N)cn1]

Step 1: Synthesis of Compounds of the Formula (IV)

6'-Methyl-[1(2H),3'-bipyridin]-2-one (IV-3)

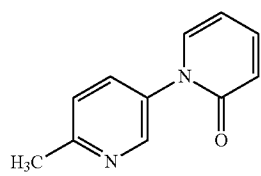

Variant A:

Under an atmosphere of protective gas (argon), 1.1 g (12.0 mmol) of 2(1H)-pyridinone, 3.3 g (24.0 mmol) of potassium carbonate, 457.0 mg (2.4 mmol) of copper(I) iodide and 341.4 mg (2.4 mmol) of N,N'-dimethylcyclohexane-1,2-diamine were added to a solution of 2.0 g (12.0 mmol) of 5-bromo-2-methylpyridine in 12 ml of toluene. The reaction mixture was then stirred at 110° C. for 12 hours. For work-up, the reaction was, after cooling, diluted with dichloromethane, and the solid was separated off. The solid was washed once more with dichloromethane. The filtrate was then washed with water, dried and concentrated under reduced pressure. The residue that remained was purified by column chromatography on silica gel (mobile phase:cyclohexane—acetone gradient). This gave 390 mg (100% pure, 17.4% yield) of 6'-methyl-[1(2H),3'-bipyridin]-2-one.

$^1$H-NMR (400.0 MHz, $d_6$-DMSO): δ=8.477 (12.9); 8.472 (13.0); 8.317 (0.4); 7.789 (10.6); 7.783 (10.4); 7.768 (11.7); 7.762 (11.4); 7.693 (9.4); 7.692 (9.6); 7.689 (10.7); 7.676 (9.7); 7.675 (10.0); 7.671 (10.6); 7.553 (6.6); 7.548 (6.4); 7.537 (7.2); 7.531 (10.3); 7.525 (6.8); 7.514 (7.1); 7.508 (6.5); 7.416 (16.0); 7.395 (14.2); 6.508 (13.5); 6.486 (12.7); 6.361 (7.7); 6.358 (7.5); 6.344 (14.3); 6.341 (13.6); 6.327 (7.3); 6.324 (6.8); 3.332 (182.6); 2.692 (0.7); 2.676 (1.0); 2.671 (1.3); 2.667 (1.0); 2.535 (109.8); 2.507 (146.5); 2.502 (188.3); 2.498 (139.5); 2.374 (0.6); 2.329 (1.7); 2.205 (1.2); 2.086 (0.6); 1.397 (2.2); 0.146 (0.5); 0.008 (4.7); 0.000 (111.6); −0.008 (5.3); −0.150 (0.5).

Variant B:

1.5 g (12.1 mmol) of 2(1H)-pyridinone were stirred in a mixture of 100 ml of dichloromethane and 10 ml of N,N-dimethylformamide, and 4.4 g (23.3 mmol) of copper(I) acetate, 2.0 ml of pyridine and 2.0 g (14.6 mmol) of 6-methyl-3-pyridinylboronic acid were added in succession. 4 A molecular sieve was then added, and the reaction was stirred vigorously for several days Ammonium hydroxide solution was then added to the reaction mixture, resulting in the precipitation of a greasy residue. The supernatant was decanted off and the oil that remained was washed. The mixture was then concentrated under reduced pressure on a rotary evaporator and the residue that remained was purified by column chromatography on silica gel (mobile phase: cyclohexane—acetone gradient). This gave 74 mg (100% pure, 2.7% yield) of 6'-methyl-[1(2H),3'-bipyridin]-2-one.

Step 2: Synthesis of Compounds of the Formula (VI)

6'-Methyl-[1(2H),3'-bipyridine]-2-thione (VI-1)

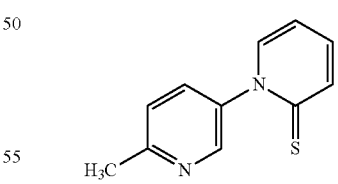

700.0 mg (3.75 mmol) of 6'-methyl-[1(2H),3'-bipyridin]-2-one (IV-3) and 3.15 g (37.5 mmol) of sodium bicarbonate were stirred in 20 ml of 1,4-dioxane. After addition of 4.17 g (18.7 mmol) of diphosphorus pentasulphide, the reaction was stirred at 80° C. for about 18 hours. For work-up, the solvent was removed under reduced pressure and the residue that remained was shaken with dichloromethane and water. The organic phase was removed, dried and concentrated under reduced pressure. The residue that remained was purified by column chromatography on silica gel (mobile phase gradient:cyclohexane:acetone gradient). This gave 225 mg (99% pure, 29.3% yield) of 6'-methyl-[1(2H),3'-bipyridine]-2-thione.

Log P value (HCOOH)=0.51

$^1$H-NMR (400.0 MHz, d$_6$-DMSO): δ=8.431 (14.4); 8.425 (14.8); 8.316 (0.5); 8.038 (9.2); 8.036 (9.5); 8.021 (9.6); 8.019 (9.5); 7.779 (9.8); 7.772 (9.6); 7.758 (11.0); 7.752 (10.8); 7.567 (8.0); 7.546 (12.2); 7.475 (7.3); 7.471 (7.6); 7.458 (8.2); 7.454 (11.5); 7.449 (6.0); 7.441 (16.0); 7.437 (8.0); 7.432 (6.0); 7.420 (13.7); 6.899 (6.5); 6.896 (6.7); 6.882 (12.0); 6.879 (12.0); 6.866 (6.1); 6.862 (6.0); 6.539 (0.3); 3.740 (0.4); 3.725 (0.3); 3.378 (0.5); 3.364 (0.5); 3.332 (126.2); 3.309 (1.1); 2.706 (0.5); 2.676 (0.6); 2.671 (0.8); 2.667 (0.6); 2.549 (94.8); 2.525 (2.6); 2.511 (43.5); 2.507 (86.6); 2.502 (113.0); 2.498 (83.5); 2.494 (42.5); 2.388 (0.6); 2.333 (0.6); 2.329 (0.7); 2.325 (0.6); 2.086 (2.1); 1.397 (0.9); 1.235 (0.4); 0.000 (4.6).

The compounds (VI-2) to (VI-4) and (VI-6) to (VI-10) mentioned in Table 2 were obtained in an analogous manner Step 3: Synthesis of Compounds of the Formula (VII)

[1-[6-Methylpyridin-3-yl]-2-(methylthio)pyridinium iodide (VII-1)

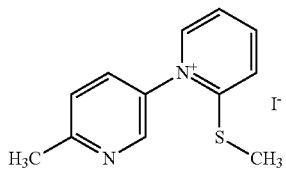

190.0 mg (0.93 mmol) of 6'-methyl-[1(2H),3'-bipyridine]-2-thione (VI-1) (synthesis according to Step 2) were initially charged in 30 ml of acetonitrile, 1.3 g (9.4 mmol) of methyl iodide were added and the mixture was stirred at room temperature for about 18 hours. LC-MS control showed that the reaction had ended. The reaction was then concentrated under reduced pressure and the crude product (VII-1) that remained was reacted without further purification in the next reaction step.

Step 4: [1-[6-Methylpyridin-3-yl]-2(1H)-pyridinylidene]cyanamide 630.6 mg (15.0 mmol) of cyanamide and 201.8 mg (6.3 mmol) of hydrazine hydrate were added to 309.7 mg (0.90 mmol) of [1-[6-methylpyridin-3-yl]-2-(methylthio)pyridinium iodide (VII-1) (synthesis according to Step 3) dissolved in 20 ml of acetonitrile. The reaction mixture was then stirred at room temperature for 2 hours. Control by thin-layer chromatogram (mobile phase:cyclohexane:acetone) showed that the reaction had ended. For work-up, the reaction was concentrated under reduced pressure and the residue that remained was purified by column chromatography on silica gel (mobile phase gradient:cyclohexane:acetone gradient). This gave a plurality of fractions, of which the fraction with the target component was purified once more by preparative HPLC (acetone-water gradient). This gave 11 mg (100% pure, 5.8% yield) of [1-[6-methyl-pyridin-3-yl]-2(1H)-pyridinylidene]cyanamide.

Log P value (HCOOH)=0.46

$^1$H-NMR (400.0 MHz, d$_6$-DMSO): δ=8.526 (15.0); 8.520 (15.4); 8.313 (0.5); 7.968 (9.4); 7.965 (10.3); 7.951 (10.0); 7.949 (10.4); 7.877 (6.4); 7.873 (6.5); 7.867 (10.7); 7.860 (15.9); 7.855 (11.8); 7.850 (8.5); 7.847 (12.3); 7.840 (12.9); 7.833 (7.0); 7.466 (16.0); 7.446 (14.5); 7.253 (12.6); 7.230 (11.6); 6.807 (6.8); 6.804 (6.9); 6.790 (13.0); 6.787 (12.8); 6.773 (6.7); 6.770 (6.4); 5.753 (2.6); 3.513 (0.4); 3.347 (19.7); 2.715 (0.5); 2.675 (0.7); 2.670 (1.0); 2.666 (0.7); 2.592 (0.4); 2.559 (95.1); 2.524 (2.4); 2.510 (55.3); 2.506 (109.6); 2.501 (145.4); 2.497 (109.4); 2.493 (56.2); 2.455 (0.4); 2.449 (0.4); 2.398 (0.7); 2.333 (0.7); 2.328 (1.0); 2.324 (0.7); 2.010 (0.6); 1.991 (0.6); 1.290 (0.4); 1.236 (2.7); 0.855 (0.8); 0.837 (0.4); 0.008 (2.5); 0.000 (58.8); −0.008 (2.6); −0.028 (0.4); −0.062 (4.9); −0.150 (0.3).

Examples 16 and 17 in Tables 3 and 4 were also synthesized according to Process B.

III. General Synthesis of Compounds of the Formula (I) by Method C:

Example 4: (3E)-3-[1-(6-Trifluoromethyl-3-pyridinyl)-2(1H)-pyridinylidene]-1,1,1-trifluoro-2-propanone

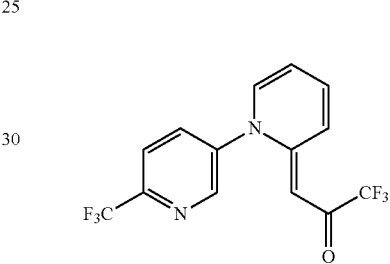

Under protective gas (argon), 1,1,1-trifluoro-3-(2-pyridinyl)-2-propanone (see WO 2005/030736 A1; UORSY Building Blocks Library), 414.6 mg (3.0 mmol) of potassium acetate and 28.5 mg (0.15 mmol) of copper(I) iodide were added to 677.9 mg (3.0 mmol) of 5-bromo-2-trifluoromethylpyridine in 5 ml of degassed N,N-dimethylformamide, and the mixture was stirred at 120° C. for 20 hours. The reaction was then shaken with saturated sodium chloride solution and ethyl acetate. The organic phase was separated off, dried and concentrated to dryness under reduced pressure. The residue that remained was purified by column chromatography on silica gel (mobile phase gradient:cyclohexane:acetone gradient). This gave 20 mg (100% pure, 1.9% yield) of (3E)-3-[1-(6-trifluoromethyl-3-pyridinyl)-2(1H)-pyridinylidene]-1,1,1-trifluoro-2-propanone.

Log P value (HCOOH)=2.20

$^1$H-NMR (400.0 MHz, d$_6$-DMSO): δ=9.069 (8.5); 9.063 (8.7); 8.983 (6.4); 8.961 (6.7); 8.514 (4.2); 8.508 (4.2); 8.493 (5.1); 8.488 (5.1); 8.312 (10.1); 8.291 (8.3); 8.129 (6.2); 8.113 (6.3); 7.942 (3.2); 7.922 (4.8); 7.902 (3.3); 7.030 (3.6); 7.027 (3.6); 7.013 (8.8); 7.010 (6.7); 6.996 (3.5); 6.993 (3.4); 5.758 (0.4); 4.583 (16.0); 3.351 (6.6); 3.062 (0.7); 2.880 (0.7); 2.673 (0.8); 2.567 (0.5); 2.554 (0.5); 2.526 (2.1); 2.508 (91.2); 2.504 (117.2); 2.499 (86.1); 2.335 (0.5); 2.330 (0.7); 2.228 (0.3); 1.236 (2.1); 1.140 (1.1); 0.008 (2.1); 0.000 (50.0); −0.008 (2.2).

$^{13}$C-NMR (600 MHz, DMSO-d$_6$, ppm) δ=83.1 (=$\underline{C}$H—); 119.4 ($\underline{C}$F$_3$, hetaryl); 122.2 ($\underline{C}$F$_3$); 114.7; 123.4; 138.0; 140.6; 141.2; 149.3 (6×=$\underline{C}$H—, hetaryl); 138.1; 141.7; 157.5 (3×hetaryl-$\underline{C}$); 171.7 ($\underline{C}$=O) ppm.

Example 5: (3E)-3-[1-(6-Chloro-3-pyridinyl)-2(1H)-pyridinylidene]-1,1,1-trifluoro-2-propanone

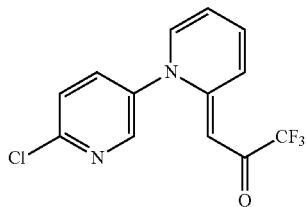 [SMILES: O=C(/C=C1\C=CC=CN1c1ccc(Cl)nc1)C(F)(F)F]

The preparation was carried out analogously from:

288.6 mg (1.5 mmol) of 2-chloro-5-bromopyridine, 283.7 mg (1.5 mmol) of 1,1,1-trifluoro-3-(2-pyridinyl)-2-propanone (see WO 2005030736 A1), 207.3 mg (1.5 mmol) of potassium acetate, 14.2 mg (0.07 mmol) of copper(I) iodide and 3 ml of degassed N,N-dimethylformamide.

This gave 12 mg (100% pure, 2.6% yield) of (3E)-3-[1-(6-chloro-3-pyridinyl)-2(1H)-pyridinylidene]-1,1,1-trifluoro-2-propanone.

$^1$H-NMR (600.1 MHz, CD$_3$CN): δ=9.035 (4.4); 9.020 (4.5); 8.478 (6.8); 8.473 (6.9); 7.914 (4.6); 7.910 (4.5); 7.900 (5.2); 7.896 (5.0); 7.752 (2.4); 7.738 (3.6); 7.727 (2.0); 7.725 (2.3); 7.683 (8.0); 7.669 (7.0); 7.621 (4.4); 7.620 (4.1); 7.609 (4.4); 6.835 (2.7); 6.833 (2.6); 6.824 (5.2); 6.822 (4.9); 6.813 (2.6); 6.810 (2.4); 4.772 (11.1); 3.131 (0.4); 2.612 (1.7); 2.579 (3.7); 2.546 (0.6); 2.250 (0.4); 2.237 (0.3); 2.193 (0.5); 2.178 (0.5); 2.164 (0.5); 2.149 (0.4); 2.138 (0.4); 2.119 (6.8); 2.106 (0.5); 2.050 (0.4); 1.964 (0.7); 1.955 (2.0); 1.951 (2.8); 1.948 (22.8); 1.943 (41.6); 1.939 (60.7); 1.935 (41.2); 1.931 (20.9); 1.881 (0.3); 1.824 (0.4); 1.386 (1.0); 1.341 (0.7); 1.285 (1.4); 1.270 (3.4); 1.189 (5.6); 1.180 (16.0); 0.893 (0.3); 0.882 (0.7); 0.870 (0.4); 0.005 (0.8); 0.000 (26.3); −0.006 (1.1).

$^{13}$C-NMR (600 MHz, DMSO-d$_6$, ppm) δ=82.9 (=CH—); 119.4 (CF$_3$, hetaryl); 114.6; 123.4; 126.9; 138.9; 140.9; 141.9; 148.7 (7×=CH—, hetaryl); 138.7; 153.2; 157.6 (3×hetaryl-C); 171.5 (C=O) ppm.

Example 6: (3E)-3-[1-(Pyridinyl)-2(1H)-pyridinylidene]-1,1,1-trifluoro-2-propanone

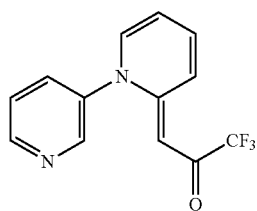 [SMILES: O=C(/C=C1\C=CC=CN1c1cccnc1)C(F)(F)F]

Under protective gas (argon), a mixture of 359.16 mg (1.5 mmol) of 2-chloro-5-iodopyridine, 283.7 mg (1.5 mmol) of 1,1,1-trifluoro-3-(2-pyridinyl)-2-propanone (see WO 2005/030736 A1), 621.9 mg (4.5 mmol) of potassium carbonate, 57.1 mg (0.30 mmol) of copper(I) iodide, 74.6 mg (0.45 mmol) of potassium iodide and 85.3 mg (0.6 mmol) of N,N'-dimethylcyclohexane-1,2-diamine in 3 ml of degassed N,N-dimethylformamide was heated in a microwave at 200° C. for about 10 minutes. For work-up, the reaction mixture was extracted by shaking successively with saturated sodium chloride solution and ethyl acetate. The organic phase was removed and concentrated under reduced pressure. The residue that remained was purified by column chromatography on silica gel (mobile phase: cyclohexane-acetone gradient). This gave 14 mg (3.5% yield) of (3E)-3-[1-(pyridinyl)-2(1H)-pyridinylidene]-1,1,1-trifluoro-2-propanone which still contains traces of the compound of Example 5 (according to NMR spectrum).

$^1$H-NMR (400.0 MHz, CD$_3$CN): δ=9.051 (2.4); 9.028 (2.5); 8.708 (2.0); 8.706 (2.1); 8.696 (2.1); 8.694 (2.1); 8.479 (0.3); 8.472 (0.3); 8.120 (1.1); 8.115 (1.1); 8.100 (2.2); 8.096 (2.2); 8.081 (1.4); 8.076 (1.3); 7.772 (1.2); 7.744 (3.2); 7.727 (3.2); 7.686 (0.4); 7.664 (0.4); 7.648 (1.7); 7.636 (1.8); 7.629 (1.7); 7.617 (1.5); 7.581 (3.0); 7.561 (2.8); 6.855 (1.3); 6.838 (2.6); 6.821 (1.4); 4.775 (5.9); 3.360 (1.3); 3.131 (1.7); 2.612 (1.8); 2.579 (4.2); 2.155 (19.2); 2.120 (7.0); 2.107 (0.7); 1.964 (0.8); 1.952 (10.4); 1.946 (18.5); 1.940 (24.5); 1.934 (17.5); 1.927 (9.3); 1.330 (0.4); 1.285 (0.5); 1.270 (1.0); 1.190 (6.1); 1.180 (16.0); 0.146 (0.4); 0.000 (73.7); −0.150 (0.4).

$^{13}$C-NMR (600 MHz, DMSO-d$_6$, ppm) δ=82.3 (=CH—); 119.5 (CF$_3$, hetaryl); 114.5; 122.6; 123.4; 126.7; 139.8; 141.1; 141.2; 151.5 (8×=CH—, hetaryl); 154.3; 156.5 (3×hetaryl-C); 171.2 (C=O) ppm.

Example 7: [1-[6-Trifluoromethylpyridin-3-yl]-2(1H)-pyridinylidene]trifluoromethylcyanamide

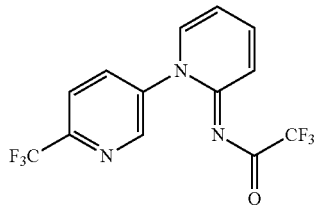 [SMILES: O=C(/N=c1\ccccn1-c1ccc(C(F)(F)F)nc1)C(F)(F)F]

Step 1: Synthesis of Compounds of the Formula (VII)

6'-Trifluoromethyl-[1(2H),3'-bipyridin]-2-imine (VIII-1)

With ice cooling, 500.0 mg (1.7 mmol) of 2-chloro-1-(6-trifluoromethylpyridin-3-yl)pyridinium chloride (V-1) (cf. Method A, Step 2) were stirred in 20 ml of 7N ammonia in methanol, and the mixture was stirred at room temperature for 30 minutes. The reaction was then concentrated under reduced pressure on a rotary evaporator and the residue that remained (VII-1) was directly reacted further.

Step 2: [1-[6-Trifluoromethylpyridin-3-yl]-2(1H)-pyridinylidene]trifluoromethylacetamide 217.0 mg (1.6 mmol) of trifluoromethyl-[1(2H),3'-bipyridin]-2-imine (VIII-1) were stirred in 400 ml of dichloromethane, and, with ice cooling, 809.5 mg (8.0 mmol) of N,N-dimethylaminopyridine (DMAP) and 336.0 mg (1.6 mmol) of trifluoroacetic anhydride were added in succession. The reaction mixture was then warmed to room temperature and stirred for about 18 hours. For work-up, the reaction was diluted with ethyl acetate and washed repeatedly with water. The organic phase was removed, dried and concentrated under reduced pressure. The residue that remained was purified by column chromatography on silica gel. This gave 51 mg (95.6% pure, 9.1% yield) of 1-[6-trifluoromethylpyridin-3-yl]-2-(1H)-pyridinylideneltrifluoromethylacetamide and 148 mg (97.9% pure, 23.6% yield) of N-[1-[6-trifluoromethylpyridin-3-yl]-2(1H)-pyridinylidene]-(6-trifluoromethylpyridin-3-yl)amine.

Log P value (HCOOH)=2.19

$^1$H-NMR (400.0 MHz, d$_6$-DMSO): δ=8.981 (9.9); 8.975 (9.7); 8.898 (0.5); 8.892 (0.5); 8.478 (6.7); 8.475 (6.9); 8.461 (7.9); 8.457 (11.9); 8.433 (8.5); 8.386 (4.8); 8.380 (4.7); 8.365 (5.9); 8.359 (5.8); 8.318 (0.6); 8.272 (0.5); 8.247 (5.0); 8.243 (4.7); 8.229 (5.3); 8.225 (7.9); 8.220 (4.2); 8.207 (16.0); 8.186 (9.7); 8.119 (0.6); 8.098 (0.5); 7.817 (0.3); 7.813 (0.4); 7.800 (0.3); 7.795 (0.4); 7.737 (0.5); 7.716 (0.5); 7.581 (0.3); 7.303 (4.5); 7.300 (4.6); 7.286 (7.7); 7.283 (7.7); 7.269 (4.2); 7.266 (4.1); 6.569 (0.5); 6.546 (0.5); 6.418 (0.7); 6.056 (0.4); 6.017 (0.4); 3.331 (297.3); 3.019 (0.4); 2.993 (0.4); 2.676 (1.4); 2.672 (1.9); 2.667 (1.4); 2.525 (5.8); 2.511 (107.0); 2.507 (213.5); 2.503 (278.6); 2.498 (203.4); 2.494 (100.4); 2.334 (1.2); 2.329 (1.7); 2.325 (1.3); 2.180 (0.5); 2.086 (1.0); 1.398 (3.5); 1.236 (7.7); 0.854 (0.8); 0.837 (0.4); 0.008 (2.4); 0.000 (73.5); −0.008 (3.0); −0.150 (0.3).

$^{13}$C-NMR (600 MHz, DMSO-d$_6$, ppm) δ=116.9 (CF$_3$); 121.5 (hetaryl-CF$_3$); 115.7; 120.6; 121.3; 137.4; 141.6; 145.1; 148.7 (7×=CH—, hetaryl); 140.8; 146.4 (2×hetaryl-C); 159.1 (C=N—); 161.7 (C=O) ppm.

N-[1-[6-Trifluoromethylpyridin-3-yl]-2(1H)-pyridinylidene]-(6-trifluoromethylpyridin-3-yl)amine $^{13}$C-NMR (600 MHz, DMSO-d$_6$, ppm) δ=121.5; 122.3 (2×hetaryl-CF$_3$); 106.0; 114.1; 121.6; 121.6; 129.6; 137.4; 138.8; 138.9; 144.4; 149.3 (10×=CH—, hetaryl); 139.0; 141.4; 145.3; 149.7 (4×hetaryl-C); 153.7 (C=N—) ppm.

Examples 9 to 11 in Tables 3 and 4 were also synthesized analogously to Example 7.

Example 8: [1-[6-Fluoropyridin-3-yl]-2(1H)-pyridinylidene]cyanamide

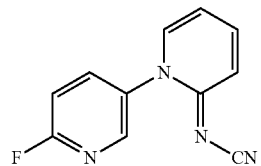 [SMILES: N#C/N=c1\ccccn1-c1ccc(F)nc1]

At room temperature, 946 mg (5 mmol) of fluoro-[1(2H),3'-bipyridin]-2-imine (VIII-2) were stirred in 50 ml of N,N-dimethylformamide. 4.7 g (47.1 mmol) of triethylamine and 2.6 g (25.0 mmol) of cyanogen bromide were then added in succession. The reaction mixture was stirred at 60° C. for about 18 hours. After cooling to room temperature, saturated sodium bicarbonate solution was added and the reaction was then extracted with ethyl acetate. The organic phase was removed, dried and concentrated under reduced pressure. The residue that remained was purified by column chromatography on silica gel (mobile phase: cyclohexane-acetone gradient). This gave 51 mg (94.8% pure, 4.5% yield) of [1-[6-fluoropyridin-3-yl]-2(1H)-pyridiny lidene]cyanamide.

Log P value (HCOOH)=0.70

$^1$H-NMR (400.0 MHz, d$_6$-DMSO): δ=9.087 (0.9); 8.753 (1.5); 8.423 (14.4); 8.417 (15.7); 8.383 (0.7); 8.313 (0.7); 8.255 (5.4); 8.249 (5.6); 8.238 (6.6); 8.231 (9.5); 8.227 (7.6); 8.216 (6.1); 8.209 (5.7); 8.173 (2.5); 8.036 (0.6); 8.029 (0.7); 8.005 (13.4); 7.990 (12.6); 7.988 (13.7); 7.892 (5.8); 7.888 (6.7); 7.875 (7.0); 7.870 (11.6); 7.866 (8.6); 7.852 (6.9); 7.848 (7.4); 7.815 (0.5); 7.805 (0.5); 7.675 (0.5); 7.670 (0.5); 7.652 (0.9); 7.631 (0.6); 7.439 (10.0); 7.432 (10.6); 7.417 (9.9); 7.410 (10.2); 7.394 (1.4); 7.373 (1.0); 7.264 (14.9); 7.242 (13.8); 7.158 (0.6); 7.149 (0.5); 7.136 (0.6); 7.129 (0.4); 7.060 (1.1); 7.053 (1.2); 7.038 (1.1); 7.030 (1.2); 6.922 (0.8); 6.910 (1.0); 6.907 (1.0); 6.892 (0.8); 6.823 (8.5); 6.806 (16.0); 6.789 (8.1); 6.005 (1.9); 5.753 (2.1); 3.978 (0.3); 3.959 (0.4); 3.933 (0.9); 3.823 (0.3); 3.510 (0.3); 3.316 (115.5); 3.212 (0.3); 3.193 (0.4); 3.179 (0.4); 3.152 (0.6); 3.120 (0.3); 3.082 (1.7); 3.072 (0.5); 2.989 (0.4); 2.972 (0.6); 2.959 (0.8); 2.939 (0.4); 2.928 (0.6); 2.875 (2.5); 2.697 (1.3); 2.670 (1.8); 2.501 (273.6); 2.425 (0.5); 2.328 (1.8); 1.313 (0.4); 1.295 (0.8); 1.277 (0.6); 1.258 (0.6); 1.235 (1.5); 1.209 (0.5); 1.192 (0.4); 1.147 (0.4); 1.124 (0.7); 1.106 (1.2); 1.088 (0.7); 1.060 (0.5); 1.044 (0.9); 1.035 (0.6); 1.027 (0.6); 1.017 (0.8); 0.999 (0.4); 0.852 (0.3); 0.146 (1.7); 0.054 (0.3); 0.000 (347.9); −0.150 (1.8).

Starting Materials of the Formula (IV)

The compounds (IV-6) to (IV-11), (IV-13), (IV-17) to (IV-21) and (IV-23) to (IV-28) listed in Table 1 were prepared by the variant described in Examples 1 and 2 (cf. in each case Step 1, Methods A and B); however, alternatively they can also be obtained by a boronic acid coupling reaction, as described for Example 3 (cf. Step 1, Variant B) and compound (IV-4).

1,2-Dihydro-2-oxo-1-(6-chloropyridin-3-yl)-3-pyridinecarbonitrile (IV-4)

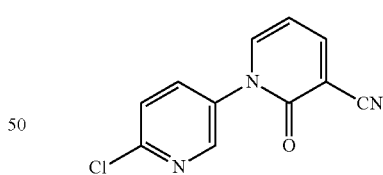

600.5 mg (5.0 mmol) of 1,2-dihydro-2-oxo-3-pyridinecarbonitrile were stirred in a mixture of 100 ml of dichloromethane and 15 ml of N,N-dimethylformamide, and 1.8 g (10.0 mmol) of copper(I) acetate, 0.8 ml of pyridine and 1.5 g (10 mmol) of 6-chloro-3-pyridinylboronic acid were added in succession. 4 Å molecular sieve was then added, and the mixture was stirred vigorously for several days. Ammonium hydroxide solution was then added to the reaction mixture, resulting in the precipitation of a greasy residue. The supernatant was decanted off and the oil that remained was washed. The mixture was then concentrated under reduced pressure on a rotary evaporator and the residue that remained was purified by column chromatography on silica gel (mobile phase: cyclohexane-acetone gradient). This gave 95 mg (98.5-99.0% pure, 4.0% yield) of 1,2-dihydro-2-oxo-1-(6-chloropyridin-3-yl)-3-pyridinecarbonitrile.

Log P value (HCOOH)=1.00

$^1$H-NMR (400.0 MHz, d$_6$-DMSO): δ=8.588 (13.2); 8.582 (13.2); 8.319 (9.0); 8.314 (10.9); 8.301 (9.4); 8.296 (9.7); 8.157 (9.7); 8.152 (9.7); 8.140 (10.2); 8.135 (9.3); 8.101 (9.3); 8.094 (9.1); 8.080 (10.4); 8.073 (10.1); 7.761 (14.8); 7.741 (12.6); 7.740 (12.9); 6.582 (9.4); 6.565 (16.0); 6.547 (8.9); 5.753 (0.9); 3.431 (0.3); 3.329 (62.1); 2.675 (1.6); 2.670 (2.2); 2.666 (1.7); 2.510 (144.3); 2.506 (277.1); 2.501 (361.1); 2.497 (269.3); 2.333 (1.7); 2.328 (2.3); 2.324 (1.7); 2.086 (3.9); 1.234 (0.4); 1.056 (0.4); 0.008 (1.9); 0.000 (40.8); −0.008 (1.9).

The compounds (IV-12), (IV-14) to (IV-16) and (IV-22) listed in Table 1 were also synthesized by boronic acid coupling reaction.

6'-Trifluoromethyl-[3-fluoro-1(2H), 3'-bipyridin]-2-one (IV-5)

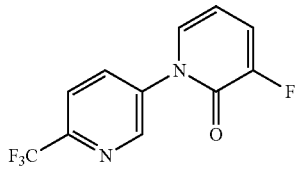 [SMILES: O=c1c(F)cccn1-c1ccc(C(F)(F)F)nc1]

295 mg (0.83 mmol) of 1-chloromethyl-4-fluoro-1,4-diazoniabicyclo[2.2.2]octane bis(tetrafluoroborate) (Selectfluor™) were added to 200 mg (0.83 mmol) of 6'-trifluoromethyl-[1(2H),3'-bipyridin]-2-one (IV-1) in 40 ml of acetonitrile, and the mixture was stirred at 60° C. for about 18 hours. For work-up, the reaction was filtered and concentrated under reduced pressure and the residue that remained was purified by column chromatography on silica gel (mobile phase: cyclohexane-acetone gradient). This gave 19 mg (80.0% pure, 7.0% yield) of 6'-trifluoromethyl-[3-fluoro-1(2H),3'-bipyridin]-2-one (IV-4) and 78 mg (80.0% pure, 27.1% yield) of 5,6-dihydro-5-fluoro-6-hydroxy-1-(6-trifluoromethylpyridin-3-yl)-2(1H)-pyridinone as a diastereomer mixture.

$^1$H-NMR (400.0 MHz, d$_6$-DMSO): δ=8.935 (12.4); 8.930 (12.8); 8.821 (1.6); 8.816 (1.6); 8.768 (0.4); 8.319 (6.2); 8.313 (6.6); 8.298 (7.8); 8.292 (8.0); 8.152 (16.0); 8.142 (1.4); 8.131 (12.7); 8.120 (1.4); 8.115 (1.2); 8.077 (0.3); 8.053 (2.2); 8.032 (1.5); 7.691 (9.3); 7.673 (9.6); 7.584 (4.7); 7.580 (4.6); 7.565 (5.2); 7.560 (5.9); 7.558 (5.9); 7.554 (4.9); 7.539 (4.9); 7.535 (4.6); 7.402 (1.8); 7.384 (1.9); 7.242 (0.3); 6.731 (0.4); 6.713 (0.6); 6.694 (0.4); 6.419 (4.5); 6.407 (5.0); 6.401 (8.2); 6.389 (8.2); 6.383 (4.8); 6.371 (4.3); 5.576 (0.5); 5.554 (0.8); 5.535 (0.5); 5.401 (0.4); 5.288 (0.4); 4.545 (0.5); 3.318 (78.6); 2.671 (1.1); 2.666 (0.9); 2.506 (131.3); 2.502 (172.3); 2.497 (130.5); 2.333 (0.8); 2.328 (1.1); 2.324 (0.8); 2.117 (1.5); 2.073 (0.5); 1.235 (0.3); 1.141 (3.4); 0.000 (4.0).

$^{13}$C-NMR (600 MHz, DMSO-d$_6$, ppm) δ=105.4; 122.1; 122.2; 134.2; 137.3; 149.2 (6×=CH—, hetaryl); 122.5 (hetaryl-CF$_3$); 140.1; 147.8 (2×hetaryl-C); 153.2 (=C—F); 156.8 (C=O) ppm.

5,6-Dihydro-5-fluoro-6-hydroxy-1-(6-trifluoromethyl-pyridin-3-yl)-2(1H)-pyridinone as diastereomer mixture $^{13}$C-NMR (600 MHz, DMSO-d$_6$, ppm) δ=82.5; 83.7 (2×Ĉ—OH); 83.8, 86.4 (2×C—F); 124.9; 130.5; 135.0; 140.2 (2×2=CH—, hetaryl); 122.6 (1×hetaryl-CF$_3$); 140.9; 141.4 (2×hetaryl-C); 145.9 (1×hetaryl-C); 162.6; 163.3 (2× C=O) ppm.

6'-Heptafluoropropyl-[1(2H),3'-bipyridin]-2-one (IV-31)

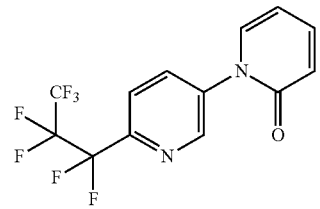 [SMILES: O=c1ccccn1-c1ccc(C(F)(F)C(F)(F)C(F)(F)F)nc1]

Under protective gas atmosphere (argon), 0.28 ml (2 mmol) of heptafluoro-1-iodopropane and 2 ml of DMF were added to 100 mg (0.39 mmol) of 6'-bromo-[1(2H),3'-bipyridin]-2-one (IV-2) and 633 mg (10 mmol) of copper powder in a closed 5-ml-microwave vessel. The reaction mixture was then stirred at 100° C. for 3.5 hours, cooled to room temperature, stirred in 20 ml of aqueous 1M ammonia solution and extracted with 20 ml of dichloromethane. The organic phase was separated off and then concentrated under reduced pressure, and the residue that remained was purified by preparative HPLC. This gave 44 mg (95% pure, 31% yield) of the 6'-heptafluoropropyl-[1(2H),3'-bipyridin]-2-one.

Log P value (HCOOH)=2.260

$^1$H-NMR (400.0 MHz, CDCl$_3$): δ=8.80 (d, 2.2 Hz, 1H), 8.09 (dd, 8.7, 2.6 Hz, 1H), 7.84 (d, 8.7 Hz, 1H), 7.46 (m, 1H), 7.35 (dd, 7.0, 1.7 Hz, 1H), 6.70 (d, 9.4 Hz, 1H), 6.35 (dd, 7.0, 1.2 Hz, 1H) ppm.

$^{13}$C-NMR (600 MHz, CDCl$_3$, ppm) δ=161.7, 147.2, 147.1 (t, 25.7 Hz), 140.6, 139.5 (t, 1.8 Hz), 136.4, 135.6, 122.6 (t, 4.5 Hz), 122.4, 117.9 (qt, 287.8, 31.6 Hz), 112.6 (tt, 259.7, 35.1 Hz), 108.8 (m), 107.1.

6'-(1,1,1,2,3,3,3-Heptafluoropropyl)-[1(2H), 3'-bipyridin]-2-one (IV-32)

was obtained analogously from:

100 mg (0.39 mmol) of 6'-bromo-[1(2H), 3'-bipyridin]-2-one (IV-2), 633 mg (10 mmol) of copper powder, 0.28 ml (2 mmol) of heptafluoro-2-iodopropane and 2 ml of N,N-dimethylformamide (DMF).

This gave 48.5 mg (95% pure, 34% yield) of the 6'-(1,1,1,2,3,3,3-heptafluoropropyl)-[1(2H), 3'-bipyridin]-2-one.

6'-Pentafluoroethyl-[1(2H), 3'-bipyridin]-2-one (IV-33)

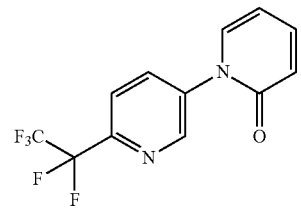 [SMILES: O=c1ccccn1-c1ccc(C(F)(F)C(F)(F)F)nc1]

At room temperature, 2 ml of a 0.4M solution of CuC$_2$F$_5$ in DMF (2 equivalents) were added to 100 mg (0.39 mmol) of 6'-bromo-[1(2H),3'-bipyridin]-2-one (IV-2), and the reaction mixture was stirred initially at room temperature for 15 hours and then at 70° C. for 4 hours. 20 ml of methyl tert-butyl ether (MTBE) and 1 ml of a 33% strength aqueous ammonia solution were then added in the presence of atmospheric oxygen. The organic phase was separated off and the aqueous phase was washed with 20 ml of MTBE. The combined organic phases were concentrated under reduced pressure, and the residue that remained was purified by preparative HPLC. This gave 90 mg (99.0% pure, 78% yield) of the 6'-pentafluoroethyl-[1(2H), 3'-bipyridin]-2-one.

The CuC$_2$F$_5$ reagent was prepared from C$_2$F$_5$H on a 20-mmol-scale, neutralized with Et$_3$N.3HF (0.33 equiv. per equiv. of CuC$_2$F$_5$), and an additional amount of Et$_3$N.3HF (0.2 equiv. per equiv. of CuC$_2$F$_5$) was then added, as published in: A. Lishchynskyi, V. V. Grushin, *J. Am. Chem. Soc.* 135, 12584, 2013. The reagent was not prepared in a glove box, but by applying the "Schlenk method".

Log P value (HCOOH)=1.94

$^1$H-NMR (400.0 MHz, CDCl$_3$): δ=8.79 (d, 2.3 Hz, 1H), 8.08 (dd, 8.4, 2.3 Hz, 1H), 7.86 (d, 8.4 Hz, 1H), 7.46 (m, 1H), 7.34 (dd, 6.8, 1.7 Hz, 1H), 6.70 (d, 9.3 Hz, 1H), 6.36 (dd, 6.8, 0.9 Hz, 1H) ppm.

$^{13}$C-NMR (600 MHz, CDCl$_3$) δ=161.7, 147.3, 147.2 (t, 26.1 Hz), 140.7, 139.5 (t, 1.7 Hz), 136.4, 135.7, 122.3, 122.2 (tq, 4.4, 1.0 Hz), 118.8 (qt, 288.7, 39.0 Hz), 111.0 (tq, 255.5, 38.2 Hz), 107.1 ppm.

Example 24: [1-[6-(3-Chloro-1,2,4-triazol-1-yl)pyridin-3-yl]-2-(1H)-pyridinylidene]cyanamide

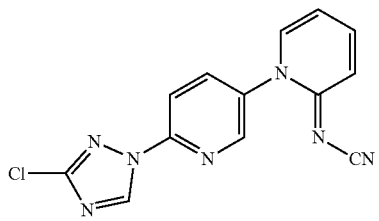 [SMILES: N#C/N=c1\ccccn1-c1ccc(-n2cnc(Cl)n2)nc1]

Step 1: Synthesis of Compounds of the Formula (IV)

6'-(3-Chloro-1,2,4-triazol-1-yl)-[1(2H), 3'-bipyridin]-2-one (IV-29)

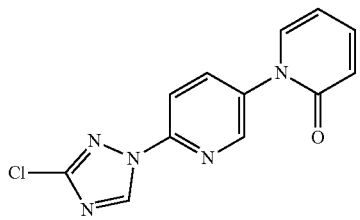 [SMILES: O=c1ccccn1-c1ccc(-n2cnc(Cl)n2)nc1]

250.0 mg (1.21 mmol) of 6'-chloro-[1(2H),3'-bipyridin]-2-one (IV-14) were stirred in 10 ml of N,N-dimethylformamide (DMF), 438.3 mg (4.23 mmol) of 3-chloro-1,2,4-triazole, 496.0 mg (3.58 mmol) of potassium carbonate, 29.9 mg (0.15 mmol) of copper(I) iodide and 65.4 mg (0.46 mmol) of N,N-dimethylcyclohexane-1,2-diamine were added and the mixture was stirred at 110° C. for 2 days. After cooling, the reaction mixture was extracted with saturated sodium chloride solution and ethyl acetate. For work-up, the organic phase was dried and concentrated under reduced pressure and the residue that remained was purified by column chromatography on silica gel (mobile phase: cyclohexane acetone gradient). This gave 38 mg (100.0% pure, 11.4% yield) of 6'-(3-chloro-1,2,4-triazol-1-yl)-[1(2H),3'-bipyridin]-2-one.

Log P value (HCOOH)=1.23

LC-MS (ESI positive)=274.0 (M$^+$) C$_{12}$H$_8$ClN$_5$O (273.7 g/mol)

$^1$H-NMR (400.0 MHz, DMSO-d$_6$): δ=6.40; 6.55; 7.57; 7.79; 7.97; 8.22 (m, 6H, hetaryl-H); 8.67 (d, 1H, hetaryl-H); 9.51 (s, 1H, hetaryl-H) ppm.

The compound (IV-30) listed in Table 2 was obtained analogously.

Step 2: Synthesis of Compounds of the Formula (VI)

6'-(3-Chloro-1,2,4-triazol-1-yl)-[1(2H), 3'-bipyridine]-2-thione (VI-5)

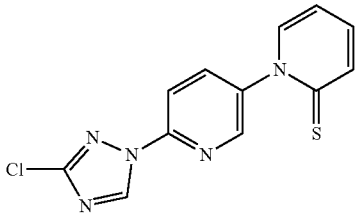 [SMILES: S=c1ccccn1-c1ccc(-n2cnc(Cl)n2)nc1]

190.0 mg (0.69 mmol) of 6'-(3-chloro-1,2,4-triazol-1-yl)-[1(2H),3'-bipyridin]-2-one (IV-29) and 583.2 mg (6.94 mmol) of sodium bicarbonate were stirred in 10 ml of 1,4-dioxane. After addition of 771.5 mg (18.7 mmol) of diphosphorus pentasulphide, the reaction was stirred at 80° C. for about 18 hours. For work-up, the solvent was removed under reduced pressure and the residue that remained was shaken with dichloromethane and water. The organic phase was removed, dried and concentrated under reduced pressure. The residue that remained was purified by column chromatography on silica gel (mobile phase gradient:cyclohexane:acetone gradient). This gave 127 mg (99% pure, 62.5% yield) of 6'-(3-chloro-1,2,4-triazol-1-yl)-[1(2H),3-bipyridine]-2-thione.

Log P value (neutral)=1.58

LC-MS (ESI positive)=290.0 (M$^+$) C$_{12}$H$_8$ClN$_5$S (289.7 g/mol)

$^1$H-NMR (400.0 MHz, DMSO-d$_6$): δ=6.94; 7.50; 7.58; 7.98; 8.13; 8.21 (m, 6H, hetaryl-H); 8.66 (d, 1H, hetaryl-H); 9.53 (s, 1H, hetaryl-H) ppm.

The compound (VI-6) listed in Table 3 was obtained analogously.

Step 3: Synthesis of Compounds of the Formula (VII)

[1-[6-(3-Chloro-1,2,4-triazol-1-yl)pyridin-3-yl]-2-(methylthio)pyridinium iodide (VII-2)

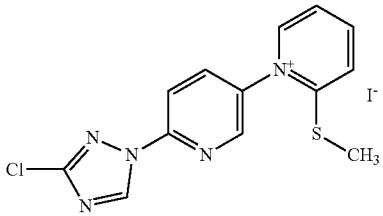 [SMILES: CSc1cccc[n+]1-c1ccc(-n2cnc(Cl)n2)nc1 ; [I-]]

100.0 mg (0.34 mmol) of 6'-(3-chloro-1,2,4-triazol-1-yl)-[1(2H), 3'-bipyridine]-2-thione (VI-5) (synthesis according to Step 2) were initially charged in 5 ml of acetonitrile, 489.8 g (3.45 mmol) of methyl iodide were added and the mixture was stirred at room temperature for about 18 hours. LC-MS control showed that the reaction had ended. The reaction was then concentrated under reduced pressure and the crude product (VII-2) that remained was reacted without further purification in the next reaction step.

LC-MS (ESI positive)=304.0 (M$^+$-I) $C_{13}H_{11}ClN_5SI$ (431.6 g/mol)

[1-[6-(3-Trifluoromethyl-1,2,4-triazol-1-yl)pyridin-3-yl]-2-(methylthio)pyridinium iodide (VII-3)

was obtained analogously from:
450.0 mg (1.39 mmol) of 6'-(3-trifluoromethyl-1,2,4-triazol-1-yl)-[1(2H),3'-bipyridine]-2-thione (VI-6),
1981.6 mg (13.9 mmol) of methyl iodide and 20 ml of acetonitrile.

LC-MS (ESI positive)=337.1 (M$^+$-I) $C_{15}H_{12}F_3N_4SI$ (464.2 g/mol)

Step 4: [1-[6-(3-Chloro-1,2,4-triazol-1-yl)pyridin-3-yl]-2-(1H)-pyridinylidene]cyanamide 43.5 mg (0.46 mmol) of sodium hydrogencyanamide were added to 146.7 mg (0.34 mmol) of [1-[6-(3-chloro-1,2,4-triazol-1-yppyridin-3-yl]-2-(methylthio)pyridinium iodide (VII-2), (synthesis according to Step 3), dissolved in 10 ml of acetonitrile. The reaction mixture was then stirred at room temperature for 18 hours. Control by thin-layer chromatogram (mobile phase:cyclohexane:acetone) showed that the reaction had ended. For work-up, the reaction was concentrated under reduced pressure and the residue that remained was purified by column chromatography on silica gel (mobile phase gradient: cyclohexane:acetone gradient). This gave 53 mg (90% pure, 47.1% yield) of [1-[6-(3-chloro-1,2,4-triazol-1-yl)pyridin-3-yl]-2-(1H)-pyridiny lidene]cyanamide.

Log P value (neutral)=1.39

LC-MS (ESI positive)=298.0 (M$^+$) $C_{13}H_8ClN_7$ (297.7 g/mol)

$^1$H-NMR (400.0 MHz, DMSO-d$_6$): δ=6.83; 7.28; 7.88, 8.02 (m, 6H, hetaryl-H); 8.30 (d, 1H, hetaryl-H); 9.53 (s, 1H, hetaryl-H) ppm.

Example 25: [1-[[6-(3-Trifluoromethylpyrazol-1-yl) pyridin-3-yl]-2-(1H)-pyridinylidene]cyanamide

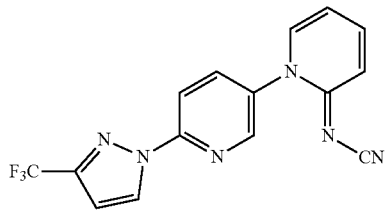 [SMILES: N#C/N=c1\ccccn1-c1ccc(-n2ccc(C(F)(F)F)n2)nc1]

Analogously to Example 24, 645.3 mg (1.39 mmol) of [1-[6-(3-trifluoromethyl-1,2,4-triazol-1-yl)pyridin-3-yl]-2-(methylthio)pyridinium iodide (VII-3) (synthesis according to Step 3), 177.9 mg (2.78 mmol) of sodium hydrogen cyanamide and 10 ml of acetonitrile were used. This gave 406 mg (100% pure, 88.4% yield) of [1-[6-(3-trifluoromethyl-1,2,4-triazol-1-yl)pyridin-3-yl]-2-(1H)-pyridinylidene]cyanamide.

Log P value (neutral)=2.23

LC-MS (ESI positive)=231.1 (M$^+$+H) $C_{13}H_8ClN_7$ (230.2 g/mol)

$^{13}$C- with $^1$H-dec. (CPD) NMR (150 MHz, CDCl$_3$, ppm) δ=111.7; 113.9; 137.7; 139.4; 147.4; 119.4; 140.3; 142.8; 151.3 (9×=CH—, pyridine); 164.0 (—N=C-pyridine); 117.9 (CN); 122.2 (hetaryl-CF$_3$); 107.5; 130.7; 145.5 (3×=CH—, pyrazine) ppm.

TABLE 1

Analytical data for compounds of the formula (IV)

| Example No. | | R | $^1$H NMR [δ (ppm)] or logP value (HCOOH) |
|---|---|---|---|
| IV-6 | (cyclohexadienyl) | 4-CF$_3$-phenyl | $^1$H-NMR (400.0 MHz, d$_6$-DMSO): δ = 7.906 (13.2); 7.885 (16.0); 7.718 (5.9); 7.713 (6.6); 7.700 (6.8); 7.690 (15.7); 7.669 (12.7); 7.563 (3.7); 7.558 (3.8); 7.547 (4.1); 7.541 (6.4); 7.535 (4.1); 7.524 (4.1); 7.519 (3.9); 6.528 (8.4); 6.505 (7.9); 6.379 (4.3); 6.377 (4.4); 6.362 (8.2); 6.360 (8.2); 6.346 (4.1); 6.343 (4.1); 3.318 (44.4); 2.671 (0.6); 2.666 (0.5); 2.506 (69.0); 2.501 (91.5); 2.497 (68.5); 2.328 (0.6); 2.324 (0.4); 1.398 (0.5); 0.000 (3.3); LogP value (HCOOH) = 1.85 |

TABLE 1-continued

Analytical data for compounds of the formula (IV)

| Example No. | $A^1$-$A^2$-$A^3$-$A^4$ | R | $^1$H NMR [δ (ppm)] or logP value (HCOOH) |
|---|---|---|---|
| IV-7 | (butadienyl) | 3-Cl-4-CF$_3$-phenyl | $^1$H-NMR (400.0 MHz, d$_6$-DMSO): δ = 8.314 (0.4); 8.025 (14.2); 8.004 (16.0); 7.942 (14.9); 7.939 (15.9); 7.746 (8.7); 7.741 (9.8); 7.728 (9.2); 7.724 (9.9); 7.673 (8.9); 7.652 (7.9); 7.569 (5.5); 7.564 (5.6); 7.552 (6.1); 7.547 (9.3); 7.541 (6.2); 7.529 (6.1); 7.524 (5.9); 6.536 (12.3); 6.513 (11.8); 6.390 (6.4); 6.387 (6.7); 6.373 (12.1); 6.370 (12.4); 6.356 (6.2); 6.353 (6.2); 3.318 (93.2); 2.675 (0.9); 2.671 (1.2); 2.666 (0.9); 2.506 (147.9); 2.502 (195.7); 2.497 (149.0); 2.333 (0.9); 2.328 (1.3); 2.324 (1.0); 2.086 (0.6); 0.000 (4.5); LogP value (HCOOH) = 2.23 |
| IV-8 | (butadienyl) | 5-Br-3-CH$_3$-pyridin-2-yl | $^1$H-NMR (600.1 MHz, CD$_3$CN): δ = 8.504 (13.2); 8.503 (13.7); 8.500 (14.4); 8.499 (13.9); 7.995 (15.0); 7.994 (15.8); 7.992 (12.2); 7.991 (16.0); 7.990 (15.3); 7.528 (8.2); 7.524 (8.9); 7.517 (8.7); 7.513 (10.6); 7.512 (10.3); 7.508 (9.5); 7.501 (8.8); 7.498 (9.3); 7.394 (9.8); 7.393 (10.3); 7.391 (10.3); 7.390 (9.9); 7.386 (1.3); 7.383 (10.3); 7.382 (10.8); 7.379 (10.5); 7.378 (9.8); 7.371 (0.4); 6.498 (9.5); 6.4963 (12.6); 6.4957 (12.8); 6.494 (10.3); 6.482 (9.4); 6.481 (12.3); 6.480 (12.4); 6.479 (9.9); 6.328 (8.6); 6.326 (8.7); 6.317 (14.5); 6.315 (14.6); 6.309 (1.0); 6.306 (8.5); 6.304 (8.4); 6.064 (1.4); 2.247 (0.7); 2.142 (80.6); 2.141 (126.1); 2.140 (80.7); 2.131 (93.6); 2.118 (1.3); 2.117 (1.7); 2.115 (1.1); 2.109 (1.6); 2.058 (0.3); 2.054 (0.6); 2.050 (0.9); 2.046 (0.6); 2.032 (0.7); 1.963 (4.0); 1.955 (9.4); 1.951 (10.5); 1.947 (60.7); 1.943 (107.7); 1.939 (156.1); 1.935 (106.6); 1.931 (53.4); 1.922 (1.2); 1.832 (0.3); 1.828 (0.6); 1.824 (0.9); 1.820 (0.6); 1.437 (2.0); 0.005 (0.4); 0.000 (14.9); −0.006 (0.5); LogP value (HCOOH) = 1.31 |
| IV-9 | (butadienyl) | 2-F-3-CH$_3$-pyridin-5-yl | $^1$H-NMR (400.0 MHz, d$_6$-DMSO): δ = 8.138 (3.1); 8.025 (1.8); 8.020 (1.6); 8.018 (1.7); 8.003 (1.8); 7.998 (1.6); 7.996 (1.5); 7.706 (2.2); 7.702 (2.3); 7.701 (2.3); 7.689 (2.3); 7.685 (2.3); 7.684 (2.3); 7.565 (1.5); 7.560 (1.5); 7.548 (1.7); 7.542 (2.4); 7.537 (1.6); 7.525 (1.7); 7.520 (1.5); 6.523 (3.0); 6.499 (2.9); 6.370 (1.7); 6.367 (1.8); 6.354 (3.1); 6.351 (3.2); 6.337 (1.6); 6.334 (1.6); 3.317 (54.5); 2.843 (0.3); 2.675 (0.4); 2.670 (0.5); 2.666 (0.4); 2.510 (29.5); 2.506 (59.5); 2.501 (79.5); 2.497 (59.4); 2.332 (0.4); 2.328 (0.5); 2.323 (0.4); 2.298 (16.0); 1.235 (0.6); 0.000 (3.0); LogP value (HCOOH) = 0.96 |
| IV-10 | (butadienyl) | 6-CF$_3$-pyridazin-3-yl | $^1$H-NMR (400.0 MHz, d$_6$-DMSO): δ = 8.514 (0.6); 8.490 (16.0); 8.466 (0.6); 8.066 (3.2); 8.048 (3.2); 7.666 (1.4); 7.661 (1.7); 7.643 (2.7); 7.638 (2.1); 7.626 (1.6); 7.621 (1.8); 6.623 (3.8); 6.600 (3.6); 6.513 (2.2); 6.496 (4.1); 6.479 (2.1); 3.317 (20.5); 2.671 (0.5); 2.502 (73.3); 2.328 (0.5); 0.000 (2.9); LogP value (HCOOH) = 1.27 |

TABLE 1-continued
Analytical data for compounds of the formula (IV)
| Example No. | 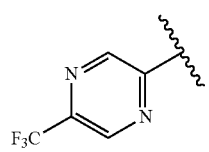 [SMILES: *c1cnc(C(F)(F)F)cn1] | R | $^1$H NMR [δ (ppm)] or logP value (HCOOH) |
|---|---|---|---|
| IV-11 |  | 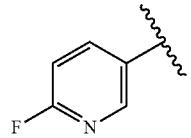 | $^1$H-NMR (400.0 MHz, d$_6$-DMSO): δ = 9.359 (15.2); 9.269 (16.0); 7.966 (6.7); 7.962 (7.5); 7.948 (7.0); 7.944 (7.5); 7.644 (4.2); 7.639 (4.4); 7.628 (4.6); 7.622 (6.9); 7.616 (4.8); 7.605 (4.7); 7.599 (4.5); 6.619 (9.9); 6.596 (9.3); 6.517 (5.3); 6.515 (5.2); 6.499 (9.8); 6.483 (5.1); 6.481 (4.9); 3.318 (68.9); 2.675 (0.6); 2.671 (0.8); 2.667 (0.6); 2.506 (99.8); 2.502 (130.3); 2.498 (99.1); 2.333 (0.7); 2.329 (0.9); 2.324 (0.7); 0.146 (0.4); 0.008 (3.0); 0.000 (70.1); −0.150 (0.4); LogP value (HCOOH) = 1.63 |
| IV-12 |  | 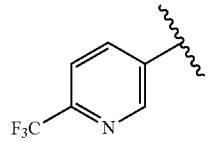 [SMILES: *c1ccc(C(F)(F)F)nc1] | $^1$H-NMR (400.0 MHz, d$_6$-DMSO): δ = 8.349 (11.8); 8.347 (12.4); 8.343 (13.0); 8.340 (12.9); 8.314 (0.9); 8.161 (7.4); 8.154 (7.0); 8.144 (7.9); 8.140 (9.0); 8.137 (8.4); 8.133 (8.1); 8.122 (7.8); 8.115 (7.4); 7.739 (9.8); 7.738 (10.5); 7.734 (11.4); 7.733 (10.9); 7.722 (10.3); 7.720 (11.0); 7.717 (11.3); 7.715 (11.0); 7.572 (8.1); 7.567 (7.9); 7.555 (8.6); 7.549 (11.7); 7.543 (8.4); 7.532 (8.8); 7.527 (8.3); 7.377 (11.6); 7.370 (11.8); 7.356 (11.1); 7.348 (11.1); 6.531 (14.0); 6.508 (13.3); 6.382 (8.7); 6.379 (8.8); 6.366 (16.0); 6.362 (15.9); 6.349 (8.4); 6.346 (8.2); 3.325 (108.1); 2.676 (0.7); 2.671 (1.0); 2.667 (0.7); 2.525 (2.1); 2.520 (3.2); 2.511 (54.7); 2.507 (114.6); 2.502 (154.2); 2.498 (111.7); 2.493 (53.8); 2.333 (0.7); 2.329 (1.0); 2.324 (0.7); 1.398 (0.5); 0.146 (0.5); 0.008 (3.2); 0.000 (106.0); −0.009 (3.5); −0.150 (0.5); LogP value (HCOOH) = 0.52 |
| IV-13 |  | 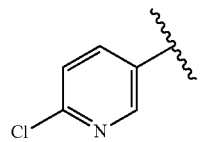 [SMILES: *c1ccc(Cl)nc1] | $^1$H-NMR (400.0 MHz, d$_6$-DMSO): δ = 8.948 (12.2); 8.943 (12.7); 8.848 (0.6); 8.369 (0.3); 8.348 (9.2); 8.343 (14.4); 8.336 (7.5); 8.330 (10.5); 8.325 (11.3); 8.321 (9.0); 8.315 (8.3); 8.216 (9.4); 8.211 (9.4); 8.199 (10.0); 8.194 (9.4); 8.175 (15.2); 8.154 (11.8); 7.975 (0.3); 7.959 (0.4); 7.934 (0.5); 6.622 (8.8); 6.605 (16.0); 6.587 (8.4); 5.753 (4.6); 3.320 (78.1); 3.202 (0.4); 3.004 (0.4); 2.671 (0.8); 2.627 (0.4); 2.573 (2.2); 2.506 (86.0); 2.502 (111.9); 2.497 (85.5); 2.328 (0.7); 1.235 (1.1); 0.000 (59.6) |
| IV-14 | | | $^1$H-NMR (400.0 MHz, d$_6$-DMSO): δ = 8.528 (13.4); 8.522 (13.6); 8.316 (0.5); 8.036 (10.8); 8.030 (10.5); 8.015 (12.2); 8.008 (11.9); 7.746 (6.7); 7.745 (7.1); 7.741 (7.7); 7.740 (7.3); 7.729 (7.1); 7.728 (7.5); 7.724 (7.7); 7.723 (7.3); 7.708 (16.0); 7.707 (15.9); 7.687 (14.0); 7.686 (13.9); 7.574 (5.4); 7.569 (5.3); 7.557 (5.8); 7.551 (7.6); 7.545 (5.6); 7.534 (5.9); 7.529 (5.5); 6.534 (9.6); 6.511 (8.9); 6.510 (8.9); 6.393 (5.9); 6.390 (5.8); 6.376 (10.6); 6.373 (10.4); 6.359 (5.7); 6.356 (5.5); 3.324 (87.8); 2.680 (0.4); 2.675 (0.8); 2.671 (1.2); 2.666 (0.9); 2.524 (2.6); 2.511 (65.4); 2.506 (134.7); 2.502 (179.2); 2.497 (129.6); 2.493 (62.2); 2.337 (0.4); 2.333 (0.8); |

TABLE 1-continued

Analytical data for compounds of the formula (IV)

| Example No. | A¹–A²–A³–A⁴ structure | R | ¹H NMR [δ (ppm)] or logP value (HCOOH) |
|---|---|---|---|
| | | | 2.328 (1.2); 2.324 (0.8); 2.086 (0.7); 1.397 (2.9); 0.008 (0.7); 0.000 (22.4); −0.009 (0.8); LogP value (HCOOH) = 0.67 |
| IV-15 | (pentadienyl) | 5-Cl-pyridin-3-yl | ¹H-NMR (400.0 MHz, $d_6$-DMSO): δ =10.468 (0.5); 8.734 (7.0); 8.659 (6.6); 8.318 (0.4); 8.213 (16.0); 7.771 (8.9); 7.768 (9.3); 7.755 (9.2); 7.751 (9.2); 7.578 (4.8); 7.573 (4.8); 7.561 (5.8); 7.556 (8.4); 7.550 (5.6); 7.538 (5.3); 7.534 (4.8); 7.267 (0.4); 6.959 (0.7); 6.542 (11.5); 6.518 (11.0); 6.394 (6.4); 6.377 (11.9); 6.360 (6.1); 5.671 (0.5); 3.330 (132.5); 2.891 (0.4); 2.731 (0.4); 2.671 (1.4); 2.502 (210.5); 2.329 (1.3); 0.000 (3.9) |
| IV-16 | (pentadienyl) | 5,6-di-Cl-pyridin-3-yl | ¹H-NMR (400.0 MHz, $d_6$-DMSO): δ = 8.561 (14.3); 8.556 (16.0); 8.454 (15.5); 8.448 (14.1); 8.314 (0.5); 7.771 (6.7); 7.766 (7.2); 7.754 (7.1); 7.749 (7.2); 7.582 (4.1); 7.577 (4.2); 7.566 (4.5); 7.560 (6.9); 7.554 (4.5); 7.543 (4.6); 7.537 (4.4); 6.547 (9.4); 6.524 (8.9); 6.407 (4.9); 6.404 (5.0); 6.390 (9.3); 6.387 (9.2); 6.373 (4.8); 6.370 (4.6); 3.317 (110.4); 2.671 (1.2); 2.506 (146.8); 2.502 (191.5); 2.497 (142.5); 2.332 (0.9); 2.328 (1.2); 2.086 (0.7); 1.398 (2.8); 0.146 (0.5); 0.008 (4.2); 0.000 (106.3); −0.008 (4.5); −0.149 (0.5); LogP value (HCOOH) = 1.50 |
| IV-17 | (methylpentadienyl) | 6-CF₃-pyridin-3-yl | ¹H-NMR (400.0 MHz, $d_6$-DMSO): δ = 8.885 (3.1); 8.880 (3.2); 8.254 (1.5); 8.249 (1.5); 8.234 (2.0); 8.228 (2.0); 8.107 (4.2); 8.086 (3.2); 7.665 (1.8); 7.662 (1.9); 7.648 (1.9); 7.645 (2.0); 7.471 (1.3); 7.469 (1.8); 7.467 (1.8); 7.464 (1.5); 7.455 (1.5); 7.452 (1.9); 7.450 (1.9); 7.447 (1.4); 6.353 (2.3); 6.336 (4.4); 6.319 (2.2); 3.317 (35.1); 2.524 (0.5); 2.510 (12.8); 2.506 (26.3); 2.501 (36.2); 2.497 (28.1); 2.493 (14.5); 2.064 (16.0); 1.398 (0.6); LogP value (HCOOH) = 1.69 |
| IV-18 | (CF₃-pentadienyl) | 6-CF₃-pyridin-3-yl | ¹H-NMR (400.0 MHz, $d_6$-DMSO): δ = 8.945 (11.4); 8.941 (11.8); 8.570 (0.4); 8.340 (5.6); 8.335 (5.8); 8.319 (7.0); 8.314 (7.6); 8.160 (14.3); 8.150 (9.1); 8.139 (16.0); 8.132 (11.9); 8.110 (7.4); 7.924 (0.4); 7.906 (0.4); 7.799 (0.4); 7.784 (0.6); 7.691 (0.3); 6.582 (5.5); 6.564 (10.3); 6.547 (5.2); 3.351 (0.5); 3.317 (71.3); 2.671 (1.7); 2.502 (275.0); 2.328 (1.6); 2.086 (1.0); 1.398 (1.4); 0.000 (11.7); LogP value (HCOOH) = 2.14 |
| IV-19 | (CF₃-pentadienyl) | 6-CF₃-pyridin-3-yl | ¹H-NMR (600.1 MHz, CD₃CN): δ = 8.810 (11.7); 8.806 (12.1); 8.292 (1.9); 8.287 (2.0); 8.119 (6.1); 8.118 (6.3); 8.117 (3.9); 8.115 (6.3); 8.114 (6.2); 8.105 (7.4); 8.104 (7.5); 8.101 (7.6); 8.100 (7.4); 8.004 (2.4); 8.001 (6.7); 8.000 (7.9); 7.999 (9.3); 7.998 (9.9); 7.997 (10.2); 7.996 (9.7); 7.995 (8.3); 7.994 (7.1); 7.9724 (16.0); 7.9717 (15.9); 7.966 (0.8); 7.963 (0.7); 7.959 (13.3); 7.958 (13.1); 7.671 (9.0); 7.667 (8.9); 7.655 (9.2); 7.650 (9.2); 7.635 (2.3); 7.621 (2.5); 7.342 (1.1); 7.341 (1.1); 7.337 (1.1); 7.336 (1.1); 7.327 |

TABLE 1-continued

Analytical data for compounds of the formula (IV)

| Example No. | A¹–A²–A³–A⁴ | R | ¹H NMR [δ (ppm)] or logP value (HCOOH) |
|---|---|---|---|
| | | | (1.0); 7.326 (1.0); 7.323 (1.0); 7.322 (1.0); 6.680 (8.4); 6.679 (11.5); 6.678 (8.6); 6.664 (8.1); 6.662 (11.1); 6.661 (8.3); 2.136 (6.8); 2.054 (0.4); 2.050 (0.6); 2.046 (0.4); 1.963 (2.7); 1.955 (5.9); 1.951 (6.4); 1.947 (37.9); 1.943 (67.4); 1.939 (98.7); 1.935 (66.9); 1.931 (33.3); 1.926 (1.3); 1.922 (0.5); 1.828 (0.4); 1.824 (0.6); 1.820 (0.4); 1.437 (1.6); 0.000 (1.6); LogP value (HCOOH) = 2.35 |
| IV-20 | | | ¹H-NMR (400.0 MHz, d₆-DMSO): δ = 8.734 (0.4); 8.729 (0.4); 8.511 (0.4); 8.505 (0.4); 8.475 (14.9); 8.470 (16.0); 8.329 (8.8); 8.324 (8.2); 8.313 (0.8); 8.306 (8.7); 8.301 (8.2); 7.763 (6.3); 7.758 (6.6); 7.746 (6.7); 7.741 (6.6); 7.586 (4.4); 7.581 (4.4); 7.570 (4.7); 7.563 (6.8); 7.558 (4.7); 7.546 (4.8); 7.541 (4.5); 6.553 (8.9); 6.530 (8.5); 6.412 (4.8); 6.409 (4.9); 6.396 (8.8); 6.393 (9.1); 6.379 (4.6); 6.376 (4.7); 3.316 (127.9); 2.675 (0.9); 2.670 (1.2); 2.666 (0.9); 2.523 (3.1); 2.510 (68.4); 2.506 (139.4); 2.501 (187.1); 2.497 (138.9); 2.492 (69.8); 2.332 (0.8); 2.328 (1.2); 2.323 (0.9); 1.398 (1.2); 1.235 (0.4); 0.008 (0.4); 0.000 (11.2); −0.008 (0.4); LogP value (HCOOH) = 1.18 |
| IV-21 | | | ¹H-NMR (601.6 MHz, d₆-DMSO): δ = 8.793 (0.4); 8.790 (0.4); 8.734 (14.3); 8.730 (13.9); 8.529 (0.4); 8.527 (0.3); 8.518 (0.5); 8.514 (0.6); 8.508 (16.0); 8.504 (14.8); 7.682 (4.8); 7.680 (5.4); 7.678 (5.9); 7.677 (5.3); 7.670 (5.1); 7.669 (5.7); 7.667 (5.9); 7.666 (5.2); 7.595 (4.3); 7.592 (4.3); 7.588 (0.6); 7.584 (4.7); 7.581 (5.6); 7.580 (5.7); 7.576 (4.6); 7.572 (0.7); 7.569 (4.8); 7.565 (4.5); 6.546 (5.3); 6.545 (7.2); 6.544 (7.4); 6.543 (5.5); 6.530 (5.6); 6.529 (7.1); 6.527 (5.5); 6.400 (4.9); 6.398 (4.6); 6.389 (8.7); 6.387 (8.3); 6.382 (0.7); 6.378 (4.9); 6.376 (4.4); 3.339 (0.6); 3.321 (493.6); 3.294 (0.7); 2.616 (0.6); 2.613 (0.8); 2.610 (0.6); 2.522 (1.3); 2.519 (1.7); 2.516 (1.7); 2.507 (41.7); 2.504 (88.7); 2.501 (120.8); 2.498 (87.6); 2.495 (41.6); 2.388 (0.6); 2.385 (0.8); 2.382 (0.6); 2.085 (2.1); 1.398 (0.8); 0.005 (0.7); 0.000 (23.4); −0.006 (0.8); LogP value (HCOOH) = 1.34 |
| IV-22 | | | ¹H-NMR (400.0 MHz, d₆-DMSO): δ = 8.917 (9.0); 8.912 (9.1); 8.313 (0.4); 8.295 (4.5); 8.289 (4.5); 8.274 (5.8); 8.268 (5.7); 8.126 (16.0); 8.119 (7.7); 8.117 (7.7); 8.105 (12.7); 7.776 (3.1); 7.768 (3.0); 7.758 (3.4); 7.750 (5.7); 7.743 (3.2); 7.733 (3.3); 7.725 (2.9); 6.620 (5.2); 6.606 (5.4); 6.594 (5.1); 6.581 (5.0); 3.315 (81.8); 2.670 (0.8); 2.501 (120.0); 2.497 (96.2); 2.328 (0.8); 1.398 (1.0); 0.000 (5.5); LogP value (HCOOH) = 1.50 |

TABLE 1-continued
Analytical data for compounds of the formula (IV)
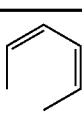
| Example No. | 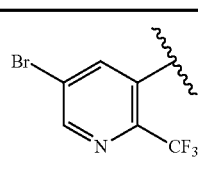 R | R | ¹H NMR [δ (ppm)] or logP value (HCOOH) |
|---|---|---|---|
| IV-23 | 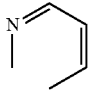 | 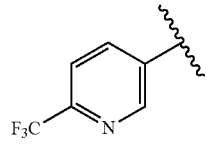 [SMILES: *c1ccc(C(F)(F)F)nc1] | ¹H-NMR (600.1 MHz, $d_6$-DMSO): δ = 9.140 (0.4); 9.137 (0.4); 9.066 (15.2); 9.063 (16.0); 8.664 (0.4); 8.662 (0.4); 8.637 (14.5); 8.636 (14.8); 8.6332 (15.3); 8.6326 (14.6); 7.727 (7.5); 7.724 (8.3); 7.716 (8.0); 7.713 (8.5); 7.700 (0.3); 7.597 (8.4); 7.593 (8.4); 7.586 (9.2); 7.582 (9.9); 7.581 (10.2); 7.578 (9.0); 7.570 (9.5); 7.567 (8.9); 7.561 (0.4); 7.560 (0.5); 7.556 (0.4); 6.518 (9.1); 6.5163 (12.7); 6.5158 (13.0); 6.514 (10.3); 6.507 (0.6); 6.502 (9.5); 6.501 (12.9); 6.500 (12.5); 6.499 (9.8); 6.488 (0.4); 6.487 (0.4); 6.485 (0.3); 6.389 (8.6); 6.387 (8.9); 6.383 (0.9); 6.378 (15.3); 6.376 (15.4); 6.370 (1.1); 6.367 (8.9); 6.365 (8.6); 6.361 (0.9); 6.359 (0.8); 5.756 (1.0); 3.319 (73.6); 2.616 (0.4); 2.613 (0.5); 2.610 (0.4); 2.522 (0.9); 2.519 (1.2); 2.516 (1.1); 2.507 (23.5); 2.504 (52.9); 2.501 (74.9); 2.498 (54.7); 2.495 (26.2); 2.388 (0.3); 2.385 (0.5); 2.382 (0.4); 0.000 (3.3); LogP value (HCOOH) = 1.68 |
| IV-24 | 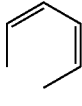 | 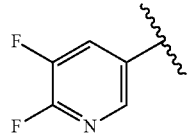 | ¹H-NMR (400.0 MHz, $d_6$-DMSO): δ = 9.074 (12.7); 9.069 (13.0); 8.407 (6.9); 8.402 (7.0); 8.386 (7.9); 8.381 (8.0); 8.314 (0.3); 8.182 (10.4); 8.178 (10.9); 8.172 (11.3); 8.169 (10.7); 8.107 (16.0); 8.086 (13.9); 7.582 (9.8); 7.572 (9.5); 7.558 (11.0); 7.548 (10.7); 7.181 (11.6); 7.177 (11.6); 7.157 (10.3); 7.153 (10.0); 3.319 (54.2); 2.672 (0.8); 2.507 (99.0); 2.503 (127.0); 2.499 (95.6); 2.330 (0.8); 1.398 (2.3); 0.146 (0.6); 0.008 (5.2); 0.000 (129.2); −0.150 (0.6); LogP value (HCOOH) = 1.56 |
| IV-25 | 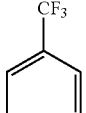 | 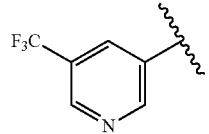 [SMILES: *c1cncc(C(F)(F)F)c1] | ¹H-NMR (400.0 MHz, $d_6$-DMSO): δ = 11.526 (1.0); 8.422 (4.3); 8.416 (4.6); 8.400 (4.8); 8.395 (7.4); 8.391 (5.1); 8.375 (4.3); 8.369 (4.5); 8.313 (0.5); 8.231 (9.3); 8.226 (16.0); 8.221 (8.9); 7.747 (7.2); 7.743 (7.7); 7.730 (7.6); 7.726 (7.7); 7.584 (5.1); 7.579 (5.1); 7.567 (5.5); 7.561 (8.0); 7.556 (5.4); 7.544 (5.6); 7.539 (5.3); 7.427 (2.4); 7.421 (2.7); 7.410 (2.5); 7.404 (4.2); 7.398 (3.0); 7.387 (2.5); 7.382 (3.0); 7.351 (3.6); 7.346 (3.2); 7.334 (3.8); 7.330 (3.2); 6.549 (10.4); 6.526 (9.9); 6.401 (5.6); 6.398 (5.7); 6.384 (10.4); 6.381 (10.3); 6.367 (5.4); 6.364 (5.3); 6.309 (5.6); 6.286 (5.4); 6.159 (2.7); 6.157 (2.8); 6.143 (5.2); 6.140 (5.2); 6.127 (2.6); 6.124 (2.6); 5.754 (0.4); 4.004 (1.1); 3.491 (0.5); 3.318 (147.8); 2.675 (0.9); 2.671 (1.2); 2.666 (0.9); 2.524 (2.8); 2.510 (73.4); 2.506 (153.1); 2.502 (204.9); 2.497 (148.4); 2.493 (71.6); 2.332 (0.9); 2.328 (1.2); 2.324 (0.9); 1.235 (0.3); 0.008 (0.6); 0.000 (18.7); −0.008 (0.6); LogP value (HCOOH) = 0.84 |
| IV-26 |  |  | LogP value (HCOOH) = 2.89 |

TABLE 1-continued

Analytical data for compounds of the formula (IV)

| Example No. | A¹–A²–A³–A⁴ | R | ¹H NMR [δ (ppm)] or logP value (HCOOH) |
|---|---|---|---|
| IV-27 | CH=C(CF₃)–CH=CH– | 2-(CF₃)-pyridin-5-yl | ¹H-NMR (601.6 MHz, d₆-DMSO): δ =19.973 (0.7); 8.938 (13.1); 8.934 (13.4); 8.319 (6.3); 8.315 (6.3); 8.305 (7.7); 8.301 (7.8); 8.254 (0.9); 8.249 (0.8); 8.154 (16.0); 8.140 (13.4); 8.075 (11.3); 8.063 (11.7); 7.709 (0.9); 7.694 (1.0); 6.997 (13.2); 6.677 (10.5); 6.674 (10.3); 6.665 (10.5); 6.662 (10.5); 3.309 (116.5); 2.616 (1.1); 2.613 (1.6); 2.610 (1.1); 2.522 (2.6); 2.519 (3.1); 2.516 (2.9); 2.507 (85.2); 2.504 (190.7); 2.501 (269.6); 2.498 (192.0); 2.495 (86.3); 2.385 (1.4); 2.382 (1.1); 0.097 (1.9); 0.005 (14.5); 0.000 (521.8); −0.006 (15.5); −0.100 (1.9); |
| IV-28 | CH=C(CF₃)–CH=CH– | 2-(CF₃)-pyridin-5-yl | ¹H-NMR (400.0 MHz, d₆-DMSO): δ = 9.063 (15.2); 9.061 (15.1); 8.994 (15.4); 8.988 (15.9); 8.474 (9.5); 8.470 (16.0); 8.465 (9.3); 8.317 (0.7); 7.830 (9.3); 7.828 (9.9); 7.825 (10.8); 7.823 (9.9); 7.812 (9.7); 7.811 (10.5); 7.807 (10.7); 7.806 (9.9); 7.598 (7.6); 7.593 (7.7); 7.581 (8.2); 7.575 (10.4); 7.570 (8.1); 7.558 (8.4); 7.553 (8.0); 6.563 (10.0); 6.560 (13.5); 6.558 (10.6); 6.538 (12.7); 6.535 (10.0); 6.421 (8.5); 6.418 (8.5); 6.404 (15.2); 6.401 (15.0); 6.387 (8.2); 6.384 (7.9); 3.330 (358.1); 2.680 (0.7); 2.676 (1.5); 2.671 (2.1); 2.667 (1.5); 2.662 (0.7); 2.525 (4.9); 2.520 (7.5); 2.511 (112.8); 2.507 (234.0); 2.502 (310.7); 2.498 (225.6); 2.493 (108.9); 2.338 (0.7); 2.333 (1.5); 2.329 (2.1); 2.324 (1.5); 2.320 (0.7); 1.398 (0.5); 0.008 (1.4); 0.000 (46.1); −0.009 (1.5); LogP value (HCOOH) = 1.21 |
| IV-30 | CH=CH–CH=CH– | 2-(3-CF₃-pyrazol-1-yl)-pyridin-5-yl | ¹H-NMR (400.0 MHz, DMSO-d6): δ = 6.40; 6.54; 7.11; 7.57; 7.79; 8.10; 8.18, (m, 7H, hetaryl-H); 8.65; 8.87 (d, 2H, hetaryl-H) ppm LogP value (neutral) = 2.14 |
| IV-32 | CH=CH–CH=CH– | 2-(CF₃–CF–CF₃)-pyridin-5-yl | ¹H-NMR (400.0 MHz, CDCl₃): δ = 8.76 (d, 2.4 Hz, 1H), 8.08 (dd, 8.5, 2.4 Hz, 1H), 7.85 (dd, 8.5, 2.5 Hz, 1H), 7.46 (m, 1H), 7.35 (dd, 7.1, 1.6 Hz, 1H), 6.70 (d, 9.9 Hz, 1H), 6.35 (dd, 7.1, 1.0 Hz, 1H) ppm. ¹³C-NMR (600 MHz, CDCl₃) δ = 161.8, 147.0 (d, 25.8 Hz), 147.0 (d, 2.6 Hz), 140.6, 138.8, 136.5, 135.7 (d, 2.0 Hz), 122.3, 122.1 (d, 9.1 Hz), 120.1 (qd, 287.6, 28.0 Hz), 107.1, 90.7 (dhept, 203.0, 32.0 Hz) ppm. LogP value (HCOOH) = 2.40 |
| IV-34 | CH=CH–CH=CH– | 2-(SCH₃)-pyridin-5-yl | ¹H-NMR (400.0 MHz, DMSO-d₆): δ = 2.55 (s, 3H, hetaryl-SCH₃); 6.34; 6.51 7.45; 7.52; 7.68; 7.75, (m, 6H, hetaryl-H); 8.48 (s, 1H, hetaryl-H) ppm. LogP value (neutral) = 1.16 |

TABLE 2

Analytical data for compounds of the formula (VI)

[Structure: six-membered ring with A¹–A²–A³–A⁴ and N–C(=S), with R on N]

| Example No. | [A¹–A²–A³–A⁴ ring] | R | ¹H NMR [δ (ppm)] or logP value (HCOOH) |
|---|---|---|---|
| VI-2 | [butadienyl] | [5-(6-trifluoromethyl)pyridyl] | ¹H-NMR (400.0 MHz, d₆-DMSO): δ = 8.869 (11.6); 8.864 (11.6); 8.317 (0.3); 8.270 (5.5); 8.265 (5.4); 8.249 (8.0); 8.244 (7.9); 8.159 (16.0); 8.149 (9.5); 8.147 (9.5); 8.138 (12.7); 8.135 (10.1); 8.133 (9.9); 7.601 (6.4); 7.579 (11.7); 7.537 (6.4); 7.533 (6.3); 7.520 (7.1); 7.516 (8.7); 7.511 (4.1); 7.498 (4.0); 7.494 (3.7); 6.974 (5.3); 6.970 (5.3); 6.957 (10.0); 6.953 (9.7); 6.940 (5.0); 6.937 (4.7); 3.331 (114.9); 2.671 (1.0); 2.667 (0.8); 2.506 (121.8); 2.502 (151.4); 2.498 (113.3); 2.329 (1.0); 2.086 (0.5); 1.320 (1.4); 1.188 (0.7); 0.000 (59.9); LogP value (HCOOH) = 1.70 |
| VI-3 | [N-methyl aza-diene] | [5-(6-trifluoromethyl)pyridyl] | ¹H-NMR (400.0 MHz, d₆-DMSO): δ = 9.004 (12.4); 8.999 (12.6); 8.519 (10.3); 8.515 (11.2); 8.509 (11.0); 8.505 (10.7); 8.383 (6.5); 8.377 (6.3); 8.362 (7.9); 8.356 (7.6); 8.313 (0.5); 8.160 (16.0); 8.139 (13.3); 7.945 (10.4); 7.940 (10.6); 7.922 (11.5); 7.918 (11.2); 7.408 (11.5); 7.398 (11.1); 7.386 (10.5); 7.375 (10.3); 3.871 (0.3); 3.848 (0.3); 3.767 (0.4); 3.752 (0.4); 3.747 (0.6); 3.732 (0.9); 3.725 (0.5); 3.717 (0.6); 3.418 (0.4); 3.370 (0.5); 3.316 (170.3); 3.218 (0.4); 3.171 (0.4); 2.675 (1.0); 2.671 (1.4); 2.666 (1.0); 2.506 (169.4); 2.502 (220.0); 2.497 (161.7); 2.333 (1.0); 2.329 (1.4); 2.324 (1.1); 1.398 (2.0); 0.000 (0.8); LogP value (HCOOH) = 2.08 |
| VI-4 | [CF₃-substituted diene] | [5-(6-trifluoromethyl)pyridyl] | ¹H-NMR (400.0 MHz, d₆-DMSO): δ = 8.917 (12.3); 8.911 (12.4); 8.751 (12.2); 8.329 (5.7); 8.324 (5.5); 8.308 (7.5); 8.303 (7.4); 8.180 (15.0); 8.159 (11.4); 7.729 (4.0); 7.724 (3.7); 7.705 (12.6); 7.700 (12.9); 7.684 (16.0); 7.661 (4.7); 3.317 (106.0); 2.670 (1.1); 2.666 (0.9); 2.506 (144.5); 2.501 (188.0); 2.497 (136.7); 2.328 (1.1); 2.324 (0.8); 1.398 (1.1); 0.000 (6.4); LogP value (HCOOH) = 2.92 |
| VI-6 | [butadienyl] | [6-(3-trifluoromethylpyrazol-1-yl)pyridyl] | ¹H-NMR (400.0 MHz, DMSO-d₆): δ = 6.94; 7.13; 7.50; 7.58; 8.11-8.20; (m, 7H, hetaryl-H); 8.62; 8.89 (d, 2H, hetaryl-H) LogP value (neutral) = 2.63 |
| VI-7 | [butadienyl] | [6-(1,1,2,2-tetrafluoro-2-trifluoromethylethyl)pyridyl...] | LC-MS (ESI positive): 357.1 [M⁺ + H] C₁₃H₇F₇N₂S (356.2 g/mol) |

TABLE 2-continued
Analytical data for compounds of the formula (VI)
| Example No. | 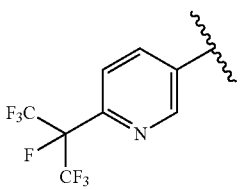 [SMILES: *c1ccc(C(F)(C(F)(F)F)C(F)(F)F)nc1] | R | $^1$H NMR [δ (ppm)] or logP value (HCOOH) |
|---|---|---|---|
| VI-8 | 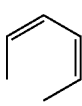 | 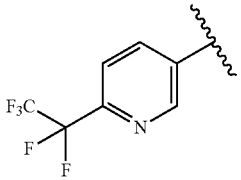 | |
| VI-9 | | 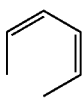 | |
| VI-10 | | 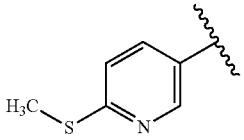 [SMILES: *c1ccc(SC)nc1] | $^1$H-NMR (400.0 MHz, DMSO-d$_6$): δ = 2.56 (s, 3H, hetaryl-SCH$_3$); 6.88; 7.45; 7.54; 7.74; 8.04; 8.43 (m, 7H, hetaryl-H) ppm. LogP value (neutral) = 1.46 |
TABLE 3
Compounds of the formula (I)
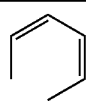
| Example No. | 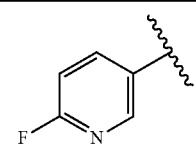 | R | =W—R$^1$ |
|---|---|---|---|
| 9 | | 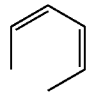 | =N—CO—CF$_3$ |
| 10 | | 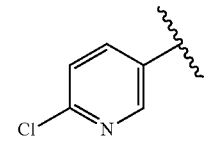 [SMILES: *c1ccc(Cl)nc1] | =N—CO—CF$_3$ |

TABLE 3-continued

Compounds of the formula (I)

| Example No. | A¹–A²–A³–A⁴ | R | =W—R¹ |
|---|---|---|---|
| 11 | (butadienyl) | 5-(CF₃)-pyridin-3-yl | =N—CO—CF₃ |
| 12 | (butadienyl) | 2,3-dichloropyridin-5-yl | =N—CN |
| 13 | 2-methylbutadienyl (CH₃) | 6-(CF₃)-pyridin-3-yl | =N—CN |
| 14 | 1-fluorobutadienyl (F) | 6-(CF₃)-pyridin-3-yl | =N—CN |
| 15 | (butadienyl) | 5-Br-2-(CF₃)-pyridin-3-yl | =N—CN |
| 16 | 1-(CF₃)-butadienyl | 6-(CF₃)-pyridin-3-yl | =N—CN |
| 17 | 1-aza-butadienyl (N-CH₃) | 6-(CF₃)-pyridin-3-yl | =N—CN |
| 18 | (butadienyl) | 6-(CF₃)-pyridazin-3-yl | =N—CN |

TABLE 3-continued

Compounds of the formula (I)

| Example No. | $A^1\text{--}A^2\text{--}A^3\text{--}A^4$ | R | =W—R¹ |
|---|---|---|---|
| 19 | (diene) | 2-(trifluoromethyl)pyrimidin-5-yl | =N—CN |
| 20 | (diene) | 2-methylpyrimidin-5-yl | =N—CN |
| 21 | (diene) | 4-(trifluoromethyl)phenyl | =N—CN |
| 22 | (diene) | 2-methyl-1,3-thiazol-5-yl | =N—CN |
| 23 | (diene) | 6-chloropyridin-3-yl | =N—CN |
| 26 | (diene) | 6-(pentafluoroethyl)pyridin-3-yl | =N—CN |
| 27 | (diene) | 6-[1-fluoro-1-(trifluoromethyl)-2,2,2-trifluoroethyl]pyridin-3-yl | =N—CN |

TABLE 3-continued
Compounds of the formula (I)
| Example No. | ![A1-A2-A3-A4] | R | =W—R¹ |
|---|---|---|---|
| 28 | | 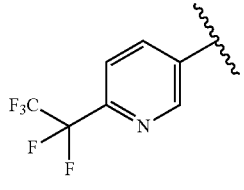 [SMILES: *c1ccc(C(F)(F)C(F)(F)F)nc1] | =N—CN |
| 29 | |  | =N—CN |
TABLE 4
Analytical data for compounds 9 to 29
| Ex. No. | logP value (HCOOH) | $^1$H NMR [δ (ppm)] |
|---|---|---|
| 9 | 1.52 | $^1$H-NMR (400.0 MHz, d$_6$-DMSO): δ = 8.454 (8.1); 8.449 (8.6); 8.448 (8.6); 8.438 (6.9); 8.435 (6.9); 8.422 (16.0); 8.399 (8.7); 8.317 (0.4); 8.279 (4.1); 8.272 (3.9); 8.261 (4.5); 8.257 (5.3); 8.254 (5.0); 8.250 (4.4); 8.239 (4.3); 8.232 (4.0); 8.218 (5.2); 8.214 (5.3); 8.201 (5.7); 8.196 (8.8); 8.191 (4.5); 8.178 (4.2); 8.174 (4.3); 7.454 (6.8); 7.446 (6.9); 7.432 (6.5); 7.425 (6.5); 7.266 (5.0); 7.262 (4.8); 7.248 (7.6); 7.246 (8.2); 7.232 (4.7); 7.228 (4.7); 3.327 (68.7); 2.680 (0.5); 2.676 (1.0); 2.671 (1.4); 2.667 (1.0); 2.662 (0.5); 2.524 (3.6); 2.520 (5.4); 2.511 (74.1); 2.507 (153.4); 2.502 (204.5); 2.497 (148.6); 2.493 (71.8); 2.338 (0.4); 2.333 (0.9); 2.329 (1.3); 2.324 (1.0); 2.320 (0.5); 2.086 (3.0); 1.398 (4.4); 0.146 (1.2); 0.020 (0.4); 0.008 (8.6); 0.000 (263.4); −0.009 (9.2); −0.150 (1.2) |
| 10 | 1.78 | $^1$H-NMR (400.0 MHz, d$_6$-DMSO): δ = 8.621 (14.2); 8.614 (14.4); 8.427 (14.4); 8.424 (15.2); 8.412 (8.2); 8.407 (9.5); 8.401 (11.1); 8.317 (0.4); 8.218 (5.3); 8.213 (5.1); 8.200 (6.0); 8.196 (9.0); 8.191 (5.0); 8.177 (4.5); 8.173 (4.5); 8.145 (9.3); 8.138 (9.1); 8.124 (10.4); 8.117 (10.2); 7.786 (16.0); 7.765 (14.2); 7.270 (5.2); 7.267 (5.1); 7.252 (9.3); 7.250 (9.2); 7.236 (4.9); 7.232 (5.0); 3.324 (80.0); 2.675 (1.2); 2.671 (1.6); 2.666 (1.2); 2.524 (4.2); 2.510 (93.4); 2.506 (187.0); 2.502 (247.4); 2.497 (184.3); 2.493 (93.2); 2.333 (1.2); 2.328 (1.6); 2.324 (1.2); 2.086 (0.8); 1.398 (1.9); 0.146 (0.8); 0.008 (5.9); 0.000 (172.6); −0.008 (7.3); −0.150 (0.8) |
| 11 | 2.09 | $^1$H-NMR (400.0 MHz, d$_6$-DMSO): δ = 9.153 (9.6); 9.151 (9.5); 9.073 (9.6); 9.067 (10.1); 8.648 (9.8); 8.530 (6.3); 8.527 (6.4); 8.514 (6.6); 8.511 (6.3); 8.458 (6.7); 8.436 (8.1); 8.245 (4.3); 8.241 (4.4); 8.227 (4.8); 8.223 (7.5); 8.218 (4.0); 8.205 (3.8); 8.200 (3.6); 7.301 (4.2); 7.297 (4.5); 7.283 (7.4); 7.281 (7.6); 7.266 (4.1); 7.263 (4.1); 4.557 (1.7); 3.331 (102.3); 2.676 (0.7); 2.672 (0.9); 2.667 (0.7); 2.554 (0.9); 2.525 (2.6); 2.511 (49.5); 2.507 (100.2); 2.503 (132.1); 2.498 (97.6); 2.480 (4.5); 2.334 (0.6); 2.329 (0.8); 2.325 (0.6); 2.118 (6.6); 1.235 (2.0); 1.140 (16.0); 0.008 (0.5); 0.000 (16.6); −0.009 (0.7) |

TABLE 4-continued

Analytical data for compounds 9 to 29

| Ex. No. | logP value (HCOOH) | $^1$H NMR [δ (ppm)] |
|---|---|---|
| 12 | 1.53 | $^1$H-NMR (601.6 MHz, $d_6$-DMSO): δ = 8.633 (14.4); 8.629 (15.6); 8.573 (16.0); 8.569 (14.1); 8.010 (6.9); 8.008 (7.2); 7.999 (7.2); 7.997 (7.1); 7.891 (4.3); 7.888 (4.2); 7.879 (4.9); 7.876 (7.3); 7.873 (4.6); 7.864 (4.8); 7.861 (4.4); 7.265 (8.8); 7.250 (8.3); 6.840 (4.9); 6.838 (4.6); 6.828 (9.4); 6.826 (8.9); 6.817 (4.8); 6.815 (4.4); 3.311 (20.8); 2.615 (0.3); 2.612 (0.5); 2.610 (0.3); 2.522 (0.9); 2.519 (1.0); 2.516 (0.9); 2.504 (54.1); 2.501 (72.1); 2.498 (53.3); 2.388 (0.3); 2.385 (0.5); 2.382 (0.3); 1.139 (0.3); 0.000 (5.3) |
| 13 | 1.47 | $^1$H-NMR (400.0 MHz, $d_6$-DMSO): δ = 8.925 (12.1); 8.919 (12.6); 8.324 (6.1); 8.318 (6.0); 8.303 (7.9); 8.298 (7.8); 8.171 (16.0); 8.150 (12.2); 7.864 (7.9); 7.862 (8.5); 7.848 (8.3); 7.846 (8.5); 7.665 (8.1); 7.649 (8.1); 7.647 (8.3); 6.767 (8.5); 6.750 (15.4); 6.733 (8.0); 3.318 (66.2); 2.691 (0.4); 2.675 (0.8); 2.670 (1.2); 2.666 (0.9); 2.532 (62.9); 2.506 (127.2); 2.501 (171.4); 2.497 (133.0); 2.369 (0.4); 2.332 (0.8); 2.328 (1.1); 2.324 (0.9); 2.086 (3.1); 1.398 (3.0); 0.146 (0.5); 0.008 (4.8); 0.000 (102.6); −0.008 (4.7); −0.150 (0.4) |
| 14 | 1.53 | $^1$H-NMR (400.0 MHz, $d_6$-DMSO): δ = 8.972 (13.0); 8.967 (13.1); 8.446 (7.7); 8.438 (9.7); 8.436 (9.7); 8.428 (7.6); 8.380 (6.1); 8.374 (6.0); 8.359 (7.8); 8.353 (7.6); 8.313 (0.7); 8.207 (16.0); 8.186 (12.6); 8.061 (4.9); 8.054 (4.6); 8.043 (5.3); 8.036 (9.1); 8.029 (5.1); 8.018 (5.4); 8.011 (4.8); 7.315 (7.7); 7.302 (7.9); 7.290 (7.3); 7.278 (7.2); 3.317 (201.9); 2.675 (1.4); 2.670 (2.0); 2.666 (1.5); 2.523 (5.8); 2.510 (125.1); 2.506 (252.4); 2.501 (333.7); 2.497 (244.0); 2.492 (119.7); 2.332 (1.5); 2.328 (2.0); 2.323 (1.5); 1.398 (6.3); 1.235 (0.9); 0.146 (1.5); 0.008 (12.6); 0.000 (316.7); −0.009 (12.5); −0.150 (1.5) |
| 15 | 1.79 | $^1$H-NMR (400.0 MHz, $d_6$-DMSO): δ = 9.201 (0.4); 9.136 (15.5); 9.131 (16.0); 8.806 (0.4); 8.767 (15.3); 8.762 (15.3); 8.313 (0.7); 8.088 (8.6); 8.072 (8.8); 7.935 (5.2); 7.931 (5.2); 7.918 (6.0); 7.913 (8.9); 7.908 (6.0); 7.895 (6.1); 7.891 (5.7); 7.273 (12.2); 7.250 (11.4); 6.878 (6.0); 6.875 (6.3); 6.861 (11.6); 6.858 (11.9); 6.844 (6.0); 6.841 (6.0); 6.190 (0.7); 5.754 (1.8); 3.317 (185.4); 2.675 (1.3); 2.670 (1.7); 2.666 (1.3); 2.524 (4.6); 2.510 (102.9); 2.506 (210.1); 2.501 (279.7); 2.497 (204.8); 2.493 (101.6); 2.333 (1.2); 2.328 (1.7); 2.324 (1.2); 1.236 (0.6); 0.008 (0.6); 0.000 (16.5); −0.008 (0.6) |
| 16 | | $^1$H-NMR (601.6 MHz, $d_6$-DMSO): δ = 9.024 (0.3); 9.004 (12.6); 9.001 (12.8); 8.740 (13.3); 8.434 (0.4); 8.410 (7.1); 8.406 (7.2); 8.396 (8.2); 8.392 (8.3); 8.322 (0.4); 8.217 (16.0); 8.203 (13.7); 8.115 (8.2); 8.111 (8.4); 8.099 (8.5); 8.095 (8.7); 7.411 (11.5); 7.395 (10.8); 4.215 (0.4); 4.194 (0.3); 4.153 (0.4); 4.150 (0.3); 4.134 (0.3); 4.121 (0.4); 4.102 (0.4); 4.060 (0.5); 3.979 (0.5); 3.952 (0.5); 3.929 (0.5); 3.896 (0.5); 3.879 (0.5); 3.848 (0.5); 3.819 (0.6); 3.789 (0.6); 3.773 (0.6); 3.760 (0.6); 3.747 (0.6); 3.712 (0.7); 3.705 (0.7); 3.697 (0.7); 3.682 (0.8); 3.659 (0.8); 3.594 (1.0); 3.578 (1.0); 3.553 (1.1); 3.541 (1.2); 3.494 (1.5); 3.332 (134.6); 3.328 (94.9); 3.324 (90.6); 3.322 (101.4); 3.264 (0.9); 3.251 (0.8); 3.174 (0.5); 3.162 (0.5); 3.133 (0.4); 3.099 (0.4); 3.072 (0.3); 3.061 (0.4); 3.032 (0.4); 3.022 (0.3); 2.659 (0.3); 2.625 (1.3); 2.566 (0.5); 2.554 (0.7); 2.532 (2.7); 2.513 (159.3); 2.511 (134.7); 2.463 (1.3); 2.444 (0.8); 2.398 (1.5); 2.381 (0.5); 2.349 (0.5); 2.336 (0.4); 2.322 (0.4); 2.299 (0.4); 2.195 (0.4); 2.098 (0.4); 1.411 (1.2); 1.055 (0.5); 1.046 (0.7); 0.012 (1.1) |
| 17 | 1.64 | $^1$H-NMR (400.0 MHz, $d_6$-DMSO): δ = 9.040 (11.6); 9.035 (12.0); 8.433 (10.3); 8.430 (13.2); 8.423 (15.2); 8.420 (16.0); 8.405 (6.8); 8.400 (6.9); 8.313 (0.8); 8.183 (14.4); 8.162 (12.0); 7.842 (6.6); 7.838 (7.2); 7.818 (15.0); 7.814 (14.3); 7.780 (14.4); 7.770 (13.4); 7.756 (6.7); 7.746 (6.9); 3.317 (202.2); 2.675 (1.2); 2.671 (1.7); 2.666 (1.2); 2.524 (3.8); 2.511 (101.1); 2.506 (211.6); 2.502 (283.2); 2.497 (205.5); 2.493 (99.2); 2.333 (1.2); 2.328 (1.7); 2.324 (1.2); 2.086 (1.1); 1.398 (2.9); 1.235 (0.4); 0.008 (1.7); 0.000 (51.9); −0.009 (1.9) |
| 18 | 1.39 | $^1$H-NMR (400.0 MHz, $d_6$-DMSO): δ = 8.606 (16.0); 8.181 (1.9); 8.179 (2.0); 8.164 (2.0); 8.162 (2.0); 7.974 (1.1); 7.970 (1.2); 7.957 (1.3); 7.952 (2.0); 7.947 (1.3); 7.934 (1.3); 7.930 (1.3); 7.330 (2.6); 7.308 (2.4); 6.934 (1.3); 6.932 (1.4); 6.917 (2.5); 6.914 (2.7); 6.900 (1.3); 6.897 (1.3); 3.316 (29.1); 2.506 (27.7); 2.502 (37.3); 2.497 (28.9) |

TABLE 4-continued

Analytical data for compounds 9 to 29

| Ex. No. | logP value (HCOOH) | $^1$H NMR [δ (ppm)] |
|---|---|---|
| 19 | 1.40 | $^1$H-NMR (400.0 MHz, d$_6$-DMSO): δ = 9.374 (16.0); 8.079 (2.5); 8.065 (2.5); 8.062 (2.5); 7.941 (1.4); 7.936 (1.5); 7.923 (1.6); 7.918 (2.5); 7.914 (1.7); 7.901 (1.6); 7.897 (1.6); 7.309 (3.3); 7.287 (3.0); 6.916 (1.6); 6.914 (1.7); 6.899 (3.1); 6.897 (3.2); 6.882 (1.5); 6.879 (1.6); 5.754 (0.9); 3.317 (11.4); 2.506 (31.3); 2.502 (41.5); 2.497 (31.4); 0.008 (0.9); 0.000 (23.6); −0.008 (1.1) |
| 20 | | $^1$H-NMR (400.0 MHz, d$_6$-DMSO): δ = 9.434 (0.4); 8.900 (11.3); 8.831 (3.9); 8.025 (1.7); 8.009 (1.7); 7.898 (0.9); 7.894 (0.9); 7.881 (1.0); 7.876 (1.6); 7.872 (1.1); 7.858 (1.0); 7.855 (1.0); 7.774 (0.5); 7.770 (0.6); 7.757 (0.5); 7.753 (0.6); 7.566 (0.3); 7.560 (0.6); 7.555 (0.5); 7.542 (0.4); 7.538 (0.5); 7.267 (2.1); 7.244 (2.0); 6.847 (1.1); 6.832 (2.1); 6.815 (1.0); 6.541 (0.8); 6.518 (0.7); 6.409 (0.4); 6.391 (0.7); 6.375 (0.4); 5.753 (0.4); 3.328 (12.5); 2.724 (16.0); 2.697 (6.0); 2.505 (33.1); 2.501 (42.9); 2.497 (33.4); 2.132 (0.8); 1.236 (0.6); 0.000 (43.2) |
| 21 | 1.87 | $^1$H-NMR (400.0 MHz, d$_6$-DMSO): δ = 7.982 (5.9); 7.969 (16.0); 7.948 (13.0); 7.888 (3.1); 7.884 (3.1); 7.871 (3.4); 7.867 (5.6); 7.862 (3.7); 7.849 (3.5); 7.845 (3.4); 7.757 (12.3); 7.736 (10.3); 7.269 (7.2); 7.246 (6.6); 6.820 (3.5); 6.817 (3.7); 6.803 (6.7); 6.800 (7.0); 6.786 (3.4); 6.783 (3.5); 3.317 (43.8); 2.670 (0.6); 2.666 (0.5); 2.523 (1.6); 2.506 (71.6); 2.501 (95.3); 2.497 (72.9); 2.332 (0.4); 2.328 (0.6); 2.324 (0.5); 0.146 (0.5); 0.008 (3.9); 0.000 (108.1); −0.150 (0.5) |
| 22 | 0.80 | $^1$H-NMR (400.0 MHz, d$_6$-DMSO): δ = 8.113 (1.6); 8.098 (1.6); 8.096 (1.6); 7.917 (5.2); 7.850 (0.8); 7.846 (0.9); 7.833 (0.9); 7.828 (1.5); 7.824 (1.0); 7.811 (0.9); 7.807 (0.9); 7.253 (1.9); 7.231 (1.8); 6.809 (1.0); 6.807 (1.0); 6.792 (1.8); 6.790 (1.9); 6.775 (0.9); 6.773 (1.0); 3.318 (6.9); 2.691 (16.0); 2.524 (0.5); 2.506 (19.8); 2.502 (26.0); 2.498 (20.1); 2.086 (0.6); 0.000 (1.0) |
| 23 | 1.07 | $^1$H-NMR (400.0 MHz, d$_6$-DMSO): δ = 8.591 (13.5); 8.584 (14.1); 8.313 (0.5); 8.123 (9.4); 8.116 (9.2); 8.102 (10.5); 8.095 (10.3); 8.004 (8.0); 8.002 (8.5); 7.987 (8.4); 7.985 (8.5); 7.890 (4.9); 7.886 (4.9); 7.873 (5.4); 7.869 (8.8); 7.864 (5.6); 7.851 (5.5); 7.847 (5.2); 7.771 (16.0); 7.750 (14.1); 7.263 (10.7); 7.241 (10.0); 6.831 (5.7); 6.828 (5.6); 6.814 (10.8); 6.811 (10.6); 6.797 (5.4); 6.794 (5.2); 3.316 (88.5); 2.675 (0.9); 2.670 (1.3); 2.666 (1.0); 2.523 (3.6); 2.506 (141.9); 2.501 (188.7); 2.497 (141.9); 2.333 (0.9); 2.328 (1.3); 2.324 (0.9); 2.086 (6.3); 1.398 (1.2); 1.236 (0.5); 0.146 (1.4); 0.025 (0.4); 0.008 (11.2); 0.000 (285.8); −0.008 (13.2); −0.150 (1.4) |
| 26* | 2.36; 2.40 | LC-MS (ESI positive): 365.1 [M$^+$] C$_{14}$H$_7$F$_7$N$_4$ (364.2 g/mol) |
| 27* | 2.47; 2.50 | LC-MS (ESI positive): 365.0 [M$^+$] C$_{14}$H$_7$F$_7$N$_4$ (364.2 g/mol) |
| 28* | 1.96; 1.99 | LC-MS (ESI positive): 315.0 [M$^+$] C$_{11}$H$_7$F$_5$N$_4$ (314.2 g/mol) |
| 29 | 1.19; 1.21 | $^1$H-NMR (400.0 MHz, DMSO-d$_6$): δ = 2.56 (s, 3H, hetaryl-SCH$_3$); 6.79; 7.23; 7.49; 7.85; 7.96; 8.52 (m, 7H, hetaryl-H) ppm. |

*LC-MS (ESI positive)

BIOLOGICAL EXAMPLES

*Boophilus microplus*—Injection Test

Solvent: dimethyl sulphoxide

To produce a suitable active compound preparation, 10 mg of active compound are mixed with 0.5 ml of solvent and the concentrate is diluted with solvent to the desired concentration.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days.

An efficacy of 100% means that none of the ticks has laid any fertile eggs; 0% means that all the eggs are fertile.

In this test, for example, the following compound from the preparation examples showed an efficacy of 90% at an application rate of 20 µg/animal: 9

*Ctenocephalides felis*—Oral Test

Solvent: dimethyl sulphoxide

To produce a suitable active compound preparation, 10 mg of active compound are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined. 100% means that all of the fleas have been killed; 0% means that none of the fleas have been killed.

In this test, for example, the following compound of the preparation examples showed an efficacy of 95% at an application rate of 100 ppm: 1

In this test, for example, the following compound of the preparation examples showed an efficacy of 80% at an application rate of 100 ppm: 16

*Lucilia cuprina*—Test

Solvent: dimethyl sulphoxide

To produce a suitable active compound preparation, 10 mg of active compound are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined. 100% means that all the larvae have been killed; 0% means that no larvae have been killed.

In this test, for example, the following compounds of the preparation examples showed an efficacy of 100% at an application rate of 100 ppm: 1, 4, 9, 10

In this test, for example, the following compound of the preparation examples showed an efficacy of 95% at an application rate of 100 ppm: 7

*Myzus persicae*—Spray Test

Solvent: 78 parts by weight of acetone
1.5 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all the aphids have been killed; 0% means that no aphids have been killed.

In this test, for example, the following compounds from the preparation examples showed an efficacy of 100% at an application rate of 500 g/ha: 1, 7, 19

In this test, for example, the following compounds from the preparation examples showed an efficacy of 90% at an application rate of 500 g/ha: 4, 8, 16, 23

In this test, for example, the following compounds from the preparation examples showed an efficacy of 100% at an application rate of 100 g/ha: 10, 19

In this test, for example, the following compounds from the preparation examples showed an efficacy of 90% at an application rate of 100 g/ha: 2, 3, 14, 18, 29

*Phaedon cochleariae*—Spray Test

Solvent: 78.0 parts by weight of acetone
1.5 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples showed an efficacy of 100% at an application rate of 500 g/ha: 1, 3, 8, 9, 19, 23

*Spodoptera frugiperda*—Spray Test

Solvent: 78.0 parts by weight of acetone
1.5 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillars have been killed.

In this test, for example, the following compound of the preparation examples showed, at an application rate of 500 g/ha, an efficacy of 100%: 23

*Tetranychus urticae*—Spray Test, OP-Resistant

Solvent: 78.0 parts by weight of acetone
1.5 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples showed an efficacy of 100% at an application rate of 500 g/ha: 1

In this test, for example, the following compound of the preparation examples showed, at an application rate of 100 g/ha, an efficacy of 100%: 29

In this test, for example, the following compound of the preparation examples showed, at an application rate of 100 g/ha, an efficacy of 90%: 16

*Myzus persicae*—Spray Test

Solvent: 14 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bell pepper plants (*Capsicum annuum*) severely infested with the green peach aphid (*Myzus persicae*) are treated by spraying with the active compound preparation in the desired concentration.

After 6 days, the kill in % is determined. 100% means that all of the aphids have been killed; 0% means that none of the aphids have been killed.

In this test, for example, the following compound of the preparation examples showed, at an application rate of 20 ppm, an efficacy of 90%: 12

The invention claimed is:

1. A compound of formula (I)

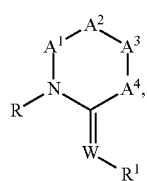
(I)

wherein the structural unit of the formula

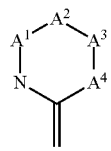

represents a radical A selected from the group consisting of

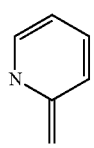
A-1

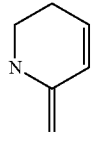
A-2

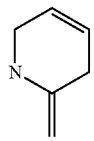
A-3

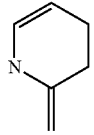
A-4

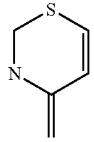
A-5

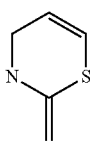
A-6

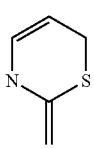
A-7

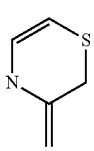
A-8

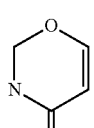
A-9

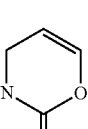
A-10

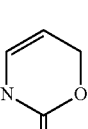
A-11

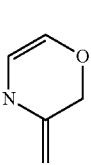
A-12

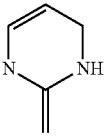
A-13

-continued

A-14
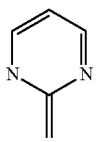

A-15
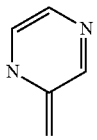

A-16
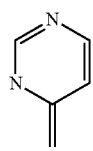

A-17
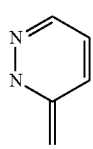

A-18
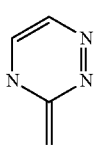

A-19
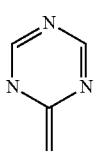

A-20
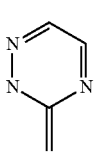

A-21
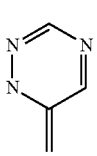

A-22
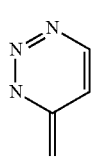

A-23
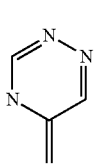

wherein these radicals carry m substituents X,
X represents a radical selected from the group consisting of halogen, cyano (CN), nitro, alkyl, alkoxy, alkylthio, alkylsulphinyl, alkylsulphonyl, haloalkyl, haloalkoxy, haloalkylthio, haloalkylsulphonyl, alkoxycarbonyl, alkylcarbonyl and cycloalkylcarbonyl, m represents a number selected from the group consisting of 0, 1 and 2, R represents a radical B selected from the group consisting of B-2

B-3

B-4

B-5

B-6

B-7

B-8

B-9

B-10

-continued

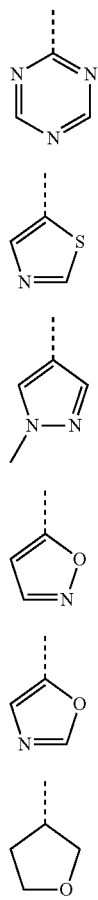

B-11

B-12

B-13

B-14

B-15

B-16 wherein these radicals carry n substituents Y and the dashed line represents the bond to the nitrogen atom in radical A, Y represents a radical selected from the group consisting of halogen, cyano, nitro, amino, alkyl, alkenyl, alkynyl, haloalkyl, alkoxy, haloalkoxy, alkylthio, haloalkylthio, alkylsulphinyl, haloalkylsulphinyl, alkylsulphonyl, haloalkylsulphonyl, alkoxycarbonyl, alkylcarbonyl, cycloalkylcarbonyl, alkylamino, dialkylamino, alkylaminosulphonyl, dialkylaminosulphonyl, alkylaminocarbonyl, dialkylaminocarbonyl, alkylcarbonylamino, alkoxyalkylcarbonylamino, haloalkylcarbonylamino and in each case optionally substituted aryl and hetaryl, n represents a number selected from the group consisting of 0, 1 and 2, W represents CH or N (nitrogen) and $R^1$ represents a radical selected from the group consisting of nitro, cyano, CS—$NH_2$ and CO—$CF_3$.

2. The compound of formula (I) according to claim 1 wherein the structural unit of the formula represents a radical A selected from the group consisting of

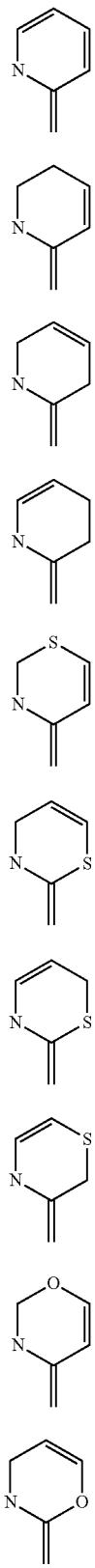

A-1

A-2

A-3

A-4

A-5

A-6

A-7

A-8

A-9

A-10

-continued

A-11 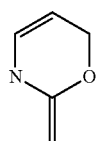

A-12 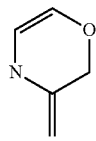

A-13 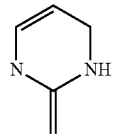

A-14 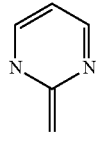

A-15 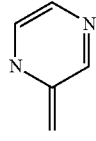

A-16 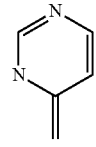

A-17 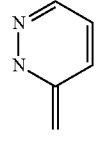

A-18 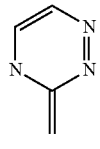

A-19 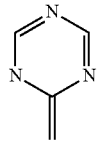

A-20 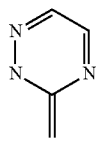

-continued

A-21 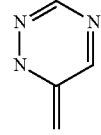

A-22 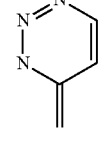

A-23 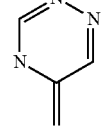

wherein these radicals carry m substituents X,

X represents a radical selected from the group consisting of halogen, cyano, nitro, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, halo-$C_1$-$C_4$-alkyl, halo-$C_1$-$C_4$-alkoxy, halo-$C_1$-$C_4$-alkylthio, halo-$C_1$-$C_4$-alkylsulphonyl, $C_1$-$C_4$-alkoxycarbonyl, $C_1$-$C_4$-alkylcarbonyl and $C_3$-$C_6$-cycloalkylcarbonyl, m represents a number selected from the group consisting of 0, 1 and 2, R represents a radical B selected from the group consisting of B-2 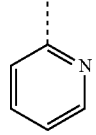

B-3 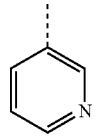

B-4 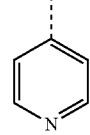

B-5 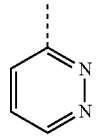

B-6 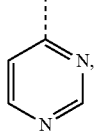

-continued

B-7 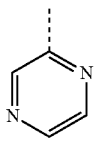

B-8 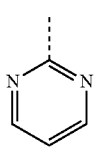

B-9 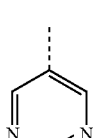

B-10 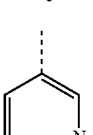

B-11 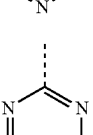

B-12 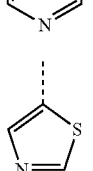

B-13 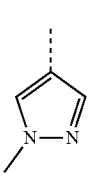

B-14 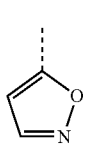

B-15 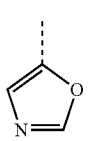

B-16 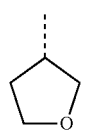

wherein these radicals carry n substituents Y and the dashed line represents the bond to the nitrogen atom in radical A, Y represents a radical selected from the group consisting of halogen, cyano, nitro, amino, $C_1$-$C_4$-alkyl, $C_2$-$C_4$-alkenyl, $C_2$-$C_4$-alkynyl, halo-$C_1$-$C_4$-alkyl, $C_1$-$C_4$-alkoxy, halo-$C_1$-$C_4$-alkoxy, $C_1$-$C_4$-alkylthio, halo-$C_1$-$C_4$-alkylthio, $C_1$-$C_4$-alkylsulphinyl, halo-$C_1$-$C_4$-alkylsulphinyl, $C_1$-$C_4$-alkylsulphonyl, halo-$C_1$-$C_4$-alkylsulphonyl, $C_1$-$C_4$-alkoxycarbonyl, $C_1$-$C_4$-alkylcarbonyl, $C_3$-$C_6$-cycloalkylcarbonyl, $C_1$-$C_4$-alkylamino, di-($C_1$-$C_4$-alkyl)amino, $C_1$-$C_4$-alkylaminosulphonyl, di-($C_1$-$C_4$-alkyl)aminosulphonyl, $C_1$-$C_4$-alkylaminocarbonyl, di-($C_1$-$C_4$-alkyl)aminocarbonyl, $C_1$-$C_4$-alkylcarbonylamino, $C_1$-$C_4$-alkoxy-$C_1$-$C_4$-alkylcarbonylamino, halo-$C_1$-$C_4$-alkylcarbonylamino, in each case optionally substituted aryl and 5- or 6-membered hetaryl and in the case of aryl and hetaryl in particular in each case optionally halogen-, cyano-, $C_1$-$C_4$-alkyl-, halo-$C_1$-$C_4$-alkyl-, $C_1$-$C_4$-alkoxy-, halo-$C_1$-$C_4$-alkoxy-, $C_1$-$C_4$-alkylthio-, halo-$C_1$-$C_4$-alkylthio-, $C_1$-$C_4$-alkylsulphinyl-, halo-$C_1$-$C_4$-alkylsulphinyl-, $C_1$-$C_4$-alkylsulphonyl- or halo-$C_1$-$C_4$-alkylsulphonyl-substituted phenyl and 5- or 6-membered hetaryl, wherein hetaryl is preferably selected from the group consisting of N-pyrazolyl, N-imidazolyl and N-1,2,4-triazolyl, n represents a number selected from the group consisting of 0, 1 and 2, W represents CH or N (nitrogen) and $R^1$ represents a radical selected from the group consisting of nitro, cyano, CS—$NH_2$ and CO—$CF_3$.

3. The compound of formula (I) according to claim 1 wherein the structural unit of the formula

represents a radical A selected from the group consisting of

A-1 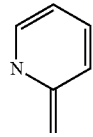

A-14 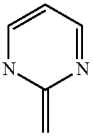

A-15 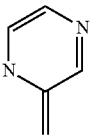

A-16 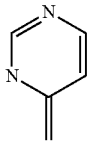

A-17 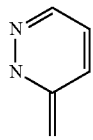

A-18 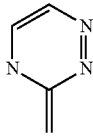

A-19 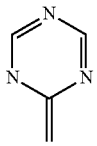

A-20 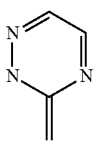

A-21 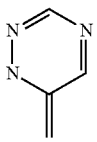

A-22 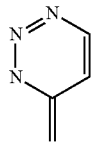

A-23 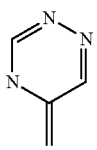

wherein these radicals carry m substituents X,

X represents a radical selected from the group consisting of hydrogen, halogen, cyano, $C_1$-$C_4$-alkyl, and halo-$C_1$-$C_4$-alkyl, m represents a number selected from the group consisting of 0, 1 and 2, R represents a radical B selected from the group consisting of B-2 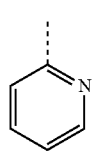

B-3 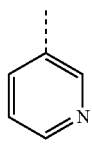

B-4 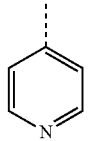

B-5 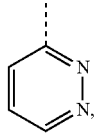

B-7 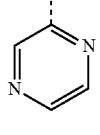

B-9 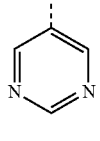

B-10 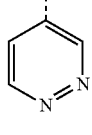

B-12 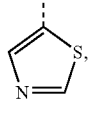

wherein these radicals carry n substituents Y and the dashed line represents the bond to the nitrogen atom in radical A, Y represents a radical selected from the group consisting of halogen, cyano, $C_1$-$C_4$-alkyl, $C_2$-$C_4$-alkenyl, $C_2$-$C_4$-alkynyl, halo-$C_1$-$C_4$-alkyl, halo-$C_1$-$C_4$-alkoxy, halo-$C_1$-$C_4$-alkylthio, $C_1$-$C_4$-alkylsulphinyl, halo-$C_1$-$C_4$-alkylsulphinyl, $C_1$-$C_4$-alkylsulphonyl, halo-$C_1$-$C_4$-alkylsulphonyl and 5-membered hetaryl which is optionally substituted by a substituent from the group consisting of halogen, cyano, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkylthio, halo-$C_1$-$C_4$-alkylthio, $C_1$-$C_4$-alkylsulphinyl, halo-$C_1$-$C_4$-alkylsulphinyl, $C_1$-$C_4$-alkylsulphonyl, and halo-$C_1$-$C_4$-alkylsulphonyl, n represents a number selected from the group consisting of 0, 1 and 2, W represents N (nitrogen) and $R^1$ represents cyano or CO—CF$_3$.

4. The compound of formula (I) according to claim 1 wherein the structural unit of the formula

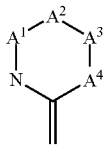

represents a radical A selected from the group consisting of

A-1

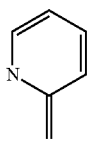

A-17

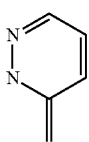

wherein these radicals carry m substituents X,
X represents a radical selected from the group consisting of fluorine, chlorine, bromine, iodine, cyano, methyl, ethyl, trifluoromethyl and difluoromethyl,
m represents a number selected from the group consisting of 0, 1 and 2,
R represents a radical selected from the group consisting of

B-3

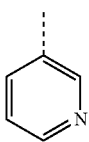

B-5

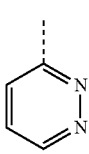

B-7

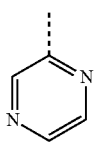

B-9

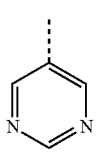

wherein these radicals carry n substituents Y and the dashed line represents the bond to the nitrogen atom in radical A,
Y represents a radical selected from the group consisting of fluorine, chlorine, bromine, iodine, cyano, methyl, fluoromethyl, difluoromethyl, trifluoromethyl, difluorochloromethyl, difluorobromomethyl, 2,2-difluoroethyl, 2,2,2-trifluoroethyl, pentafluoroethyl, difluoromethyl, trifluoromethoxy, difluoromethylthio, trifluoromethylthio, difluoromethylsulphinyl, trifluoromethylsulphinyl, difluoromethylsulphonyl, trifluoromethylsulphonyl, N-triazolyl and N-pyrazolyl which is optionally substituted by a substituent from the group consisting of fluorine, chlorine, iodine, cyano, difluoromethyl, trifluoromethyl, difluoromethoxy, trifluoromethoxy and methylthio,
n represents a number selected from the group consisting of 0, 1 and 2,
W represents N (nitrogen) and
$R^1$ represents cyano.

5. A composition comprising at least one compound of the formula (I) according to claim 1 and one or more extenders and/or surfactants.

6. The compound of formula (I) according to claim 1, wherein the compound is of formula (I-P-1), (I-P-1)

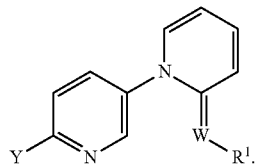

7. The compound of formula (I-P-1) according to claim 6, wherein
W represents N (nitrogen),
Y represents fluorine, and
$R^1$ represents cyano.

8. A method of controlling an animal pest comprising applying the compound of formula (I) according to claim 1 to the animal pest or habitat thereof.

9. The method according to claim 8, wherein the animal pest is an insect, arachnid, helminth, nematode, or mollusc.

10. The method according to claim 8, wherein the animal pest is selected from the group consisting of *Boophilus microplus*, *Ctenocephalides felis*, *Lucilia cuprina*, *Myzus persicae*, *Phaedon cochleariae*, *Spodoptera frugiperda*, and *Tetranychus urticae*.

11. The compound of formula (I) according to claim 1, which is

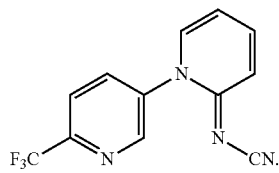

12. The compound of formula (I) according to claim 1, which is

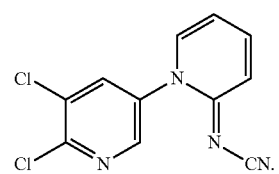 [SMILES: N#C/N=c1\ccccn1-c1cnc(Cl)c(Cl)c1]

13. The compound of formula (I) according to claim 1, which is
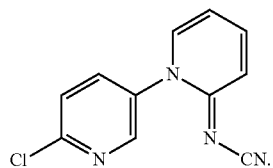 [SMILES: N#C/N=c1\ccccn1-c1ccc(Cl)nc1]
14. The compound of formula (I) according to claim 1, which is
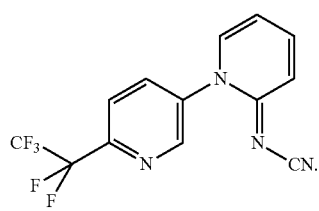 [SMILES: N#C/N=c1\ccccn1-c1ccc(C(F)(F)C(F)(F)F)nc1]
* * * * *